US012767979B2

(12) United States Patent
Zhang et al.

(10) Patent No.: US 12,767,979 B2
(45) Date of Patent: Oct. 20, 2026

(54) QUANTITATIVE AMPLICON SEQUENCING FOR MULTIPLEXED COPY NUMBER VARIATION DETECTION AND ALLELE RATIO QUANTITATION

(71) Applicant: William Marsh Rice University, Houston, TX (US)

(72) Inventors: David Zhang, Houston, TX (US); Peng Dai, Houston, TX (US); Ruojia Wu, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1329 days.

(21) Appl. No.: 17/420,476

(22) PCT Filed: Jan. 2, 2020

(86) PCT No.: PCT/US2020/012089

§ 371 (c)(1),
(2) Date: Jul. 2, 2021

(87) PCT Pub. No.: WO2020/142631

PCT Pub. Date: Jul. 9, 2020

(65) Prior Publication Data

US 2022/0098642 A1 Mar. 31, 2022

Related U.S. Application Data

(60) Provisional application No. 62/788,375, filed on Jan. 4, 2019.

(51) Int. Cl.
*C12Q 1/68* (2018.01)
*C12Q 1/6851* (2018.01)
(Continued)

(52) U.S. Cl.
CPC ........... *C12Q 1/686* (2013.01); *C12Q 1/6851* (2013.01); *C12Q 1/6853* (2013.01); *C12Q 1/6858* (2013.01)

(58) Field of Classification Search
CPC ... C12Q 1/6851; C12Q 1/6853; C12Q 1/6858
See application file for complete search history.

(56) References Cited

U.S. PATENT DOCUMENTS 8,728,766 B2 * 5/2014 Casbon ................ C12Q 1/6869 435/6.12
2007/0196849 A1 * 8/2007 Spier .................... C12Q 1/6827 435/6.16

(Continued)

FOREIGN PATENT DOCUMENTS

EP 2770090 8/2014
JP 2015-526073 9/2015

(Continued)

OTHER PUBLICATIONS

Wang, WB, et al. Allele-specific copy-number discovery from whole-genome and whole-exome sequencing. 2015, Nuc Acids Research, 43, e90. (Year: 2015).*

(Continued)

*Primary Examiner* — Stephanie K Mummert
(74) *Attorney, Agent, or Firm* — pH IP Law

(57) ABSTRACT

Provided herein are methods of quantitative amplicon sequencing, for labeling each strand of targeted genomic loci in a DNA sample with an oligonucleotide barcode sequence by polymerase chain reaction, and amplifying the genomic region(s) for high-throughput sequencing. The methods can be used for the simultaneous detection of copy number variation (CNV) in a set of genes of interest, by quantifying the frequency of extra copies of each gene. In addition, these methods provide for the quantitation of the allele ratio of different genetic identities for targeted genomic loci using (Continued)

multiplexed PCR. In addition, these methods provide for the detection of mutations and quantitation of the variant allele frequency.

12 Claims, 16 Drawing Sheets

Specification includes a Sequence Listing.

(51) Int. Cl.

| | |
|---|---|
| ***C12Q 1/6853*** | (2018.01) |
| ***C12Q 1/6858*** | (2018.01) |
| ***C12Q 1/686*** | (2018.01) |

(56) References Cited

U.S. PATENT DOCUMENTS

| | | | | |
|---|---|---|---|---|
| 2014/0309128 | A1 | 10/2014 | Regan et al. | |
| 2018/0023135 | A1* | 1/2018 | Van Eijk .............. | C12Q 1/6827 435/6.1 |
| 2018/0211003 | A1 | 7/2018 | Travers et al. | |
| 2022/0098642 | A1* | 3/2022 | Zhang .................. | C12Q 1/6851 |

FOREIGN PATENT DOCUMENTS

| | | |
|---|---|---|
| WO | WO 2016-181128 | 11/2016 |
| WO | WO 2018-162538 | 9/2018 |

OTHER PUBLICATIONS

Smith, T, et al. UMI-tools: modeling sequencing errors in Unique Molecular Identifiers to improve quantification accuracy. 2017. Genome Research. 491-499. (Year: 2017).*

Masunaga et al. Highly sensitive detection of ESR1 mutations in cell-free DNA from patients with metastatic breast cancer using molecular barcode sequencing. 2018, Breast Cancer Res Treat (2018) 167: 49-58 (Year: 2018).*

Kerkhof et al. (J of Molec Diagn, 2017, 19(6):905-920) (Year: 2017).*

Office Action issued in Japanese Application No. 2021-538955, mailed Feb. 1, 2024, and English translation thereof.

Extended European Search Report issued in European Application No. 20736142.9, mailed Sep. 16, 2022.

Masunaga et al., "Highly sensitive detection of ESR1 mutations in cell-free DNA from patients with metastatic breast cancer using molecular barcode sequencing," *Breast Cancer Research and Treatment*, 167(1):49-58, 2018.

PCT International Search Report and Written Opinion issued in International Application No. PCT/US2020/012089, mailed Mar. 9, 2020.

* cited by examiner

SEQUENCE LISTING

<160> NUMBER OF SEQ ID NOS: 599

<210> SEQ ID NO 1
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is any of a, c, or t

<400> SEQUENCE: 1
acacgacgct cttccgatct atcannnnnn nnnnnnnnna atcataaaag ctaacatata 60
gcctggg 67

<210> SEQ ID NO 2
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 2
acacgacgct cttccgatct atcannnnnn nnnnnnnnng ctgacttggg gacacagg 58

<210> SEQ ID NO 3
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 3
acacgacgct cttccgatct atcannnnnn nnnnnnnnnc tttgcaagat ggaggttgca 60

<210> SEQ ID NO 4
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 4
acacgacgct cttccgatct atcannnnnn nnnnnnnnnc ttgccctacc agcctctc 58

<210> SEQ ID NO 5
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 5
acacgacgct cttccgatct atcannnnnn nnnnnnnnnc cacaactgga atctgacgc 59

<210> SEQ ID NO 6
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 6
acacgacgct cttccgatct atcannnnnn nnnnnnnnng gctgcggatt gtgcg 55

<210> SEQ ID NO 7
<211> LENGTH: 65
<212> TYPE: DNA
<213> ORGANISM: Artificial Sequence
<220> FEATURE:
<223> OTHER INFORMATION: Synthetic polynucleotide
<220> FEATURE:

<221> NAME/KEY: misc_feature
<222> LOCATION: (25)..(39)
<223> OTHER INFORMATION: n is a, c, or t

<400> SEQUENCE: 7
acacgacgct cttccgatct atcannnnnn nnnnnnnnnc agatataagg gccaaaagtt 60
acaca 65

<210> SEQ ID NO 8
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 8
acacgacgct cttccgatct atcannnnnn nnnnnnnnnt gctttggtct cccttttttgc 60

<210> SEQ ID NO 9
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 9
acacgacgct cttccgatct atcannnnnn nnnnnnnnng aatgaaatta aacagggctt 60
ggc 63

<210> SEQ ID NO 10
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 10
acacgacgct cttccgatct atcannnnnn nnnnnnnnna aagaaaaaaa aaaagaatat 60
gggtccaga 69

<210> SEQ ID NO 11
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 11
acacgacgct cttccgatct atcannnnnn nnnnnnnnng cacaacattt tgtctccgga 60
aaata 65

<210> SEQ ID NO 12
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 12
acacgacgct cttccgatct atcannnnnn nnnnnnnnng acaaatgccc agaaatggaa 60
ctta 64

<210> SEQ ID NO 13
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 13
acacgacgct cttccgatct atcannnnnn nnnnnnnnna tgcggtttca ccattggc 58

<210> SEQ ID NO 14
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 14
acacgacgct cttccgatct atcannnnnn nnnnnnnnnc ccaaggaatt gaggaagttg 60
ct 62

<210> SEQ ID NO 15
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 15
acacgacgct cttccgatct atcannnnnn nnnnnnnnna ctggaatgct gttccttaca 60
atca 64

<210> SEQ ID NO 16
<211> LENGTH: 58
<212> TYPE: DNA
<213> ORGANISM: Artificial Sequence
<220> FEATURE:
<223> OTHER INFORMATION: Synthetic polynucleotide
<220> FEATURE:

```
<221> NAME/KEY: misc_feature
<222> LOCATION: (25)..(39)
<223> OTHER INFORMATION: n is a, c, or t

<400> SEQUENCE: 16

acacgacgct cttccgatct atcannnnnn nnnnnnnnng gcctggatag gcagcttg       58


<210> SEQ ID NO 17
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 17

acacgacgct cttccgatct atcannnnnn nnnnnnnnnc aactcagact attcaggaat     60

acgttt                                                                66


<210> SEQ ID NO 18
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 18

acacgacgct cttccgatct atcannnnnn nnnnnnnnnt ccatccgaca ttgaagttga     60

ctta                                                                  64


<210> SEQ ID NO 19
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 19

acacgacgct cttccgatct atcannnnnn nnnnnnnnng aatgaagccc taatccctta     60

agc                                                                   63


<210> SEQ ID NO 20
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 20

acacgacgct cttccgatct atcannnnnn nnnnnnnnnc aggcagagga aatatcgttg     60

ac                                                                    62
```

<210> SEQ ID NO 21
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 21
ggatattcct ttctactctt tgacatcatc tatgcatgca aaacaccaca aac 53

<210> SEQ ID NO 22
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 22
ggatattcct ttctactctt tgacatcatc tcagatctgg cccagcacc 49

<210> SEQ ID NO 23
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 23
ggatattcct ttctactctt tgacatcatc tcctggcagg cactctcg 48

<210> SEQ ID NO 24
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 24
ggatattcct ttctactctt tgacatcatc tcctaaggtc aaatcctagg ggg 53

<210> SEQ ID NO 25
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 25
ggatattcct ttctactctt tgacatcatc tcggggctct ggtcattgc 49

<210> SEQ ID NO 26
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 26
ggatattcct ttctactctt tgacatcatc ttcagcgggt ctccattgtc ta 52

<210> SEQ ID NO 27
<211> LENGTH: 54
<212> TYPE: DNA
<213> ORGANISM: Artificial Sequence
<220> FEATURE:

<223> OTHER INFORMATION: Synthetic polynucleotide

<400> SEQUENCE: 27
ggatattcct ttctactctt tgacatcatc tgcttggtgg ttaagagact gtgg 54

<210> SEQ ID NO 28
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 28
ggatattcct ttctactctt tgacatcatc tccatttacc cctcacaaca acca 54

<210> SEQ ID NO 29
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 29
ggatattcct ttctactctt tgacatcatc tcgagtaaca acagtcactg ctc 53

<210> SEQ ID NO 30
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 30
ggatattcct ttctactctt tgacatcatc tatgtttttc catgttctaa caccgt 56

<210> SEQ ID NO 31
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 31
ggatattcct ttctactctt tgacatcatc tgctccagat gggcagcac 49

<210> SEQ ID NO 32
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 32
ggatattcct ttctactctt tgacatcatc tttggcagtc tttaagatcc atagaaatac 60

<210> SEQ ID NO 33
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 33
ggatattcct ttctactctt tgacatcatc tactttggaa ggcagaggcg 50

<210> SEQ ID NO 34
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 34
ggatattcct ttctactctt tgacatcatc ttggaactcg tctcactatt caattttt 58

<210> SEQ ID NO 35
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 35
ggatattcct ttctactctt tgacatcatc tctgcttgtg gatgaggcca ta 52

<210> SEQ ID NO 36
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 36
ggatattcct ttctactctt tgacatcatc taggcagtca ctgttccttt cc 52

<210> SEQ ID NO 37
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 37
ggatattcct ttctactctt tgacatcatc tatgcattta cttctgaaac agtcctt 57

<210> SEQ ID NO 38
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 38
ggatattcct ttctactctt tgacatcatc tcaagtctga atgctccact ttttca 56

<210> SEQ ID NO 39
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 39
ggatattcct ttctactctt tgacatcatc tgtctcattc tagaaagaag ttaactcatt 60
ataca 65

<210> SEQ ID NO 40
<211> LENGTH: 57
<212> TYPE: DNA
<213> ORGANISM: Artificial Sequence
<220> FEATURE:

<223> OTHER INFORMATION: Synthetic polynucleotide

<400> SEQUENCE: 40
ggatattcct ttctactctt tgacatcatc taggaatcaa caaatgacaa ggcaaat 57

<210> SEQ ID NO 41
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 41
agacgtgtgc tcttccgatc tcatgcaaaa caccacaaac agttc 45

<210> SEQ ID NO 42
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 42
agacgtgtgc tcttccgatc tgatctggcc cagcacctta a 41

<210> SEQ ID NO 43
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 43
agacgtgtgc tcttccgatc tctctcggtg gatctgcata acat 44

<210> SEQ ID NO 44
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 44
agacgtgtgc tcttccgatc tgtcaaatcc tagggggtaa tacga 45

<210> SEQ ID NO 45
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 45
agacgtgtgc tcttccgatc tctggtcatt gcagagacct ct 42

<210> SEQ ID NO 46
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 46
agacgtgtgc tcttccgatc ttctccattg tctagcacgg c 41

<210> SEQ ID NO 47
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 47
agacgtgtgc tcttccgatc tagactgtgg agtctgaaac tcag 44

<210> SEQ ID NO 48
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 48
agacgtgtgc tcttccgatc tcccctcaca acaaccagac g 41

<210> SEQ ID NO 49
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 49
agacgtgtgc tcttccgatc tgtcactgct ctgtagaaag cct 43

<210> SEQ ID NO 50
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 50
agacgtgtgc tcttccgatc tatgttctaa caccgtgatc tggat 45

<210> SEQ ID NO 51
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 51
agacgtgtgc tcttccgatc tatgggcagc acagtggg 38

<210> SEQ ID NO 52
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 52
agacgtgtgc tcttccgatc tgcagtcttt aagatccata gaaatactct t 51

<210> SEQ ID NO 53
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 53
agacgtgtgc tcttccgatc tcagaggcga gtggatcact t 41

<210> SEQ ID NO 54
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 54
agacgtgtgc tcttccgatc tactattcaa ttttttccta gagcatctcc 50

<210> SEQ ID NO 55
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 55
agacgtgtgc tcttccgatc tggccataga aagggtagtg ttgaa 45

<210> SEQ ID NO 56
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 56
agacgtgtgc tcttccgatc tttcctttcc tcctcctccc at 42

<210> SEQ ID NO 57
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 57
agacgtgtgc tcttccgatc tgcatttact tctgaaacag tccttaatg 49

<210> SEQ ID NO 58
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 58
agacgtgtgc tcttccgatc taatgctcca ctttttcaat tctctct 47

<210> SEQ ID NO 59
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 59
agacgtgtgc tcttccgatc tattctagaa agaagttaac tcattataca cagt 54

<210> SEQ ID NO 60
<211> LENGTH: 46

<212> TYPE: DNA
<213> ORGANISM: Artificial Sequence
<220> FEATURE:
<223> OTHER INFORMATION: Synthetic polynucleotide

<400> SEQUENCE: 60
agacgtgtgc tcttccgatc tacaaatgac aaggcaaatg agacat 46

<210> SEQ ID NO 61
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 61
acactctttc cctacacgac gctcttccga tct 33

<210> SEQ ID NO 62
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 62
cctatggtag ttaaatgtac attggatatt cctttctact ctttgacatc atct 54

<210> SEQ ID NO 63
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 63
acacgacgct cttccgatct atcannnnnn nnnnnnnnnc cttagacaac tacctttcta 60
cggac 65

<210> SEQ ID NO 64
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 64
acacgacgct cttccgatct atcannnnnn nnnnnnnnnt gctttggtct cccttttttgc 60

<210> SEQ ID NO 65
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 65
acacgacgct cttccgatct atcannnnnn nnnnnnnnna aagaaaaaaa aaaagaatat 60
gggtccaga 69

<210> SEQ ID NO 66
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 66
acacgacgct cttccgatct atcannnnnn nnnnnnnnnc gaggcgatag ggttaaggg 59

<210> SEQ ID NO 67
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 67
acacgacgct cttccgatct atcannnnnn nnnnnnnnnc ttctagtcgc aattgaagta 60
ccac 64

<210> SEQ ID NO 68
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 68
acacgacgct cttccgatct atcannnnnn nnnnnnnnnc ctcacccctt gtcaactttt 60
c 61

<210> SEQ ID NO 69
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 69
acacgacgct cttccgatct atcannnnnn nnnnnnnnng tctggtgctt tagcccaaag 60

<210> SEQ ID NO 70
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 70
acacgacgct cttccgatct atcannnnnn nnnnnnnnna aagcaaagct atattcaaga 60
ccacat 66

<210> SEQ ID NO 71
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 71
acacgacgct cttccgatct atcannnnnn nnnnnnnnng gcattgtctg ccagtccg 58

<210> SEQ ID NO 72
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 72
acacgacgct cttccgatct atcannnnnn nnnnnnnnnt cctttagctc gtggaatctc 60
aag 63

<210> SEQ ID NO 73
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 73
acacgacgct cttccgatct atcannnnnn nnnnnnnnnc tggggcattc caactagaac 60
t 61

<210> SEQ ID NO 74
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 74
acacgacgct cttccgatct atcannnnnn nnnnnnnnna ttccagtggc catcaaagtg 60
t 61

<210> SEQ ID NO 75
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 75
acacgacgct cttccgatct atcannnnnn nnnnnnnnng ggaaaaccat tatttgatat 60
taaaacaaat agg 73

<210> SEQ ID NO 76
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 76
acacgacgct cttccgatct atcannnnnn nnnnnnnnna ggaagtataa gaatgaagtt 60
gtgaagc 67

<210> SEQ ID NO 77
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 77
acacgacgct cttccgatct atcannnnnn nnnnnnnnnc tccccgctcc ccttca 56

<210> SEQ ID NO 78
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 78
acacgacgct cttccgatct atcannnnnn nnnnnnnnna gcctgggcca ggtatact 58

<210> SEQ ID NO 79
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 79
acacgacgct cttccgatct atcannnnnn nnnnnnnnna ctctgtcctc tgcaggaact 60

<210> SEQ ID NO 80
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 80
acacgacgct cttccgatct atcannnnnn nnnnnnnnng tatgggtttt acaaattgca 60
gcaaata 67

<210> SEQ ID NO 81
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 81
acacgacgct cttccgatct atcannnnnn nnnnnnnnnc aaagcatgtt taattttctc 60
gtggtt 66

<210> SEQ ID NO 82
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 82
acacgacgct cttccgatct atcannnnnn nnnnnnnnng cgtgaggggc cagtgt 56

<210> SEQ ID NO 83
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 83
acacgacgct cttccgatct atcannnnnn nnnnnnnnng gacacaggtc attttactgt 60
agtattc 67

<210> SEQ ID NO 84
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 84
acacgacgct cttccgatct atcannnnnn nnnnnnnnnc cacccgttct gaccctc 57

<210> SEQ ID NO 85
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 85
acacgacgct cttccgatct atcannnnnn nnnnnnnnnc aggaagcata cgtgatggct 60

<210> SEQ ID NO 86
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 86
acacgacgct cttccgatct atcannnnnn nnnnnnnnna cctgcagtgt gcaaggg 57

<210> SEQ ID NO 87
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 87
acacgacgct cttccgatct atcannnnnn nnnnnnnnng cgtctgtgtt tccgctaaat 60
c 61

<210> SEQ ID NO 88
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 88
acacgacgct cttccgatct atcannnnnn nnnnnnnnna agatctccaa gtactgggga 60
ac 62

<210> SEQ ID NO 89
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 89
acacgacgct cttccgatct atcannnnnn nnnnnnnnnt ggccttcacc gtcattgaaa 60

<210> SEQ ID NO 90
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 90
acacgacgct cttccgatct atcannnnnn nnnnnnnnng cagatataag ggccaaaagt 60
tacac 65

<210> SEQ ID NO 91
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 91
acacgacgct cttccgatct atcannnnnn nnnnnnnnnc agctggctct cacactgat 59

<210> SEQ ID NO 92
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 92
acacgacgct cttccgatct atcannnnnn nnnnnnnnnc cacccctgtt ctccgatg 58

<210> SEQ ID NO 93
<211> LENGTH: 70
<212> TYPE: DNA
<213> ORGANISM: Artificial Sequence
<220> FEATURE:
<223> OTHER INFORMATION: Synthetic polynucleotide
<220> FEATURE:

<221> NAME/KEY: misc_feature
<222> LOCATION: (25)..(39)
<223> OTHER INFORMATION: n is a, c, or t

<400> SEQUENCE: 93
acacgacgct cttccgatct atcannnnnn nnnnnnnnnc tcctaaatgt tagcttttat 60
tctatagcct 70

<210> SEQ ID NO 94
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 94
acacgacgct cttccgatct atcannnnnn nnnnnnnnna gtctctgcct tctactctct 60
acc 63

<210> SEQ ID NO 95
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 95
acacgacgct cttccgatct atcannnnnn nnnnnnnnng cctttggtgg gtgggg 56

<210> SEQ ID NO 96
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 96
acacgacgct cttccgatct atcannnnnn nnnnnnnnng atgagctacc tggaggatgt 60
g 61

<210> SEQ ID NO 97
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 97
acacgacgct cttccgatct atcannnnnn nnnnnnnnnc agccagttcc ctggttca 58

<210> SEQ ID NO 98
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 98
acacgacgct cttccgatct atcannnnnn nnnnnnnnnc ccttcagact atgaaaaggt 60
tctaag 66

<210> SEQ ID NO 99
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 99
acacgacgct cttccgatct atcannnnnn nnnnnnnnna cagtgctggc aatgtttatc 60
ac 62

<210> SEQ ID NO 100
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 100
acacgacgct cttccgatct atcannnnnn nnnnnnnnng ggtggttccc agaattgttg 60

<210> SEQ ID NO 101
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 101
acacgacgct cttccgatct atcannnnnn nnnnnnnnnc ttcaaagttc tggtgtcggg 60

<210> SEQ ID NO 102
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 102
acacgacgct cttccgatct atcannnnnn nnnnnnnnnt gacctgtggg tggaaatttt 60
g 61

<210> SEQ ID NO 103
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 103
acacgacgct cttccgatct atcannnnnn nnnnnnnnna gagggttctg attgcctaca 60
ag 62

<210> SEQ ID NO 104
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 104
acacgacgct cttccgatct atcannnnnn nnnnnnnnng ggatcctcat caagcgacg 59

<210> SEQ ID NO 105
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 105
acacgacgct cttccgatct atcannnnnn nnnnnnnnnc ccttttacag tcaaagtcca 60
aagc 64

<210> SEQ ID NO 106
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 106
acacgacgct cttccgatct atcannnnnn nnnnnnnnng ggtcgtcaaa gacgtttttg 60
c 61

<210> SEQ ID NO 107
<211> LENGTH: 58

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 107
acacgacgct cttccgatct atcannnnnn nnnnnnnnng atggcgctgg agtccatt 58

<210> SEQ ID NO 108
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 108
acacgacgct cttccgatct atcannnnnn nnnnnnnnna cctgtcctaa ggaaccttcc 60
t 61

<210> SEQ ID NO 109
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 109
acacgacgct cttccgatct atcannnnnn nnnnnnnnnc tttgcaagat ggaggttgca 60

<210> SEQ ID NO 110
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 110
acacgacgct cttccgatct atcannnnnn nnnnnnnnnc ttgccctacc agcctctc 58

<210> SEQ ID NO 111
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 111
acacgacgct cttccgatct atcannnnnn nnnnnnnnnc cacaactgga atctgacgc 59

<210> SEQ ID NO 112
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 112
acacgacgct cttccgatct atcannnnnn nnnnnnnnng gctgcggatt gtgcg 55

<210> SEQ ID NO 113
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 113
acacgacgct cttccgatct atcannnnnn nnnnnnnnng ggacccactc catcgaga 58

<210> SEQ ID NO 114
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 114
acacgacgct cttccgatct atcannnnnn nnnnnnnnng gagtatttca tgaaacaaat 60
gaatgatgc 69

<210> SEQ ID NO 115
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 115
acacgacgct cttccgatct atcannnnnn nnnnnnnnng ccgccaggtc ttgatgtact 60

<210> SEQ ID NO 116
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 116
acacgacgct cttccgatct atcannnnnn nnnnnnnnnc tcaccatcgc tatctgagca 60
g 61

<210> SEQ ID NO 117
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 117
acacgacgct cttccgatct atcannnnnn nnnnnnnnnt cgtcaaggca ctcttgccta 60

<210> SEQ ID NO 118
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 118
acacgacgct cttccgatct tcttnnnnnn nnnnnnnnng agtatttgga tgacagaaac 60
acttt 65

<210> SEQ ID NO 119
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 119
acacgacgct cttccgatct tcttnnnnnn nnnnnnnnnc acacgcaaat ttccttccac 60

<210> SEQ ID NO 120
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 120
acacgacgct cttccgatct tcttnnnnnn nnnnnnnnnc cgctcatgat caaacgctct 60
aa 62

<210> SEQ ID NO 121
<211> LENGTH: 61
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 121
acacgacgct cttccgatct tcttnnnnnn nnnnnnnnnt ccatgatcag gtccaccttc 60
t 61

<210> SEQ ID NO 122
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 122
acacgacgct cttccgatct tcttnnnnnn nnnnnnnnnt cactctctct ctgcgcattc 60

<210> SEQ ID NO 123
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 123
acacgacgct cttccgatct tcttnnnnnn nnnnnnnnna gtaacaaagg catggagcat 60
ct 62

<210> SEQ ID NO 124
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 124
acacgacgct cttccgatct tcttnnnnnn nnnnnnnnng tggggtgaga tttttgtcaa 60
ctt 63

<210> SEQ ID NO 125
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 125
acacgacgct cttccgatct tcttnnnnnn nnnnnnnnna gcagtatcag tagtatgagc 60
agc 63

<210> SEQ ID NO 126
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 126
acacgacgct cttccgatct tcttnnnnnn nnnnnnnnnt tctgatgtgc tttgttctgg 60
attt 64

<210> SEQ ID NO 127
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 127
acacgacgct cttccgatct tcttnnnnnn nnnnnnnnnt gagccaaatg tgtatgggtg 60
a 61

<210> SEQ ID NO 128
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 128
acacgacgct cttccgatct tcttnnnnnn nnnnnnnnng ttgcacattc ctcttctgca 60
ttt 63

<210> SEQ ID NO 129
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 129
acacgacgct cttccgatct tcttnnnnnn nnnnnnnnng gtgcatttgt taacttcagc 60
tctg 64

<210> SEQ ID NO 130
<211> LENGTH: 60
<212> TYPE: DNA

<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 130
acacgacgct cttccgatct tcttnnnnnn nnnnnnnnnt aggtttctgc tgtgcctgac 60

<210> SEQ ID NO 131
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 131
acacgacgct cttccgatct tcttnnnnnn nnnnnnnnng gtgggcttag atttctactg 60
actacta 67

<210> SEQ ID NO 132
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 132
acacgacgct cttccgatct tcttnnnnnn nnnnnnnnnt ctaggattct ctgagcatgg 60
c 61

<210> SEQ ID NO 133
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 133
acacgacgct cttccgatct tcttnnnnnn nnnnnnnnna ctaaatagga aaataccagc 60
ttcatagac 69

<210> SEQ ID NO 134
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 134
acacgacgct cttccgatct tcttnnnnnn nnnnnnnnna cactcttgtg ctgacttacc 60
a 61

<210> SEQ ID NO 135
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 135
acacgacgct cttccgatct tcttnnnnnn nnnnnnnnna acatcaggga attcatttaa 60
agtaaatagc 70

<210> SEQ ID NO 136
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 136
acacgacgct cttccgatct tcttnnnnnn nnnnnnnnng gaaccaaatg atactgatcc 60
attagattc 69

<210> SEQ ID NO 137
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 137
acacgacgct cttccgatct tcttnnnnnn nnnnnnnnna gattctaaac tgccaagtca 60
tgc 63

<210> SEQ ID NO 138
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 138
acacgacgct cttccgatct tcttnnnnnn nnnnnnnnnt gcctgtagta atcaagtgtc 60
tcattt 66

<210> SEQ ID NO 139

<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 139
acacgacgct cttccgatct tcttnnnnnn nnnnnnnnnc aaccaaagtc tttgttccac 60
ctt 63

<210> SEQ ID NO 140
<211> LENGTH: 68
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 140
acacgacgct cttccgatct tcttnnnnnn nnnnnnnnna gacatcatct ggattataca 60
tatttcgc 68

<210> SEQ ID NO 141
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 141
acacgacgct cttccgatct tcttnnnnnn nnnnnnnnna aagagctaac atacagttag 60
cagc 64

<210> SEQ ID NO 142
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 142
acacgacgct cttccgatct tcttnnnnnn nnnnnnnnnt tccattctag gacttgcccc 60

<210> SEQ ID NO 143
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 143
acacgacgct cttccgatct tcttnnnnnn nnnnnnnnna ctgaattctc ctcagatgac 60
tcc 63

<210> SEQ ID NO 144
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 144
acacgacgct cttccgatct tcttnnnnnn nnnnnnnnna cagacactcc ttgttcagca 60

<210> SEQ ID NO 145
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 145
acacgacgct cttccgatct tcttnnnnnn nnnnnnnnnt gtgtatataa ttatttctta 60
ccctattcga gtc 73

<210> SEQ ID NO 146
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 146
acacgacgct cttccgatct tcttnnnnnn nnnnnnnnnt tgctgtcatt tggactggga 60
a 61

<210> SEQ ID NO 147
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 147
acacgacgct cttccgatct tcttnnnnnn nnnnnnnnnc aaaaagatac ccacctttcc 60
tcca 64

<210> SEQ ID NO 148

<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 148
acacgacgct cttccgatct tcttnnnnnn nnnnnnnnnc aatttctaca cgagatcctc 60
tctct 65

<210> SEQ ID NO 149
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 149
acacgacgct cttccgatct tcttnnnnnn nnnnnnnnng acattacggg ctgccaaatc 60

<210> SEQ ID NO 150
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 150
acacgacgct cttccgatct tcttnnnnnn nnnnnnnnnc tcagacacac acccagcaa 59

<210> SEQ ID NO 151
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 151
acacgacgct cttccgatct tcttnnnnnn nnnnnnnnna cttactttat aaaccgttcc 60
aaaagca 67

<210> SEQ ID NO 152
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 152
acacgacgct cttccgatct tcttnnnnnn nnnnnnnnnt gagtaatgta cttactacaa 60
ttttcagctt 70

<210> SEQ ID NO 153
<211> LENGTH: 68
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 153
acacgacgct cttccgatct tcttnnnnnn nnnnnnnnng ctgttgtcag taatatagat 60
gtttcctg 68

<210> SEQ ID NO 154
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 154
acacgacgct cttccgatct tcttnnnnnn nnnnnnnnna actagggcag gcacgc 56

<210> SEQ ID NO 155
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 155
acacgacgct cttccgatct tcttnnnnnn nnnnnnnnng gataataaaa gagagaaatc 60
acagacatac aa 72

<210> SEQ ID NO 156
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 156
acacgacgct cttccgatct tcttnnnnnn nnnnnnnnna ggcatatcga tcctcataaa 60
gttttg 66

<210> SEQ ID NO 157
<211> LENGTH: 59
<212> TYPE: DNA

<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 157
acacgacgct cttccgatct tcttnnnnnn nnnnnnnnnt ccaggttgcc catgacaac 59

<210> SEQ ID NO 158
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 158
acacgacgct cttccgatct tcttnnnnnn nnnnnnnnna gtgccagaag gaacccac 58

<210> SEQ ID NO 159
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 159
acacgacgct cttccgatct tcttnnnnnn nnnnnnnnna agtgttactc aagaagcaga 60
aagg 64

<210> SEQ ID NO 160
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 160
acacgacgct cttccgatct tcttnnnnnn nnnnnnnnna aaatcccttt gggttataaa 60
tagtgca 67

<210> SEQ ID NO 161
<211> LENGTH: 78
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 161
acacgacgct cttccgatct tcttnnnnnn nnnnnnnnna tgtgttttat aatttagact 60

```
agtgaatatt tttctttg                                                    78


<210> SEQ ID NO 162
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 162

acacgacgct cttccgatct tcttnnnnnn nnnnnnnnnc tggaaaaatg gctttgaatc      60

tttgg                                                                  65


<210> SEQ ID NO 163
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 163

acacgacgct cttccgatct tcttnnnnnn nnnnnnnnnt ggaaaagctc attaacttaa      60

ctgacat                                                                67


<210> SEQ ID NO 164
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 164

acacgacgct cttccgatct tcttnnnnnn nnnnnnnnnt ccttgggatt acgctccct       59


<210> SEQ ID NO 165
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 165

acacgacgct cttccgatct tcttnnnnnn nnnnnnnnna cccagtggag aagctccc        58


<210> SEQ ID NO 166
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
```

<221> NAME/KEY: misc_feature
<222> LOCATION: (25)..(39)
<223> OTHER INFORMATION: n is a, c, or t

<400> SEQUENCE: 166
acacgacgct cttccgatct tcttnnnnnn nnnnnnnnna ggtgagaaag ttaaaattcc 60
cgtc 64

<210> SEQ ID NO 167
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 167
acacgacgct cttccgatct tcttnnnnnn nnnnnnnnna ggcagatgcc cagcagg 57

<210> SEQ ID NO 168
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 168
acacgacgct cttccgatct tcttnnnnnn nnnnnnnnnc ctccaccgtg cagctcat 58

<210> SEQ ID NO 169
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 169
acacgacgct cttccgatct tcttnnnnnn nnnnnnnnna gccaggaacg tactggtg 58

<210> SEQ ID NO 170
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 170
acacgacgct cttccgatct tcttnnnnnn nnnnnnnnna caatgtcacc acattacata 60
cttacc 66

<210> SEQ ID NO 171
<211> LENGTH: 59

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 171
acacgacgct cttccgatct tcttnnnnnn nnnnnnnnna caggctccca gacatgaca 59

<210> SEQ ID NO 172
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 172
acacgacgct cttccgatct tcttnnnnnn nnnnnnnnnt tcagatattt ctttccttaa 60
ctaaagtact ca 72

<210> SEQ ID NO 173
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 173
acacgacgct cttccgatct tcttnnnnnn nnnnnnnnnt gtttgttttg ttttaaggtt 60
tttggattc 69

<210> SEQ ID NO 174
<211> LENGTH: 71
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 174
acacgacgct cttccgatct tcttnnnnnn nnnnnnnnnt cctaagtgca aaagataact 60
ttatatcact t 71

<210> SEQ ID NO 175
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 175
acacgacgct cttccgatct tcttnnnnnn nnnnnnnnng ttgcagcaat tcactgtaaa 60
gct 63

<210> SEQ ID NO 176
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 176
acacgacgct cttccgatct tcttnnnnnn nnnnnnnnnc acaagaggcc ctagatttct 60
atgg 64

<210> SEQ ID NO 177
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 177
acacgacgct cttccgatct tcttnnnnnn nnnnnnnnnt tgagttccct cagccgttac 60

<210> SEQ ID NO 178
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 178
acacgacgct cttccgatct tcttnnnnnn nnnnnnnnnt cttcatacca ggaccagagg 60
aa 62

<210> SEQ ID NO 179
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 179
acacgacgct cttccgatct tcttnnnnnn nnnnnnnnna gtgagccctg ctcccc 56

<210> SEQ ID NO 180
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 180
acacgacgct cttccgatct tcttnnnnnn nnnnnnnnng cgtgcagata atgacaagga 60
atatct 66

<210> SEQ ID NO 181
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 181
acacgacgct cttccgatct tcttnnnnnn nnnnnnnnng gttttcattt taaattttct 60
ttctctaggt gaa 73

<210> SEQ ID NO 182
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 182
acacgacgct cttccgatct tcttnnnnnn nnnnnnnnnt cgtggccatg aatgaattct 60
cta 63

<210> SEQ ID NO 183
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 183
acacgacgct cttccgatct tcttnnnnnn nnnnnnnnnt ctacaacaag ctaactttcc 60
agct 64

<210> SEQ ID NO 184
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 184
acacgacgct cttccgatct tcttnnnnnn nnnnnnnnng tgatgttcct ccctcatctc 60
taa 63

<210> SEQ ID NO 185
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 185
acacgacgct cttccgatct tcttnnnnnn nnnnnnnnna gcaacattga tggatttgtg 60
aact 64

<210> SEQ ID NO 186
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 186
acacgacgct cttccgatct tcttnnnnnn nnnnnnnnna cgattggctg aagtaccaga 60
c 61

<210> SEQ ID NO 187
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 187
acacgacgct cttccgatct tcttnnnnnn nnnnnnnnnt ggacacgaca acaaccagc 59

<210> SEQ ID NO 188
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 188
acacgacgct cttccgatct tcttnnnnnn nnnnnnnnng caacttacac gtggacgac 59

<210> SEQ ID NO 189
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 189
acacgacgct cttccgatct tcttnnnnnn nnnnnnnnnt ccctcttatt gttccctaca 60
gattg 65

<210> SEQ ID NO 190
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 190
acacgacgct cttccgatct tcttnnnnnn nnnnnnnnng tgcgccggtc tctcc 55

<210> SEQ ID NO 191
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 191
acacgacgct cttccgatct tcttnnnnnn nnnnnnnnnt gacctggagt cttccagtgt 60

<210> SEQ ID NO 192
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 192
acacgacgct cttccgatct atcannnnnn nnnnnnnnng cttgtctaag gaaaaaactt 60
gattattttg taa 73

<210> SEQ ID NO 193
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 193
acacgacgct cttccgatct atcannnnnn nnnnnnnnna ggaagacgct tggttggg 58

<210> SEQ ID NO 194
<211> LENGTH: 71
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 194
acacgacgct cttccgatct atcannnnnn nnnnnnnnnt gagacctata atgctaagga 60
aatttcttta c 71

<210> SEQ ID NO 195
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 195
acacgacgct cttccgatct atcannnnnn nnnnnnnnnt ggaagcgttc gttccatcc 59

<210> SEQ ID NO 196
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 196
acacgacgct cttccgatct atcannnnnn nnnnnnnnng cttggcatct gttcttgctt 60
taa 63

<210> SEQ ID NO 197
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 197
acacgacgct cttccgatct atcannnnnn nnnnnnnnna aaattctgca aaaataaagg 60
ccaaga 66

<210> SEQ ID NO 198
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 198
acacgacgct cttccgatct atcannnnnn nnnnnnnnnt ttattgcatg tcctcatcca 60
cag 63

<210> SEQ ID NO 199
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 199
acacgacgct cttccgatct atcannnnnn nnnnnnnnna ttggggatgt ccagaataaa 60
ttcag 65

<210> SEQ ID NO 200
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 200
acacgacgct cttccgatct atcannnnnn nnnnnnnnnc aaacagttca gtgacttgcc 60
c 61

<210> SEQ ID NO 201
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 201
acacgacgct cttccgatct atcannnnnn nnnnnnnnnc aggcatctca cctctcttcc 60

<210> SEQ ID NO 202
<211> LENGTH: 68
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 202
acacgacgct cttccgatct atcannnnnn nnnnnnnnng gcattattcc agtattgtag 60
aagaagaa 68

<210> SEQ ID NO 203
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 203
acacgacgct cttccgatct atcannnnnn nnnnnnnnnc tacattacca gtagaacaga 60
actagtcta 69

<210> SEQ ID NO 204
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 204
acacgacgct cttccgatct atcannnnnn nnnnnnnnng ctaaccgtgc tttcctcttt 60
cat 63

<210> SEQ ID NO 205
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 205
acacgacgct cttccgatct atcannnnnn nnnnnnnnnc cctagcagaa gccgacca 58

<210> SEQ ID NO 206
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 206
acacgacgct cttccgatct atcannnnnn nnnnnnnnnc aaaccaccac ttatttcttt 60
attttatcct 70

<210> SEQ ID NO 207
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 207
acacgacgct cttccgatct atcannnnnn nnnnnnnnnt cattttgtag tcattgtaaa 60
actcttatgc 70

<210> SEQ ID NO 208
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 208
acacgacgct cttccgatct atcannnnnn nnnnnnnnna gagtagcgac atgcaaatga 60
tct 63

<210> SEQ ID NO 209
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 209
acacgacgct cttccgatct atcannnnnn nnnnnnnnnc ccagcatttg ttatataggc 60
atctt 65

<210> SEQ ID NO 210
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 210
acacgacgct cttccgatct atcannnnnn nnnnnnnnng agtagacagg gaaatataga 60
agcct 65

<210> SEQ ID NO 211
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 211
acacgacgct cttccgatct atcannnnnn nnnnnnnnnc catccttttt agtgctgtcc 60
tca 63

<210> SEQ ID NO 212
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 212
acacgacgct cttccgatct atcannnnnn nnnnnnnnnt cagctggcct agcagttc 58

<210> SEQ ID NO 213
<211> LENGTH: 75
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 213
acacgacgct cttccgatct atcannnnnn nnnnnnnnng cataatttat aatgaaaaca 60
aatacattct cacag 75

<210> SEQ ID NO 214
<211> LENGTH: 69
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 214
acacgacgct cttccgatct atcannnnnn nnnnnnnnnc ttatttgcat ttgtggcata 60
atatgaaac 69

<210> SEQ ID NO 215
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 215
acacgacgct cttccgatct atcannnnnn nnnnnnnnnc tagggttagt caggtggttc 60
aa 62

<210> SEQ ID NO 216
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 216
acacgacgct cttccgatct atcannnnnn nnnnnnnnnc agaagggctc tcactggg 58

<210> SEQ ID NO 217
<211> LENGTH: 73
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 217
acacgacgct cttccgatct atcannnnnn nnnnnnnnng ccttatatta ttccctttga 60
accttacaat aat 73

<210> SEQ ID NO 218
<211> LENGTH: 58
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 218
acacgacgct cttccgatct atcannnnnn nnnnnnnnnc ctgcagcggg agttttca 58

<210> SEQ ID NO 219
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 219
acacgacgct cttccgatct atcannnnnn nnnnnnnnnc ggcgccacgt gttca 55

<210> SEQ ID NO 220
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 220
acacgacgct cttccgatct atcannnnnn nnnnnnnnnt ggcccatttt aacctttttt 60
ttttaaagta 70

<210> SEQ ID NO 221

<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 221
acacgacgct cttccgatct atcannnnnn nnnnnnnnnt gtgaacagcc agaagcgat 59

<210> SEQ ID NO 222
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 222
acacgacgct cttccgatct atcannnnnn nnnnnnnnnc cagcccctga tcctaccag 59

<210> SEQ ID NO 223
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 223
acacgacgct cttccgatct atcannnnnn nnnnnnnnna gtaactgaac gacgaattct 60
ttgtaa 66

<210> SEQ ID NO 224
<211> LENGTH: 57
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 224
acacgacgct cttccgatct atcannnnnn nnnnnnnnnc agctcccacc acagtgc 57

<210> SEQ ID NO 225
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 225
acacgacgct cttccgatct atcannnnnn nnnnnnnnnc acacagcggg ctctca 56

<210> SEQ ID NO 226
<211> LENGTH: 61
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 226
acacgacgct cttccgatct atcannnnnn nnnnnnnnnt cccttctcct acacttcctc 60
c 61

<210> SEQ ID NO 227
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 227
acacgacgct cttccgatct atcannnnnn nnnnnnnnna ctacaggagc aactgccac 59

<210> SEQ ID NO 228
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 228
acacgacgct cttccgatct atcannnnnn nnnnnnnnna gaggtaggga ttattagccc 60
cat 63

<210> SEQ ID NO 229
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 229
acacgacgct cttccgatct atcannnnnn nnnnnnnnnt gtgtatccaa caggaactcc 60
aaa 63

<210> SEQ ID NO 230
<211> LENGTH: 62
<212> TYPE: DNA
<213> ORGANISM: Artificial Sequence
<220> FEATURE:
<223> OTHER INFORMATION: Synthetic polynucleotide
<220> FEATURE:

<221> NAME/KEY: misc_feature
<222> LOCATION: (25)..(39)
<223> OTHER INFORMATION: n is a, c, or t

<400> SEQUENCE: 230
acacgacgct cttccgatct atcannnnnn nnnnnnnnnc tggtcttaaa atgtcctggg 60
ga 62

<210> SEQ ID NO 231
<211> LENGTH: 55
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 231
acacgacgct cttccgatct atcannnnnn nnnnnnnnna cgcccggcca tctca 55

<210> SEQ ID NO 232
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 232
acacgacgct cttccgatct atcannnnnn nnnnnnnnnt tttcactgtt tcctacaaga 60
aaatgc 66

<210> SEQ ID NO 233
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 233
acacgacgct cttccgatct atcannnnnn nnnnnnnnng aaacctggat ttttgaaatc 60
tagtgtttaa 70

<210> SEQ ID NO 234
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 234
acacgacgct cttccgatct atcannnnnn nnnnnnnnng caaggacgga aataggtaaa 60
tgt 63

<210> SEQ ID NO 235
<211> LENGTH: 56
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 235
acacgacgct cttccgatct atcannnnnn nnnnnnnnnc gaggcactgc gtttgg 56

<210> SEQ ID NO 236
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 236
acacgacgct cttccgatct atcannnnnn nnnnnnnnna gcagatgggt tgagagttgg 60

<210> SEQ ID NO 237
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 237
acacgacgct cttccgatct atcannnnnn nnnnnnnnnt ccaatctcta tctgttagaa 60
gtctcc 66

<210> SEQ ID NO 238
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 238
acacgacgct cttccgatct atcannnnnn nnnnnnnnng gctctgattt ccgcccaat 59

<210> SEQ ID NO 239
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 239
acacgacgct cttccgatct atcannnnnn nnnnnnnnnt gcaaagattg taggagctct 60
gta 63

<210> SEQ ID NO 240
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 240
acacgacgct cttccgatct atcannnnnn nnnnnnnnna attagataaa aagcatccac 60
agaggag 67

<210> SEQ ID NO 241
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(39)
<223> OTHER INFORMATION: n is a, c, or t

<400> SEQUENCE: 241
acacgacgct cttccgatct atcannnnnn nnnnnnnnna gtctttaaca atgagagtca 60
aaccatt 67

<210> SEQ ID NO 242
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 242
agacgtgtgc tcttccgatc tgtgcagggg gcagacga 38

<210> SEQ ID NO 243
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 243
agacgtgtgc tcttccgatc tcccctcaca acaaccagac g 41

<210> SEQ ID NO 244
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 244
agacgtgtgc tcttccgatc tatgttctaa caccgtgatc tggat 45

<210> SEQ ID NO 245
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 245
agacgtgtgc tcttccgatc ttggaaaaca cttcagtttg ctcattaa 48

<210> SEQ ID NO 246
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 246
agacgtgtgc tcttccgatc tgcaaaggtt ctaccccgca t 41

<210> SEQ ID NO 247
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 247
agacgtgtgc tcttccgatc tggctacttc ttactcattc caaccc 46

<210> SEQ ID NO 248
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 248
agacgtgtgc tcttccgatc tccatcacca gctagtctga gtc 43

<210> SEQ ID NO 249
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 249
agacgtgtgc tcttccgatc tccccgtttt atctgtgact ctttg 45

<210> SEQ ID NO 250
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 250
agacgtgtgc tcttccgatc tccatcctct ctgcatccca aatc 44

<210> SEQ ID NO 251
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 251
agacgtgtgc tcttccgatc tggcaggtgt tatcattccc cattt 45

<210> SEQ ID NO 252
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 252
agacgtgtgc tcttccgatc tgggcctcct tatttttatg tgctaaat 48

<210> SEQ ID NO 253
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 253
agacgtgtgc tcttccgatc tagggtggag gggcttacg 39

<210> SEQ ID NO 254
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 254
agacgtgtgc tcttccgatc tagcttgcat cctactccat cc 42

<210> SEQ ID NO 255
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 255
agacgtgtgc tcttccgatc ttcccctggt ttctccggt 39

<210> SEQ ID NO 256
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 256
agacgtgtgc tcttccgatc tcgaccccgc cagaagc 37

<210> SEQ ID NO 257
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 257
agacgtgtgc tcttccgatc tgcatgcaaa acaccacaaa cagtt 45

<210> SEQ ID NO 258
<211> LENGTH: 43

<212> TYPE: DNA
<213> ORGANISM: Artificial Sequence
<220> FEATURE:
<223> OTHER INFORMATION: Synthetic polynucleotide

<400> SEQUENCE: 258
agacgtgtgc tcttccgatc tggctacctc cctctgttta tgg 43

<210> SEQ ID NO 259
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 259
agacgtgtgc tcttccgatc taaaatatga aggagttctg caagattaaa ag 52

<210> SEQ ID NO 260
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 260
agacgtgtgc tcttccgatc tggttcatac agcaggaata tgggtaat 48

<210> SEQ ID NO 261
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 261
agacgtgtgc tcttccgatc taggacaggc acaactaccc t 41

<210> SEQ ID NO 262
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 262
agacgtgtgc tcttccgatc tagcagaaaa gccaatactt ccct 44

<210> SEQ ID NO 263
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 263
agacgtgtgc tcttccgatc taacaccaca ggctctacgg 40

<210> SEQ ID NO 264
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 264
agacgtgtgc tcttccgatc tcccagaagg cgggagacat a 41

<210> SEQ ID NO 265
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 265
agacgtgtgc tcttccgatc tcagggagaa gcctgactga ag 42

<210> SEQ ID NO 266
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 266
agacgtgtgc tcttccgatc tggtggacag gggacatgat ca 42

<210> SEQ ID NO 267
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 267
agacgtgtgc tcttccgatc tggaacactg ccaccccc 38

<210> SEQ ID NO 268
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 268
agacgtgtgc tcttccgatc tccccctggt tagcagtgg 39

<210> SEQ ID NO 269
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 269
agacgtgtgc tcttccgatc taactcagcc ccatcactca c 41

<210> SEQ ID NO 270
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 270
agacgtgtgc tcttccgatc tggaggggca tggcttacag 40

<210> SEQ ID NO 271
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 271
agacgtgtgc tcttccgatc tcggctctga caatcctcag aa 42

<210> SEQ ID NO 272
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 272
agacgtgtgc tcttccgatc tggtctcaaa aacaaaacga aaggtaaa 48

<210> SEQ ID NO 273
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 273
agacgtgtgc tcttccgatc tactgacagg ggatataggg aca 43

<210> SEQ ID NO 274
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 274
agacgtgtgc tcttccgatc tagtccttgt tcacggatag cat 43

<210> SEQ ID NO 275
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 275
agacgtgtgc tcttccgatc tgttccgagc ggccaagtc 39

<210> SEQ ID NO 276
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 276
agacgtgtgc tcttccgatc tccgcagggg acttttaggg 40

<210> SEQ ID NO 277
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 277
agacgtgtgc tcttccgatc tctagcacag ccacagtcac a 41

<210> SEQ ID NO 278
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 278
agacgtgtgc tcttccgatc tcatttagtt gtctttaaat tgaaatgcat gaa 53

<210> SEQ ID NO 279
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 279
agacgtgtgc tcttccgatc tccttgtcat ccaggtccac a 41

<210> SEQ ID NO 280
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 280
agacgtgtgc tcttccgatc tactctaact tgaccccctt attcct 46

<210> SEQ ID NO 281
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 281
agacgtgtgc tcttccgatc tacaggaatg tacacctgat gattttg 47

<210> SEQ ID NO 282
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 282
agacgtgtgc tcttccgatc tctgccttgg ctccccg 37

<210> SEQ ID NO 283
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 283
agacgtgtgc tcttccgatc tcagtctccg catcgtgtac t 41

<210> SEQ ID NO 284
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 284
agacgtgtgc tcttccgatc tctgtgccca gcttaatttt gtaca 45

<210> SEQ ID NO 285
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 285
agacgtgtgc tcttccgatc tggggtgtca agtactcggg 40

<210> SEQ ID NO 286
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 286
agacgtgtgc tcttccgatc tacacatcac tctggtgggt gaa 43

<210> SEQ ID NO 287
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 287
agacgtgtgc tcttccgatc ttggacccct tccagcca 38

<210> SEQ ID NO 288
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 288
agacgtgtgc tcttccgatc tctctcggtg gatctgcata acat 44

<210> SEQ ID NO 289
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 289
agacgtgtgc tcttccgatc tgtcaaatcc tagggggtaa tacga 45

<210> SEQ ID NO 290
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 290
agacgtgtgc tcttccgatc tctggtcatt gcagagacct ct 42

<210> SEQ ID NO 291

<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 291
agacgtgtgc tcttccgatc ttctccattg tctagcacgg c 41

<210> SEQ ID NO 292
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 292
agacgtgtgc tcttccgatc tctcacagta aaaataggtg attttggtct 50

<210> SEQ ID NO 293
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 293
agacgtgtgc tcttccgatc taagatccaa tccatttttg ttgtccag 48

<210> SEQ ID NO 294
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 294
agacgtgtgc tcttccgatc tgtctgacgg gtagagtgtg c 41

<210> SEQ ID NO 295
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 295
agacgtgtgc tcttccgatc tcacatgacg gaggttgtga gg 42

<210> SEQ ID NO 296
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 296
agacgtgtgc tcttccgatc tctgaaaatg actgaatata aacttgtggt agt 53

<210> SEQ ID NO 297
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 297
agacgtgtgc tcttccgatc tccagttgca aaccagacct ca 42

<210> SEQ ID NO 298
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 298
agacgtgtgc tcttccgatc ttcctcactg attgctctta ggtct 45

<210> SEQ ID NO 299
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 299
agacgtgtgc tcttccgatc tccaacaagg cactgaccat c 41

<210> SEQ ID NO 300
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 300
agacgtgtgc tcttccgatc tgagcgccag acgagacc 38

<210> SEQ ID NO 301
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 301
agacgtgtgc tcttccgatc tcggtggata tggtccttct cttc 44

<210> SEQ ID NO 302
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 302
agacgtgtgc tcttccgatc tcggtgggcg tccagca 37

<210> SEQ ID NO 303
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 303
agacgtgtgc tcttccgatc ttggtcaatg gaagaaacca cca 43

<210> SEQ ID NO 304
<211> LENGTH: 46
<212> TYPE: DNA

<213> ORGANISM: Artificial Sequence
<220> FEATURE:
<223> OTHER INFORMATION: Synthetic polynucleotide

<400> SEQUENCE: 304
agacgtgtgc tcttccgatc tcatcttcaa cctctgcatt gaaagt 46

<210> SEQ ID NO 305
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 305
agacgtgtgc tcttccgatc taacagctac ccttccatca taagt 45

<210> SEQ ID NO 306
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 306
agacgtgtgc tcttccgatc tctgttttta gcaaaagcgt ccag 44

<210> SEQ ID NO 307
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 307
agacgtgtgc tcttccgatc taggtttcaa agcgccagtc a 41

<210> SEQ ID NO 308
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 308
agacgtgtgc tcttccgatc tgtaacaagc caaatgaaca gacaagt 47

<210> SEQ ID NO 309
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 309
agacgtgtgc tcttccgatc tagttgttct agcagtgaag agataaaga 49

<210> SEQ ID NO 310
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 310
agacgtgtgc tcttccgatc taaagcacct aaaaagaata ggctgag 47

<210> SEQ ID NO 311
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 311
agacgtgtgc tcttccgatc taggtagatc tgaatgctga tccc 44

<210> SEQ ID NO 312
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 312
agacgtgtgc tcttccgatc tggatctgat tcttctgaag ataccgttaa 50

<210> SEQ ID NO 313
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 313
agacgtgtgc tcttccgatc tgatttatct gctcttcgcg ttgaa 45

<210> SEQ ID NO 314
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 314
agacgtgtgc tcttccgatc tactgtttca tatacttcat cttctaggac a 51

<210> SEQ ID NO 315
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 315
agacgtgtgc tcttccgatc tggagatttt gtcacttcca ctctc 45

<210> SEQ ID NO 316
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 316
agacgtgtgc tcttccgatc tttgaatttg acaaaaccat ttcctcattt 50

<210> SEQ ID NO 317
<211> LENGTH: 50
<212> TYPE: DNA
<213> ORGANISM: Artificial Sequence
<220> FEATURE:

<223> OTHER INFORMATION: Synthetic polynucleotide

<400> SEQUENCE: 317
agacgtgtgc tcttccgatc tgtttcagga catccatttt atcaagtttc 50

<210> SEQ ID NO 318
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 318
agacgtgtgc tcttccgatc tgttaatatt cctaacacac tgttcaactc t 51

<210> SEQ ID NO 319
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 319
agacgtgtgc tcttccgatc tttctagtct cttttgttgg gcct 44

<210> SEQ ID NO 320
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 320
agacgtgtgc tcttccgatc tcttatcaaa actgaaaaat tacaatgaaa ggttt 55

<210> SEQ ID NO 321
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 321
agacgtgtgc tcttccgatc tctttattgc cagtaaattg taacattcgt 50

<210> SEQ ID NO 322
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 322
agacgtgtgc tcttccgatc tcaagttctt cgtcagctat tgaattact 49

<210> SEQ ID NO 323
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 323
agacgtgtgc tcttccgatc tccttctctc cacatatgtt tctcttatta a 51

<210> SEQ ID NO 324
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 324
agacgtgtgc tcttccgatc tcatcccacc tcccatctat acttc 45

<210> SEQ ID NO 325
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 325
agacgtgtgc tcttccgatc ttttgtgtct gatgggcaat ctttc 45

<210> SEQ ID NO 326
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 326
agacgtgtgc tcttccgatc tttttgggct agccagactc ttg 43

<210> SEQ ID NO 327
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 327
agacgtgtgc tcttccgatc tgaatctcca ttttagcact tacctgtg 48

<210> SEQ ID NO 328
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 328
agacgtgtgc tcttccgatc tttgatattt ttcagggaat gatgtacctg 50

<210> SEQ ID NO 329
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 329
agacgtgtgc tcttccgatc tgaaatcatg gtattgcatt tttttcttac ag 52

<210> SEQ ID NO 330
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 330
agacgtgtgc tcttccgatc tagcacccaa tcaagctcaa ct 42

<210> SEQ ID NO 331
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 331
agacgtgtgc tcttccgatc tactcttcag cacaatcaac caga 44

<210> SEQ ID NO 332
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 332
agacgtgtgc tcttccgatc tgcatcacct ctctacagtt ccagt 45

<210> SEQ ID NO 333
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 333
agacgtgtgc tcttccgatc tgctgaatgt taacattaat gcttatttta cc 52

<210> SEQ ID NO 334
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 334
agacgtgtgc tcttccgatc tagtgactgc tgccatcgag 40

<210> SEQ ID NO 335
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 335
agacgtgtgc tcttccgatc tgctacgtgt tagtggctct taatca 46

<210> SEQ ID NO 336
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 336
agacgtgtgc tcttccgatc tataaactga gctctctctc tgacc 45

<210> SEQ ID NO 337
<211> LENGTH: 37

<212> TYPE: DNA
<213> ORGANISM: Artificial Sequence
<220> FEATURE:
<223> OTHER INFORMATION: Synthetic polynucleotide

<400> SEQUENCE: 337
agacgtgtgc tcttccgatc ttgaagccgg cgacagg 37

<210> SEQ ID NO 338
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 338
agacgtgtgc tcttccgatc tggttcaatt acttttaaaa agggttgaaa aag 53

<210> SEQ ID NO 339
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 339
agacgtgtgc tcttccgatc tatttgactt taccttatca atgtctcgaa 50

<210> SEQ ID NO 340
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 340
agacgtgtgc tcttccgatc tgtgtctgtg taatcaaaca agtttatatt tcc 53

<210> SEQ ID NO 341
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 341
agacgtgtgc tcttccgatc tagtaacacc aatagggttc agcaa 45

<210> SEQ ID NO 342
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 342
agacgtgtgc tcttccgatc taaagagtct caaacacaaa ctagagtc 48

<210> SEQ ID NO 343
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 343
agacgtgtgc tcttccgatc ttttattgta tttgcatagc acaaattttt gtt 53

<210> SEQ ID NO 344
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 344
agacgtgtgc tcttccgatc tccgtgccga acgcacc 37

<210> SEQ ID NO 345
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 345
agacgtgtgc tcttccgatc tgcaaagcag aaactcacat cga 43

<210> SEQ ID NO 346
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 346
agacgtgtgc tcttccgatc tctccaggaa gcctacgtga tg 42

<210> SEQ ID NO 347
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 347
agacgtgtgc tcttccgatc tcggacatag tccaggaggc ag 42

<210> SEQ ID NO 348
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 348
agacgtgtgc tcttccgatc tgcatggtat tctttctctt ccgca 45

<210> SEQ ID NO 349
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 349
agacgtgtgc tcttccgatc tgggcagatt acagtgggac aa 42

<210> SEQ ID NO 350
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 350
agacgtgtgc tcttccgatc tggatacagg tcaagtctaa gtcgaatc 48

<210> SEQ ID NO 351
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 351
agacgtgtgc tcttccgatc tcctgtatac gccttcaagt ctttct 46

<210> SEQ ID NO 352
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 352
agacgtgtgc tcttccgatc tgcaagcata caaataagaa aacatactta cag 53

<210> SEQ ID NO 353
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 353
agacgtgtgc tcttccgatc ttctgcaatt aaatttggcg gtgt 44

<210> SEQ ID NO 354
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 354
agacgtgtgc tcttccgatc tcgatgtaat aaatatgcac atatcattac acc 53

<210> SEQ ID NO 355
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 355
agacgtgtgc tcttccgatc tcaggaagag gaaaggaaaa acatcaa 47

<210> SEQ ID NO 356
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 356
agacgtgtgc tcttccgatc tgatatttct cccaatgaaa gtaaagtaca aac 53

<210> SEQ ID NO 357
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 357
agacgtgtgc tcttccgatc ttcgatttct tgatcacata gacttccat 49

<210> SEQ ID NO 358
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 358
agacgtgtgc tcttccgatc tgggcgtgag cgcttcg 37

<210> SEQ ID NO 359
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 359
agacgtgtgc tcttccgatc tcttaaaatt tggagaaaag tatcggttgg 50

<210> SEQ ID NO 360
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 360
agacgtgtgc tcttccgatc tagcctctgg atttgacggc 40

<210> SEQ ID NO 361
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 361
agacgtgtgc tcttccgatc tgatggcaaa cttcccatcg tag 43

<210> SEQ ID NO 362
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 362
agacgtgtgc tcttccgatc tgggacagct ggctacacaa 40

<210> SEQ ID NO 363
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 363
agacgtgtgc tcttccgatc taggccctga cacaggatgt 40

<210> SEQ ID NO 364
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 364
agacgtgtgc tcttccgatc tcccattgag gccggtgat 39

<210> SEQ ID NO 365
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 365
agacgtgtgc tcttccgatc tttgaccatc accatgtaga catca 45

<210> SEQ ID NO 366
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 366
agacgtgtgc tcttccgatc tagctgtctc tctcccagtt catt 44

<210> SEQ ID NO 367
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 367
agacgtgtgc tcttccgatc tcccatggca aacaccatga g 41

<210> SEQ ID NO 368
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 368
agacgtgtgc tcttccgatc tcaccatgtg tgacttgatt agcag 45

<210> SEQ ID NO 369
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 369
agacgtgtgc tcttccgatc tgtggtaatc tactgggacg gaac 44

<210> SEQ ID NO 370

<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 370
agacgtgtgc tcttccgatc ttccactaca actacatgtg taacagtt 48

<210> SEQ ID NO 371
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 371
agacgtgtgc tcttccgatc tgtaacagta ggtgtttcaa tatgactttt att 53

<210> SEQ ID NO 372
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 372
agacgtgtgc tcttccgatc tctcccctcc tccataggaa ctt 43

<210> SEQ ID NO 373
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 373
agacgtgtgc tcttccgatc tacataccag gttctgcgct t 41

<210> SEQ ID NO 374
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 374
agacgtgtgc tcttccgatc tatcaaggca ccgctctaac tt 42

<210> SEQ ID NO 375
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 375
agacgtgtgc tcttccgatc tatcccggtg tgcatttgag a 41

<210> SEQ ID NO 376
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 376
agacgtgtgc tcttccgatc tgggctatgg gggcttcct 39

<210> SEQ ID NO 377
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 377
agacgtgtgc tcttccgatc tgatgtgccc tgacatcaga aatatac 47

<210> SEQ ID NO 378
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 378
agacgtgtgc tcttccgatc tagtgttgat ctgaaggaac ttcct 45

<210> SEQ ID NO 379
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 379
agacgtgtgc tcttccgatc ttgggaccat gtttggccat 40

<210> SEQ ID NO 380
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 380
agacgtgtgc tcttccgatc ttcccatcat tgctgctgtc a 41

<210> SEQ ID NO 381
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 381
agacgtgtgc tcttccgatc tcaaacacgt gtgatcaata gtaccat 47

<210> SEQ ID NO 382
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 382
agacgtgtgc tcttccgatc ttctcatatc agaacttaaa tacatagcag tag 53

<210> SEQ ID NO 383
<211> LENGTH: 46
<212> TYPE: DNA

<213> ORGANISM: Artificial Sequence
<220> FEATURE:
<223> OTHER INFORMATION: Synthetic polynucleotide

<400> SEQUENCE: 383
agacgtgtgc tcttccgatc tggggaagga agatgtcaca ttatga 46

<210> SEQ ID NO 384
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 384
agacgtgtgc tcttccgatc tgcatgcgca agagctaccc 40

<210> SEQ ID NO 385
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 385
agacgtgtgc tcttccgatc tacgataaaa ttctcttatc ttgaaggatt gat 53

<210> SEQ ID NO 386
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 386
agacgtgtgc tcttccgatc tagtgtttct gatattgaaa aattttaagt gct 53

<210> SEQ ID NO 387
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 387
agacgtgtgc tcttccgatc ttttcatcct tcgcacatgt atactg 46

<210> SEQ ID NO 388
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 388
agacgtgtgc tcttccgatc tctggagcag atgactcaca tttc 44

<210> SEQ ID NO 389
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 389
agacgtgtgc tcttccgatc tagggggctt ggtctttttt ct 42

<210> SEQ ID NO 390
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 390
agacgtgtgc tcttccgatc tcaccttttt taacaaccgg atctagt 47

<210> SEQ ID NO 391
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 391
agacgtgtgc tcttccgatc tgaggccctg taatctgtat tttaacc 47

<210> SEQ ID NO 392
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 392
agacgtgtgc tcttccgatc tccttaatat cagacttccc agccttc 47

<210> SEQ ID NO 393
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 393
agacgtgtgc tcttccgatc tggagctctg agacaggaac c 41

<210> SEQ ID NO 394
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 394
agacgtgtgc tcttccgatc ttggcaaagc agaagacaat agtaga 46

<210> SEQ ID NO 395
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 395
agacgtgtgc tcttccgatc tccctttcag ggagtcctgt aca 43

<210> SEQ ID NO 396
<211> LENGTH: 49
<212> TYPE: DNA
<213> ORGANISM: Artificial Sequence
<220> FEATURE:

<223> OTHER INFORMATION: Synthetic polynucleotide

<400> SEQUENCE: 396
agacgtgtgc tcttccgatc tttttcgtta ctgtaaaatg ggaatgttc 49

<210> SEQ ID NO 397
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 397
agacgtgtgc tcttccgatc tcggtgaact ttcgggaaag g 41

<210> SEQ ID NO 398
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 398
agacgtgtgc tcttccgatc tcccacgtac aagaggattt caaagt 46

<210> SEQ ID NO 399
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 399
agacgtgtgc tcttccgatc tagtgtgaat gtacttaatg acacttagc 49

<210> SEQ ID NO 400
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 400
agacgtgtgc tcttccgatc tgtgaggcag gtgctcactt 40

<210> SEQ ID NO 401
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 401
agacgtgtgc tcttccgatc tctggtgttc ttttataccc attttttctt ta 52

<210> SEQ ID NO 402
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 402
agacgtgtgc tcttccgatc tctgttgctc ttgactctga gct 43

<210> SEQ ID NO 403
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 403
agacgtgtgc tcttccgatc tcctcaggtc cttgtggcta ac 42

<210> SEQ ID NO 404
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 404
agacgtgtgc tcttccgatc taggagccgt gggaatcaaa a 41

<210> SEQ ID NO 405
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 405
agacgtgtgc tcttccgatc tcagcatggc aaggcaactt 40

<210> SEQ ID NO 406
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 406
agacgtgtgc tcttccgatc ttgagggaca gaaaatcagg tcg 43

<210> SEQ ID NO 407
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 407
agacgtgtgc tcttccgatc tggctaatga gttgatctct ctgagc 46

<210> SEQ ID NO 408
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 408
agacgtgtgc tcttccgatc taaaagaaaa caaaggacat agattttccc 50

<210> SEQ ID NO 409
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 409
agacgtgtgc tcttccgatc tagagtgctc aaaccttggg aa 42

<210> SEQ ID NO 410
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 410
agacgtgtgc tcttccgatc tgctatcatg ccatgaagaa tattcatata ttcata 56

<210> SEQ ID NO 411
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 411
agacgtgtgc tcttccgatc tagagaaccc acttgggacc a 41

<210> SEQ ID NO 412
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 412
agacgtgtgc tcttccgatc taccatattc ttaattttta aaattcacag cca 53

<210> SEQ ID NO 413
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 413
agacgtgtgc tcttccgatc tctctgtcgt aagtcaagtc tttgtg 46

<210> SEQ ID NO 414
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 414
agacgtgtgc tcttccgatc tctatcgaat cagaatgcaa agcaaatt 48

<210> SEQ ID NO 415
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 415
agacgtgtgc tcttccgatc tcgtttcgga tactcagtct ctgaa 45

<210> SEQ ID NO 416
<211> LENGTH: 50

<212> TYPE: DNA
<213> ORGANISM: Artificial Sequence
<220> FEATURE:
<223> OTHER INFORMATION: Synthetic polynucleotide

<400> SEQUENCE: 416
agacgtgtgc tcttccgatc tacaaattac ctaaactgac tcaagaagaa 50

<210> SEQ ID NO 417
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 417
agacgtgtgc tcttccgatc tggctccttt cgtgagcgaa g 41

<210> SEQ ID NO 418
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 418
agacgtgtgc tcttccgatc tagaggtagt ggaggtcaag gt 42

<210> SEQ ID NO 419
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 419
agacgtgtgc tcttccgatc ttgacttgcg ttcatcttgt tatttaaac 49

<210> SEQ ID NO 420
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 420
agacgtgtgc tcttccgatc tcctgaaaag gtaggttggt gc 42

<210> SEQ ID NO 421
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 421
ggatattcct ttctactctt tgacatcatc ttcacctctt ggttgtgcag g 51

<210> SEQ ID NO 422
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 422
ggatattcct ttctactctt tgacatcatc tcatttaccc ctcacaacaa ccag 54

<210> SEQ ID NO 423
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 423
ggatattcct ttctactctt tgacatcatc tccatgttct aacaccgtga tctg 54

<210> SEQ ID NO 424
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 424
ggatattcct ttctactctt tgacatcatc tcatggaaaa cacttcagtt tgctc 55

<210> SEQ ID NO 425
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 425
ggatattcct ttctactctt tgacatcatc tacagcaaag gttctacccc g 51

<210> SEQ ID NO 426
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 426
ggatattcct ttctactctt tgacatcatc tccaggctac ttcttactca ttccaa 56

<210> SEQ ID NO 427
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 427
ggatattcct ttctactctt tgacatcatc tacctccatc accagctagt ct 52

<210> SEQ ID NO 428
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 428
ggatattcct ttctactctt tgacatcatc tggtgccccc gttttatctg t 51

<210> SEQ ID NO 429
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 429
ggatattcct ttctactctt tgacatcatc tccaagcaaa cccatcctct ctg 53

<210> SEQ ID NO 430
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 430
ggatattcct ttctactctt tgacatcatc taggaggcag gtgttatcat tcc 53

<210> SEQ ID NO 431
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 431
ggatattcct ttctactctt tgacatcatc ttttatctga aattcaaatt taactgggcc 60

<210> SEQ ID NO 432
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 432
ggatattcct ttctactctt tgacatcatc tggagagggt ggaggggct 49

<210> SEQ ID NO 433
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 433
ggatattcct ttctactctt tgacatcatc tggggagctt gcatcctact c 51

<210> SEQ ID NO 434
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 434
ggatattcct ttctactctt tgacatcatc tggctcccct ggtttctcc 49

<210> SEQ ID NO 435
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 435
ggatattcct ttctactctt tgacatcatc tacacccgac cccgcc 46

<210> SEQ ID NO 436
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 436
ggatattcct ttctactctt tgacatcatc ttgttctagg attaaaggag aatgcatg 58

<210> SEQ ID NO 437
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 437
ggatattcct ttctactctt tgacatcatc tccatagaag gctacctccc tct 53

<210> SEQ ID NO 438
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 438
ggatattcct ttctactctt tgacatcatc tggaattaaa atatgaagga gttctgcaag 60

<210> SEQ ID NO 439
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 439
ggatattcct ttctactctt tgacatcatc tttaaaagtt aagacaagac aggttcatac 60
a 61

<210> SEQ ID NO 440
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 440
ggatattcct ttctactctt tgacatcatc tcccaaggac aggcacaact ac 52

<210> SEQ ID NO 441
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 441
ggatattcct ttctactctt tgacatcatc tctcacagca gaaaagccaa tactt 55

<210> SEQ ID NO 442
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 442
ggatattcct ttctactctt tgacatcatc tccgataaac accacaggct cta 53

<210> SEQ ID NO 443
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 443
ggatattcct ttctactctt tgacatcatc tgtcaggcag atgcccagaa g 51

<210> SEQ ID NO 444
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 444
ggatattcct ttctactctt tgacatcatc tctccaagtc atgccacctc a 51

<210> SEQ ID NO 445
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 445
ggatattcct ttctactctt tgacatcatc taggtggaca ggggacatga 50

<210> SEQ ID NO 446
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 446
ggatattcct ttctactctt tgacatcatc tctgaaatag gaacactgcc acc 53

<210> SEQ ID NO 447
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 447
ggatattcct ttctactctt tgacatcatc tcaaagcctc cccctggtta g 51

<210> SEQ ID NO 448
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 448
ggatattcct ttctactctt tgacatcatc ttgtggagtc tgaaactcag cc 52

<210> SEQ ID NO 449
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 449
ggatattcct ttctactctt tgacatcatc tcagggaggg gcatggc 47

<210> SEQ ID NO 450
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 450
ggatattcct ttctactctt tgacatcatc tctgagactc acggctctga c 51

<210> SEQ ID NO 451
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 451
ggatattcct ttctactctt tgacatcatc tctaaattcg gtctcaaaaa caaaacgaa 59

<210> SEQ ID NO 452
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 452
ggatattcct ttctactctt tgacatcatc tccacactga caggggatat agg 53

<210> SEQ ID NO 453
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 453
ggatattcct ttctactctt tgacatcatc tcatacaagt ccttgttcac ggatag 56

<210> SEQ ID NO 454
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 454
ggatattcct ttctactctt tgacatcatc tgaccagcac gttccgagc 49

<210> SEQ ID NO 455
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 455
ggatattcct ttctactctt tgacatcatc tagggaccgc aggggac 47

<210> SEQ ID NO 456
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 456
ggatattcct ttctactctt tgacatcatc tccctagcac agccacagtc 50

<210> SEQ ID NO 457
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 457
ggatattcct ttctactctt tgacatcatc tttttctcat ttagttgtct ttaaattgaa 60
atgc 64

<210> SEQ ID NO 458
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 458
ggatattcct ttctactctt tgacatcatc tggcagccct tgtcatccag 50

<210> SEQ ID NO 459
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 459
ggatattcct ttctactctt tgacatcatc tcaccctgac tctaacttga ccc 53

<210> SEQ ID NO 460
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 460
ggatattcct ttctactctt tgacatcatc tcatgggtac aggaatgtac acct 54

<210> SEQ ID NO 461
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 461
ggatattcct ttctactctt tgacatcatc ttctaaaacc tgccttggct cc 52

<210> SEQ ID NO 462
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 462
ggatattcct ttctactctt tgacatcatc tcagcagtct ccgcatcgt 49

<210> SEQ ID NO 463
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 463
ggatattcct ttctactctt tgacatcatc tcactgtgcc cagcttaatt ttgt 54

<210> SEQ ID NO 464
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 464
ggatattcct ttctactctt tgacatcatc tccctggggt gtcaagtact c 51

<210> SEQ ID NO 465
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 465
ggatattcct ttctactctt tgacatcatc tcataactcc acacatcact ctggt 55

<210> SEQ ID NO 466
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 466
ggatattcct ttctactctt tgacatcatc ttgttcctct tccaacgagg c 51

<210> SEQ ID NO 467
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 467
ggatattcct ttctactctt tgacatcatc tcaggcactc tcggtggatc 50

<210> SEQ ID NO 468
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 468
ggatattcct ttctactctt tgacatcatc tcctaaggtc aaatcctagg gggtaata 58

<210> SEQ ID NO 469
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 469
ggatattcct ttctactctt tgacatcatc tccggggctc tggtcattg 49

<210> SEQ ID NO 470
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 470
ggatattcct ttctactctt tgacatcatc tgttcagcgg gtctccattg t 51

<210> SEQ ID NO 471
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 471
ggatattcct ttctactctt tgacatcatc ttgaagacct cacagtaaaa ataggtgatt 60

<210> SEQ ID NO 472
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 472
ggatattcct ttctactctt tgacatcatc ttgtggaaga tccaatccat ttttgttg 58

<210> SEQ ID NO 473
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 473
ggatattcct ttctactctt tgacatcatc tgagggtctg acgggtagag t 51

<210> SEQ ID NO 474
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 474
ggatattcct ttctactctt tgacatcatc tacagcacat gacggaggtt g 51

<210> SEQ ID NO 475

<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 475
ggatattcct ttctactctt tgacatcatc tttataaggc ctgctgaaaa tgactgaa 58

<210> SEQ ID NO 476
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 476
ggatattcct ttctactctt tgacatcatc tgaccccagt tgcaaaccag ac 52

<210> SEQ ID NO 477
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 477
ggatattcct ttctactctt tgacatcatc ttctgattcc tcactgattg ctcttag 57

<210> SEQ ID NO 478
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 478
ggatattcct ttctactctt tgacatcatc tcgggggctc agcatcca 48

<210> SEQ ID NO 479
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 479
ggatattcct ttctactctt tgacatcatc tcaaacagta gcttccctgg gt 52

<210> SEQ ID NO 480
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 480
ggatattcct ttctactctt tgacatcatc tcaggactcg gtggatatgg tc 52

<210> SEQ ID NO 481
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 481
ggatattcct ttctactctt tgacatcatc tggcgcatgt aggcggtg 48

<210> SEQ ID NO 482
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 482
ggatattcct ttctactctt tgacatcatc tggagatgtg gtcaatggaa gaaac 55

<210> SEQ ID NO 483
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 483
ggatattcct ttctactctt tgacatcatc ttcgtgttgg caacatacca tct 53

<210> SEQ ID NO 484
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 484
ggatattcct ttctactctt tgacatcatc tcttctaaca gctacccttc catcat 56

<210> SEQ ID NO 485
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 485
ggatattcct ttctactctt tgacatcatc taggaaagtt ctgctgtttt tagcaaa 57

<210> SEQ ID NO 486
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 486
ggatattcct ttctactctt tgacatcatc tctcagtatt tgcagaatac attcaaggt 59

<210> SEQ ID NO 487
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 487
ggatattcct ttctactctt tgacatcatc tgaagagtaa caagccaaat gaacaga 57

<210> SEQ ID NO 488
<211> LENGTH: 58
<212> TYPE: DNA

<213> ORGANISM: Artificial Sequence
<220> FEATURE:
<223> OTHER INFORMATION: Synthetic polynucleotide

<400> SEQUENCE: 488
ggatattcct ttctactctt tgacatcatc tttgatagtt gttctagcag tgaagaga 58

<210> SEQ ID NO 489
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 489
ggatattcct ttctactctt tgacatcatc tacaattcaa aagcacctaa aaagaatagg 60

<210> SEQ ID NO 490
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 490
ggatattcct ttctactctt tgacatcatc tacagaaaaa aaggtagatc tgaatgct 58

<210> SEQ ID NO 491
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 491
ggatattcct ttctactctt tgacatcatc taggatctga ttcttctgaa gataccg 57

<210> SEQ ID NO 492
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 492
ggatattcct ttctactctt tgacatcatc ttggatttat ctgctcttcg cgt 53

<210> SEQ ID NO 493
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 493
ggatattcct ttctactctt tgacatcatc tgtatctaca actgtttcat atacttcatc 60
ttct 64

<210> SEQ ID NO 494
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 494
ggatattcct ttctactctt tgacatcatc tcaggccaaa gacggtacaa ct 52

<210> SEQ ID NO 495
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 495
ggatattcct ttctactctt tgacatcatc tctcttcttt ttccaattct tgaatttgac 60
a 61

<210> SEQ ID NO 496
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 496
ggatattcct ttctactctt tgacatcatc tgcagtttca ggacatccat tttatcaa 58

<210> SEQ ID NO 497
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 497
ggatattcct ttctactctt tgacatcatc tccaagttaa tattcctaac acactgttca 60

<210> SEQ ID NO 498
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 498
ggatattcct ttctactctt tgacatcatc taataaggct tctagtctct tttgttgg 58

<210> SEQ ID NO 499
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 499
ggatattcct ttctactctt tgacatcatc tacaagcact tatcaaaact gaaaaattac 60
aat 63

<210> SEQ ID NO 500
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 500
ggatattcct ttctactctt tgacatcatc tggcttaata atgtcctcat taaggtctat 60
c 61

<210> SEQ ID NO 501
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 501
ggatattcct ttctactctt tgacatcatc tcaatgcaag ttcttcgtca gcta 54

<210> SEQ ID NO 502
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 502
ggatattcct ttctactctt tgacatcatc ttttaaacta tttctaacaa cgccttctct 60

<210> SEQ ID NO 503
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 503
ggatattcct ttctactctt tgacatcatc ttcaacatcc cacctcccat cta 53

<210> SEQ ID NO 504
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 504
ggatattcct ttctactctt tgacatcatc tgaatcatat ttgtgtctga tgggcaat 58

<210> SEQ ID NO 505
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 505
ggatattcct ttctactctt tgacatcatc taaaccatgt gaaaatcaca gattttgg 58

<210> SEQ ID NO 506
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 506
ggatattcct ttctactctt tgacatcatc tcagagaatc tccattttag cacttacc 58

<210> SEQ ID NO 507
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 507
ggatattcct ttctactctt tgacatcatc ttgaatatca ttaaggaact tgatattttt 60
cagg 64

<210> SEQ ID NO 508
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 508
ggatattcct ttctactctt tgacatcatc taaatttgag ttgaaatcat ggtattgcat 60

<210> SEQ ID NO 509
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 509
ggatattcct ttctactctt tgacatcatc tcacagcacc caatcaagct c 51

<210> SEQ ID NO 510
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 510
ggatattcct ttctactctt tgacatcatc tgacaacact cttcagcaca atcaa 55

<210> SEQ ID NO 511
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 511
ggatattcct ttctactctt tgacatcatc tagggcatca cctctctaca gtt 53

<210> SEQ ID NO 512
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 512
ggatattcct ttctactctt tgacatcatc tgtttgctga atgttaacat taatgcttat 60
tt 62

<210> SEQ ID NO 513
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 513
ggatattcct ttctactctt tgacatcatc tacggacctt acgtcagtga ct 52

<210> SEQ ID NO 514
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 514
ggatattcct ttctactctt tgacatcatc tggctacgtg ttagtggctc tta 53

<210> SEQ ID NO 515
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 515
ggatattcct ttctactctt tgacatcatc tacggagaat aaactgagct ctctc 55

<210> SEQ ID NO 516
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 516
ggatattcct ttctactctt tgacatcatc tccaaaaaat gaagccggcg a 51

<210> SEQ ID NO 517
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 517
ggatattcct ttctactctt tgacatcatc ttgcctactg gttcaattac ttttaaaaag 60

<210> SEQ ID NO 518
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 518
ggatattcct ttctactctt tgacatcatc tcatcagcat ttgactttac cttatcaatg 60

<210> SEQ ID NO 519
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 519
ggatattcct ttctactctt tgacatcatc tctagagtgt ctgtgtaatc aaacaagttt 60

<210> SEQ ID NO 520
<211> LENGTH: 56

<212> TYPE: DNA
<213> ORGANISM: Artificial Sequence
<220> FEATURE:
<223> OTHER INFORMATION: Synthetic polynucleotide

<400> SEQUENCE: 520
ggatattcct ttctactctt tgacatcatc ttgatccagt aacaccaata gggttc 56

<210> SEQ ID NO 521
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 521
ggatattcct ttctactctt tgacatcatc tagtgaaaag agtctcaaac acaaactag 59

<210> SEQ ID NO 522
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 522
ggatattcct ttctactctt tgacatcatc ttttttttcca gtttattgta tttgcatagc 60
a 61

<210> SEQ ID NO 523
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 523
ggatattcct ttctactctt tgacatcatc tccttataca ccgtgccgaa cg 52

<210> SEQ ID NO 524
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 524
ggatattcct ttctactctt tgacatcatc tcacagcaaa gcagaaactc aca 53

<210> SEQ ID NO 525
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 525
ggatattcct ttctactctt tgacatcatc tccctccctc caggaagcct a 51

<210> SEQ ID NO 526
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 526
ggatattcct ttctactctt tgacatcatc tggagccaat attgtctttg tgttcc 56

<210> SEQ ID NO 527
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 527
ggatattcct ttctactctt tgacatcatc tctccttctg catggtattc tttctc 56

<210> SEQ ID NO 528
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 528
ggatattcct ttctactctt tgacatcatc ttgatgggca gattacagtg gg 52

<210> SEQ ID NO 529
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 529
ggatattcct ttctactctt tgacatcatc ttggatacag gtcaagtcta agtcg 55

<210> SEQ ID NO 530
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 530
ggatattcct ttctactctt tgacatcatc tcaatattgt tcctgtatac gccttca 57

<210> SEQ ID NO 531
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 531
ggatattcct ttctactctt tgacatcatc tttgcaagca tacaaataag aaaacatact 60
t 61

<210> SEQ ID NO 532
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 532
ggatattcct ttctactctt tgacatcatc ttcataccta cctctgcaat taaatttgg 59

<210> SEQ ID NO 533
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 533
ggatattcct ttctactctt tgacatcatc tccccgatgt aataaatatg cacatatca 59

<210> SEQ ID NO 534
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 534
ggatattcct ttctactctt tgacatcatc ttgttttcca ataaattctc agatccagg 59

<210> SEQ ID NO 535
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 535
ggatattcct ttctactctt tgacatcatc ttggatattt ctcccaatga aagtaaagta 60
c 61

<210> SEQ ID NO 536
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 536
ggatattcct ttctactctt tgacatcatc ttgctatcga tttcttgatc acatagact 59

<210> SEQ ID NO 537
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 537
ggatattcct ttctactctt tgacatcatc tcgtgggcgt gagcgc 46

<210> SEQ ID NO 538
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 538
ggatattcct ttctactctt tgacatcatc tctgacctta aaatttggag aaaagtatcg 60

<210> SEQ ID NO 539
<211> LENGTH: 57
<212> TYPE: DNA
<213> ORGANISM: Artificial Sequence
<220> FEATURE:

<223> OTHER INFORMATION: Synthetic polynucleotide

<400> SEQUENCE: 539
ggatattcct ttctactctt tgacatcatc tcatctggtg ttacagaagt tgaactg 57

<210> SEQ ID NO 540
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 540
ggatattcct ttctactctt tgacatcatc tcgaagatgg caaacttccc atc 53

<210> SEQ ID NO 541
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 541
ggatattcct ttctactctt tgacatcatc tctcagacac ttacggggac ag 52

<210> SEQ ID NO 542
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 542
ggatattcct ttctactctt tgacatcatc tgacaggccc tgacacagg 49

<210> SEQ ID NO 543
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 543
ggatattcct ttctactctt tgacatcatc tatctctaac ccattgaggc cg 52

<210> SEQ ID NO 544
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 544
ggatattcct ttctactctt tgacatcatc tacacttgac catcaccatg tagac 55

<210> SEQ ID NO 545
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 545
ggatattcct ttctactctt tgacatcatc ttacaagctg tctctctccc agt 53

<210> SEQ ID NO 546
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 546
ggatattcct ttctactctt tgacatcatc tccagcccat ggcaaacac 49

<210> SEQ ID NO 547
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 547
ggatattcct ttctactctt tgacatcatc tcgctcacca tgtgtgactt gat 53

<210> SEQ ID NO 548
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 548
ggatattcct ttctactctt tgacatcatc ttcctatcct gagtagtggt aatctact 58

<210> SEQ ID NO 549
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 549
ggatattcct ttctactctt tgacatcatc ttctgactgt accaccatcc act 53

<210> SEQ ID NO 550
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 550
ggatattcct ttctactctt tgacatcatc tagtaacagt aggtgtttca atatgacttt 60
t 61

<210> SEQ ID NO 551
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 551
ggatattcct ttctactctt tgacatcatc tccctccagg agcccacc 48

<210> SEQ ID NO 552
<211> LENGTH: 55
<212> TYPE: DNA
<213> ORGANISM: Artificial Sequence
<220> FEATURE:

<223> OTHER INFORMATION: Synthetic polynucleotide

<400> SEQUENCE: 552
ggatattcct ttctactctt tgacatcatc tactgctact acataccagg ttctg 55

<210> SEQ ID NO 553
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 553
ggatattcct ttctactctt tgacatcatc tctgatcaag gcaccgctct aa 52

<210> SEQ ID NO 554
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 554
ggatattcct ttctactctt tgacatcatc tctccatccc ggtgtgcat 49

<210> SEQ ID NO 555
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 555
ggatattcct ttctactctt tgacatcatc ttcaagggct atgggggctt 50

<210> SEQ ID NO 556
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 556
ggatattcct ttctactctt tgacatcatc tagatgtgcc ctgacatcag aaata 55

<210> SEQ ID NO 557
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 557
ggatattcct ttctactctt tgacatcatc ttcacttaac cttcagtgtt gatctga 57

<210> SEQ ID NO 558
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 558
ggatattcct ttctactctt tgacatcatc taggagtggg accatgtttg g 51

<210> SEQ ID NO 559
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 559
ggatattcct ttctactctt tgacatcatc tccatcgctc ccatcattgc t 51

<210> SEQ ID NO 560
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 560
ggatattcct ttctactctt tgacatcatc tctttcaaac acgtgtgatc aatagtac 58

<210> SEQ ID NO 561
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 561
ggatattcct ttctactctt tgacatcatc tcattctcat atcagaactt aaatacatag 60
cag 63

<210> SEQ ID NO 562
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 562
ggatattcct ttctactctt tgacatcatc tacaagtcca tcttataggg gaagga 56

<210> SEQ ID NO 563
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 563
ggatattcct ttctactctt tgacatcatc taaatgcatg agcatgcgca a 51

<210> SEQ ID NO 564
<211> LENGTH: 62
<212> TYPE: DNA
<213> ORGANISM: Artificial Sequence
<220> FEATURE:
<223> OTHER INFORMATION: Synthetic polynucleotide

<400> SEQUENCE: 564
ggatattcct ttctactctt tgacatcatc tccacgataa aattctctta tcttgaagga 60
tt 62

<210> SEQ ID NO 565
<211> LENGTH: 66
<212> TYPE: DNA

<213> ORGANISM: Artificial Sequence
<220> FEATURE:
<223> OTHER INFORMATION: Synthetic polynucleotide

<400> SEQUENCE: 565
ggatattcct ttctactctt tgacatcatc tgttcaaagt gtttctgata ttgaaaaatt 60
ttaagt 66

<210> SEQ ID NO 566
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 566
ggatattcct ttctactctt tgacatcatc tcctttttca tccttcgcac atgtata 57

<210> SEQ ID NO 567
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 567
ggatattcct ttctactctt tgacatcatc tccctggagc agatgactca ca 52

<210> SEQ ID NO 568
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 568
ggatattcct ttctactctt tgacatcatc taggcagggg gcttggt 47

<210> SEQ ID NO 569
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 569
ggatattcct ttctactctt tgacatcatc tcacaccttt tttaacaacc ggatct 56

<210> SEQ ID NO 570
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 570
ggatattcct ttctactctt tgacatcatc taggtgaggc cctgtaatct gta 53

<210> SEQ ID NO 571
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 571
ggatattcct ttctactctt tgacatcatc taccttaata tcagacttcc cagcc 55

<210> SEQ ID NO 572
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 572
ggatattcct ttctactctt tgacatcatc tttttgggag ctctgagaca gg 52

<210> SEQ ID NO 573
<211> LENGTH: 55
<212> TYPE: DNA
<213> ORGANISM: Artificial Sequence
<220> FEATURE:
<223> OTHER INFORMATION: Synthetic polynucleotide

<400> SEQUENCE: 573
ggatattcct ttctactctt tgacatcatc tctgatggca aagcagaaga caata 55

<210> SEQ ID NO 574
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 574
ggatattcct ttctactctt tgacatcatc tagccctttc agggagtcct 50

<210> SEQ ID NO 575
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 575
ggatattcct ttctactctt tgacatcatc ttctcttaat ctcagttttc gttactgtaa 60
aat 63

<210> SEQ ID NO 576
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 576
ggatattcct ttctactctt tgacatcatc tcatagcacc actcggtgaa ctt 53

<210> SEQ ID NO 577
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 577
ggatattcct ttctactctt tgacatcatc taggagtgag aacccacgta ca 52

<210> SEQ ID NO 578

<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 578
ggatattcct ttctactctt tgacatcatc tcaacagtgt gaatgtactt aatgacact 59

<210> SEQ ID NO 579
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 579
ggatattcct ttctactctt tgacatcatc tcctgtcctg tgaggcagg 49

<210> SEQ ID NO 580
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 580
ggatattcct ttctactctt tgacatcatc ttgccctgct ggtgttcttt tata 54

<210> SEQ ID NO 581
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 581
ggatattcct ttctactctt tgacatcatc ttcgctgctg ctgttgct 48

<210> SEQ ID NO 582
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 582
ggatattcct ttctactctt tgacatcatc tgggtcctca ggtccttgtg 50

<210> SEQ ID NO 583
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 583
ggatattcct ttctactctt tgacatcatc tgcgttggga acttcaactg g 51

<210> SEQ ID NO 584
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 584
ggatattcct ttctactctt tgacatcatc tttgtagccc agcatggcaa 50

<210> SEQ ID NO 585
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 585
ggatattcct ttctactctt tgacatcatc ttttgctttt gagggacaga aaatca 56

<210> SEQ ID NO 586
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 586
ggatattcct ttctactctt tgacatcatc tacttggcta atgagttgat ctctct 56

<210> SEQ ID NO 587
<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 587
ggatattcct ttctactctt tgacatcatc tagttatttt caaaagaaaa caaaggacat 60
agatt 65

<210> SEQ ID NO 588
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 588
ggatattcct ttctactctt tgacatcatc tgcaaagagt gctcaaacct tgg 53

<210> SEQ ID NO 589
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 589
ggatattcct ttctactctt tgacatcatc tgttactaat ttttttggct atcatgcca 59

<210> SEQ ID NO 590
<211> LENGTH: 52
<212> TYPE: DNA
<213> ORGANISM: Artificial Sequence
<220> FEATURE:
<223> OTHER INFORMATION: Synthetic polynucleotide

<400> SEQUENCE: 590
ggatattcct ttctactctt tgacatcatc tgtagcagag aacccacttg gg 52

<210> SEQ ID NO 591

<211> LENGTH: 65
<212> TYPE: DNA
<213> ORGANISM: Artificial Sequence
<220> FEATURE:
<223> OTHER INFORMATION: Synthetic polynucleotide

<400> SEQUENCE: 591
ggatattcct ttctactctt tgacatcatc tagctcaaac catattctta atttttaaaa 60
ttcac 65

<210> SEQ ID NO 592
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 592
ggatattcct ttctactctt tgacatcatc tctcctctgt cgtaagtcaa gtcttt 56

<210> SEQ ID NO 593
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 593
ggatattcct ttctactctt tgacatcatc tcagtctggt aaagtgctat cgaatc 56

<210> SEQ ID NO 594
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 594
ggatattcct ttctactctt tgacatcatc tctgaatagt ccgtttcgga tactca 56

<210> SEQ ID NO 595
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 595
ggatattcct ttctactctt tgacatcatc taaaaacaca aattacctaa actgactcaa 60
g 61

<210> SEQ ID NO 596
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 596
ggatattcct ttctactctt tgacatcatc tagcgcctcc cggct 45

<210> SEQ ID NO 597
<211> LENGTH: 51
<212> TYPE: DNA
<213> ORGANISM: Artificial Sequence

```
<220> FEATURE:
<223> OTHER INFORMATION: Synthetic polynucleotide

<400> SEQUENCE: 597

ggatattcct ttctactctt tgacatcatc ttgccagagg tagtggaggt c            51


<210> SEQ ID NO 598
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 598

ggatattcct ttctactctt tgacatcatc tagtgacttg cgttcatctt gttattta      58


<210> SEQ ID NO 599
<211> LENGTH: 53
<212> TYPE: DNA
<213> ORGANISM: Artificial Sequence
<220> FEATURE:
<223> OTHER INFORMATION: Synthetic polynucleotide

<400> SEQUENCE: 599

ggatattcct ttctactctt tgacatcatc tggagcctga aaaggtaggt tgg          53
```

QUANTITATIVE AMPLICON SEQUENCING FOR MULTIPLEXED COPY NUMBER VARIATION DETECTION AND ALLELE RATIO QUANTITATION

REFERENCE TO RELATED APPLICATIONS

The present application is a national phase application under 35 U.S.C. § 371 of International Application No. PCT/US2020/012089, filed Jan. 2, 2020, which claims the priority benefit of U.S. provisional application No. 62/788,375, filed Jan. 4, 2019, the entire contents of which is incorporated herein by reference.

STATEMENT REGARDING FEDERALLY SPONSORED RESEARCH

This invention was made with government support under Grant No. R01 HG008752 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Nov. 26, 2019, is named RICEP0058WO_ST25.txt and is 145.6 kilobytes in size.

BACKGROUND

1. Field

The present invention relates generally to the fields of molecular biology and medicine. More particularly, it concerns compositions and methods for multiplexed copy number variation detection and allele ration quantitation using quantitative amplicon sequencing.

2. Description of Related Art

Copy number variations (CNVs) are important cancer biomarkers contributing to cancer formation and progression. They are present in a significant percentage of tumors, between 3% and 98% depending on the cancer type. Many CNVs confer sensitivity or resistance to targeted therapies, for example, MET amplification confers increased sensitivity to MET TKIs in non-small cell lung cancer, and PTEN deletion confers BRAF inhibitor resistance in melanoma. In tumor samples, CNV of a specific gene may exist only in a small fraction (<10%) of cells, due to tumor heterogeneity and normal cell contamination.

Unlike mutations and indels, CNVs have no unique sequence, thus detection of CNV requires accurate quantitation. This quantitation is difficult due to stochasticity in sampling of DNA molecules. For example, the standard deviation (a) of sampling 1200 molecules per locus (i.e. 1200 haploid genomic copies from 600 normal cells, 4 ng of genomic DNA) can be estimated by Poisson distribution $$\sigma = \sqrt{1200} = 35,$$

corresponding to 3% of molecule number. In this case, detecting 1% of extra copies is not possible. Theoretically, increasing the number of input molecules or analyzing more loci can equally decrease the variance, and the σ can be estimated as $$\sigma = \sqrt{\text{haploid genomic copies} \times \text{loci number}}.$$

If genomic copy number or loci number increase by 100×, σ will be decreased to 0.3%, and 1% of extra copies will be detectable.

Current standard method for CNV detection in molecular diagnostics is in situ hybridization (ISH), which can determine CNV status based on observation of a small number of cells. However, ISH technologies lack the ability to perform simultaneous analysis of multiple genomic regions, due to the limited number of distinguishable colors in both fluorescence and bright-field microscopy. Additionally, ISH is a complex process that needs to be performed by specialized labs, preventing it from being widely adopted.

Another method for CNV detection is droplet digital PCR (ddPCR), which is a PCR-based method for absolute quantitation of DNA molecules. However, its limit of detection (LoD) for CNV is about 20% extra copies with a large number of replicated experiments. Like ISH, ddPCR also suffers from an inability to be multiplexed due to the limited number of fluorescence channels. Microarray-based methods, including array comparative genomic hybridization and SNP arrays, are highly multiplexed methods used for screening of large CNVs and aneuploidies. However, they are not as good in detecting smaller CNVs<40 kb or low-frequency CNVs at <30% extra copies.

Next-generation sequencing (NGS) is a high-throughput technology that has seen rapidly decreasing costs over the past decade. NGS is popular in the field of cancer molecular diagnostics. Highly multiplexed mutation detection with an LoD of <0.1% variant allele frequency has been achieved and commercialized on NGS platforms. However, current LoD of NGS methods for CNV detection is not as good: whole-exome sequencing (WES) has been used for CNV discovery at a level of ≈30% extra copies, but is expensive, and requires even more NGS reads (with a proportional increase in cost) to achieve lower LoD. Smaller hybrid-capture panels, such as the FoundationOne commercial panel, can reach an LoD of ≈30% extra copies at lower costs.

In NGS panels for diagnostics, target enrichment is needed to reduce NGS reads wasted on unrelated genomic regions. Two popular methods for target enrichment are hybrid-capture and multiplexed PCR. Current NGS-based CNV panels are mostly hybrid-capture-based, which means target regions are captured by biotinylated nucleic acid probes and separated from the rest of the genome using streptavidin magnetic beads. Hybrid-capture panels have low on-target rates when the panel size is small, so most panels are >100 kb (i.e. >1000 probes or loci); this is due to nonspecific binding of unwanted DNA on bead surfaces, probes, and captured targets. Due to the large number of loci, the coverage of hybrid-capture panels is not uniform: the 95% and 5% percentile loci differ by at least 30-fold, which introduces another layer of bias in quantitation. Hybrid-capture panels also suffer from low conversion rates (i.e., the percentage of input molecules sequenced) caused by imperfect end-repair and ligation, causing biased sampling processing and contributing to variation.

SUMMARY

Provided herein are methods of quantitative amplicon sequencing, for labeling each strand of targeted genomic loci in a DNA sample with an oligonucleotide barcode sequence by polymerase chain reaction, and amplifying the genomic region(s) for high-throughput sequencing. The methods can be used for the simultaneous detection of copy number variation (CNV) in a set of genes of interest, by quantitating the frequency of extra copies of each gene. In addition, these methods provide for the quantitation of the allele ratio of different genetic identities for targeted genomic loci using multiplexed PCR.

In one embodiment, provided herein are methods for preparing targeted regions of genomic DNA for high-throughput sequencing, the method comprising: (a) obtaining a genomic DNA sample; (b) amplifying at least a portion of the genomic DNA sample by performing two cycles of PCR using: (i) a first oligonucleotide comprising, from 5' to 3', a first region, a second region having a length between 0 and 50 nucleotides (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides), a third region comprising at least four degenerate nucleotides (e.g., 4, 5, 6, 7, 8, 9, 10, 11, or 12 degenerate nucleotides), and a fourth region comprising a sequence that is complementary to a first target genomic DNA region; and (ii) a second oligonucleotide comprising, from 5' to 3', a fifth region, a sixth region having a length between 0 and 50 nucleotides (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides), and a seventh region comprising a sequence that is complementary to a second target genomic DNA region; (c) amplifying a product of step (b) by performing at least three cycles of PCR with an annealing temperature that is 0-10° C. (e.g., 1-10, 2-10, 3-10, 4-10, 5-10, 1-9, 1-8, 1-7, 1-6, 1-5, 2-9, 2-8, 2-7° C. or any range or value derivable therein) higher than an annealing temperature used in step (b) and using: (i) a third oligonucleotide comprising a sequence that is able to hybridize to the reverse complement of at least a portion of the first region; and (ii) a fourth oligonucleotide comprising a sequence that is able to hybridize to the reverse complement of at least a portion of the fifth region; and (d) amplifying a product of step (c) by performing at least one cycle of PCR using a fifth oligonucleotide comprising, from 5' to 3', an eighth region, a ninth region having a length between 0 and 50 nucleotides (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides), and a tenth region comprising a sequence that is complementary to a third target genomic DNA region, wherein the third target genomic DNA region is at least one nucleotide closer to the first target genomic DNA region than the second target genomic DNA region.

In some aspects, methods are methods for preparing between 1 and 10,000 targeted regions (e.g., at least 1, 2, 3, 4, 5, 6, 7, 8, 9, 10, 15, 20, 25, 30, 35, 40, 45, 50, 75, 100, 250, 500, 750, 1,000, 2,000, 3,000, 4,000 or 5,000 and at most 10,000, 9,000, 8,000, 7,000, 6,000, 5,000, 4,000, 3,000, 2,000, 1,000, 750, 500, 250, 100, 75, or 50 targeted regions, or any range or value derivable therein) of genomic DNA for high-throughput sequencing. In some aspects, the third region is a unique molecular identifier (UMI). In some aspects, the third target genomic DNA region is 1-10 (e.g., 1, 2, 3, 4, 5, 6, 7, 8, 9, or 10) bases closer to the first target genomic DNA region than the second target genomic DNA region. In some aspects, the first region and the eighth region are universal primer binding sites. In some aspects, the first region and the eighth region comprise a full or partial NGS adapter sequence. In some aspects, the fifth region comprises a sequence that cannot be found in the human genome. In some aspects, the fifth region comprises a sequence that is different from an NGS adapter sequence. In some aspects, the melting temperatures of the first region and the fifth region are 0-10° C. (e.g., 1-10, 2-10, 3-10, 4-10, 5-10, 1-9, 1-8, 1-7, 1-6, 1-5, 2-9, 2-8, 2-7° C. or any range or value derivable therein) higher than the melting temperatures of the fourth region and the seventh region. In some aspects, the degenerate nucleotides in the third region each independently are one of A, T, or C. In some aspects, none of the degenerate nucleotides in the third region are G. In some aspects, there is a population of first oligonucleotides each having a unique third region.

In some aspects, the methods further comprise purifying the product of step (c). In some aspects, purifying comprises SPRI purification or column purification. In some aspects, the methods further comprise purifying the product of step (d). In some aspects, purifying comprises SPRI purification or column purification. In some aspects, the methods further comprise (e) amplifying the product of step (d) by PCR using primers that hybridize to the first region and the eighth region, wherein the primers comprise an index sequence for next-generation sequencing. In some aspects, the methods further comprise purifying the product of step (e). In some aspects, purifying comprises SPRI purification or column purification. In some aspects, the methods further comprise (f) performing high-throughput DNA sequencing of the produce of step (e). In some aspects, high-throughput DNA sequencing comprises next-generation sequencing.

In some aspects, the first target genomic DNA region and the second target genomic DNA region are on opposite strands of the genomic DNA. In some aspects, the first target genomic DNA region and the second target genomic DNA region are separated by between 40 nucleotides and 500 nucleotides (e.g., by 40, 45, 50, 55, 60, 65, 70, 75, 80, 90, 100, 125, 150, 175, 200, 225, 250, 275, 300, 325, 350, 375, 400, 425, 450, 475, or 500 nucleotides, or any value derivable therein). In some aspects, step (b) comprises an extension time of about 30 minutes (e.g., 27, 28, 29, 30, 31, 32, or 33 minutes). In some aspects, step (c) comprises an extension time of about 30 seconds (e.g., 27, 28, 29, 30, 31, 32, or 33 seconds). In some aspects, step (d) comprises an extension time of about 30 minutes (e.g., 27, 28, 29, 30, 31, 32, or 33 minutes).

In one embodiment, provided herein are methods for quantifying the frequency of extra copies (FEC) of at least one target gene, the method comprising: (a) obtaining a genomic DNA sample; (b) preparing the genomic DNA for high-throughput sequencing according to a method of any one of the present embodiments, wherein the sequences of the fourth region, the seventh region, and the tenth region hybridize to the at least one target gene; (c) performing high-throughput sequencing according to a method of any one of the present embodiments; and (d) calculating the FEC for the at least one target gene based on the sequencing information obtained in step (c).

In some aspects, the methods are methods for quantifying the FEC for a set of target genes, wherein the set of target genes comprises between 2 and 1000 target genes (e.g., at least 2, 3, 4, 5, 6, 7, 8, 9, 10, 15, 20, 25, 30, 35, 40, 45, 50, 75, 100, 250, 500, or 750, and at most 1,000, 900, 800, 750, 700, 650, 600, 550, 500, 450, 400, 350, 300, 250, 200, 150, 100, 75, 50, 25, 20, 15, 10, 9, 8, 7, 6, 5, 4, or 3 targeted regions, or any range or value derivable therein). In some aspects, step (b) is performed using a population of first oligonucleotides, a population of second oligonucleotides, and a population of fifth oligonucleotides, wherein a portion of each of the populations of first, second, and fifth oligonucleotides comprise fourth, seventh, and tenth regions, respectively, that are complementary to one of the set of target genes. In some aspects, each of the fourth, seventh, and tenth regions comprises sequences that are only found once in the human genome. In some aspects, each first oligonucleotide that hybridizes to one target gene has a unique third region compared to each other first oligonucleotide that hybridizes to the same target gene. In some aspects, step (b) is performed using a first oligonucleotide, a second oligonucleotide, and a fifth oligonucleotide comprising fourth, seventh, and tenth regions, respectively, that are complementary to a reference gene. In some aspects, step (b) prepares a portion of each target gene or reference gene for high-throughput sequencing, wherein the portion is between 40 nucleotides and 500 nucleotides (e.g., by 40, 45, 50, 55, 60, 65, 70, 75, 80, 90, 100, 125, 150, 175, 200, 225, 250, 275, 300, 325, 350, 375, 400, 425, 450, 475, or 500 nucleotides, or any value derivable therein) long. In some aspects, FEC is defined as:

$$FEC = \frac{\text{Copies of the target genomic region} - \text{Haploid genomic copies}}{\text{Haploid genomic copies}}.$$

In some aspects, step (d) comprises: (i) aligning NGS reads to the targeted portions of each target gene and grouping the NGS reads into subgroups based on the loci to which they align; (ii) dividing the NGS read at each locus based on their UMI sequences such that all NGS reads carrying the same UMI sequence are grouped as one UMI family; (iii) removing UMI families resulting from PCR errors or NGS errors; (iv) counting the number of unique UMI sequences at each locus; and (v) calculating the FEC based on the number of unique UMI sequences for each locus in each target gene and reference gene. In some aspects, step (d)(iii) comprises removing UMI sequences that do not meet the UMI degenerate base design. In some aspects, step (d)(iii) comprises removing UMI families with a UMI family size less than Fmin, wherein the UMI family size is the number of reads carrying the same UMI, wherein Fmin is between 2 and 20 (e.g., 2, 3, 4, 5, 6, 7, 8, 9, 10, 11, 12, 13, 14, 15, 16, 17, 18, 19, or 20). In some aspects, step (d)(iv) comprises removing UMI sequences that differ by only one or two bases from another UMI sequence with a larger family size.

In some aspects, FEC is defined as:

$$FEC = k\frac{\sum_{i=1}^{u} N_{Tar,i}}{\sum_{j=1}^{w}\sum_{i=1}^{v} N_{Ref,i,j}} - 1, \text{ where } \sum_{i=1}^{u} N_{Tar,i}$$

is the sum UMI number for all or part of the target gene loci, u is the number of loci to consider, u is no more than the total number of loci in the target gene;

$$\sum_{j=1}^{w}\sum_{i=1}^{v} N_{Ref,i,j}$$

is the sum of unique UMI number for all or part of Reference loci, v is the number of loci to consider for one reference, v is no more than the total number of loci in the reference; w is the number of reference to consider, w is no more than the total number of reference; and k is determined by experimental calibration. In some aspects, the FEC is used to identify the copy number variation (CNV) status of the target gene.

In one embodiment, provided herein are methods for quantifying the allele ratio of different genetic identities for an at least one target genomic locus, the method comprising: (a) obtaining a genomic DNA sample; (b) preparing the genomic DNA for high-throughput sequencing according to a method of any one of the present embodiments, wherein the sequences of the fourth region, the seventh region, and the tenth region hybridize to the genomic DNA near the at least one target genomic locus; (c) performing high-throughput sequencing according to a method of any one of the present embodiments; and (d) calculating the allele ratio of different genetic identities for the at least one target genomic locus on the sequencing information obtained in step (c).

In some aspects, the methods are methods for quantifying the allele ratio of different genetic identities for a set of target genomic loci, wherein the set of target genomic loci comprises between 2 and 10,000 target genomic loci (e.g., at least 2, 3, 4, 5, 6, 7, 8, 9, 10, 15, 20, 25, 30, 35, 40, 45, 50, 75, 100, 250, 500, 750, 1,000, 2,000, 3,000, 4,000 or 5,000 and at most 10,000, 9,000, 8,000, 7,000, 6,000, 5,000, 4,000, 3,000, 2,000, 1,000, 750, 500, 250, 100, 75, or 50 target genomic loci, or any range or value derivable therein). In some aspects, step (b) is performed using a population of first oligonucleotides, a population of second oligonucleotides, and a population of fifth oligonucleotides, wherein a portion of each of the populations of first, second, and fifth oligonucleotides comprise fourth, seventh, and tenth regions, respectively, that are complementary to the genomic DNA near the at least one of the set of target genomic loci. In some aspects, each of the fourth, seventh, and tenth regions comprises sequences that are not able to hybridize with non-target regions of the genomic DNA under the conditions of step (b). In some aspects, each first oligonucleotide that hybridizes to the genomic DNA near one target genomic locus has a unique third region compared to each other first oligonucleotide that hybridizes to the genomic DNA near the same target genomic locus. In some aspects, each target genomic locus is between 40 nucleotides and 500 nucleotides (e.g., by 40, 45, 50, 55, 60, 65, 70, 75, 80, 90, 100, 125, 150, 175, 200, 225, 250, 275, 300, 325, 350, 375, 400, 425, 450, 475, or 500 nucleotides, or any value derivable therein) long.

In some aspects, step (d) comprises: (i) aligning NGS reads to the targeted genomic loci and grouping the NGS reads into subgroups based on the loci to which they align; (ii) dividing the NGS read at each locus based on their UMI sequences such that all NGS reads carrying the same UMI sequence are grouped as one UMI family; (iii) removing UMI families resulting from PCR errors or NGS errors; (iv) calling the genetic identity for each remaining UMI family; (v) counting the number of unique UMI sequences at each locus; and (vi) calculating the allele ratio. In some aspects, step (d)(iii) comprises removing UMI sequences that do not meet the UMI degenerate base design. In some aspects, step (d)(iii) comprises removing UMI families with a UMI family size less than Fmin, wherein the UMI family size is the number of reads carrying the same UMI, wherein Fmin is between 2 and 20 (e.g., 2, 3, 4, 5, 6, 7, 8, 9, 10, 11, 12, 13, 14, 15, 16, 17, 18, 19, or 20). In some aspects, step (d)(iii) comprises removing UMI sequences that differ by only one or two bases from another UMI sequence with a larger family size. In some aspects, step (d)(iv) comprises calling the genetic identity only if at least 70% (e.g., 70%, 75%, 80%, 85%, 90%, 95%, or 98%) of the reads in a UMI family are the same on the genetic locus of interest. In some aspects, the allele ratio is defined as $R_{allele}=N_1/N_2$, where $N_1$ is unique UMI number for the first genetic identity, and $N_2$ is unique UMI number for the second genetic identity.

In some aspects, step (d)(iv) comprises identifying the consensus sequence of each UMI family. In some aspects, the consensus sequence is the sequence appearing the highest number of times in the UMI family. In some aspects, step (d)(iv) further comprises comparing the consensus sequence to the wild-type sequence for that locus, thereby identifying mutations in the consensus sequence. In some aspects, the methods further comprise calculating the variant allele frequency (VAF) of the identified mutation. In some aspects, the VAF of the identified mutation is defined as Number of UMI families with the mutation/Total number of UMI families.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Workflow for evaluating the significance of spacer between primer and UMI. Three sets of primers, with no spacer (set 1), with a 5 nt spacer between the forward primer and UMI and a 5 nt spacer between the reverse primer and UMI (set 2), or with a 12 nt spacer between the forward primer and UMI and a 11 nt spacer between the reverse primer and UMI (set 3) were used to amplify input molecules separately. Indices were added before NGS analysis by Illumina MISEQ®. (FIG. 3B) Experimental UMI family size distribution histograms for the three sets of primers. UMI sequences that did not match UMI design pattern were removed.

(FIG. 4A) Data analysis workflow for CNV detection. NGS reads in the FASTQ output file are analyzed to generate CNV status as results. FEC of a target gene will be calculated as $$FEC = k\frac{\sum_{i=1}^{u} N_{Tar,i}}{\sum_{j=1}^{w}\sum_{i=1}^{v} N_{Ref,i,j}} - 1, \text{ where } \sum_{i=1}^{u} N_{Tar,i}$$

is the sum of unique UMI number for all or part of the target gene loci, u is the number of loci to consider;

$$\sum_{j=1}^{w}\sum_{i=1}^{v} N_{Ref,i,j}$$

is the sum of unique UMI number for all or part of Reference loci, v is the number of loci to consider for one reference; w is the number of reference to consider; and k is determined by experimental calibration. CNV status is determined based on FEC. (FIG. 4B) Definition of UMI family size and unique UMI number in data analysis: UMI family size is the number of reads carrying the same UMI sequence, and unique UMI number is the total count of different UMI sequences at one loci.

Figure 5:
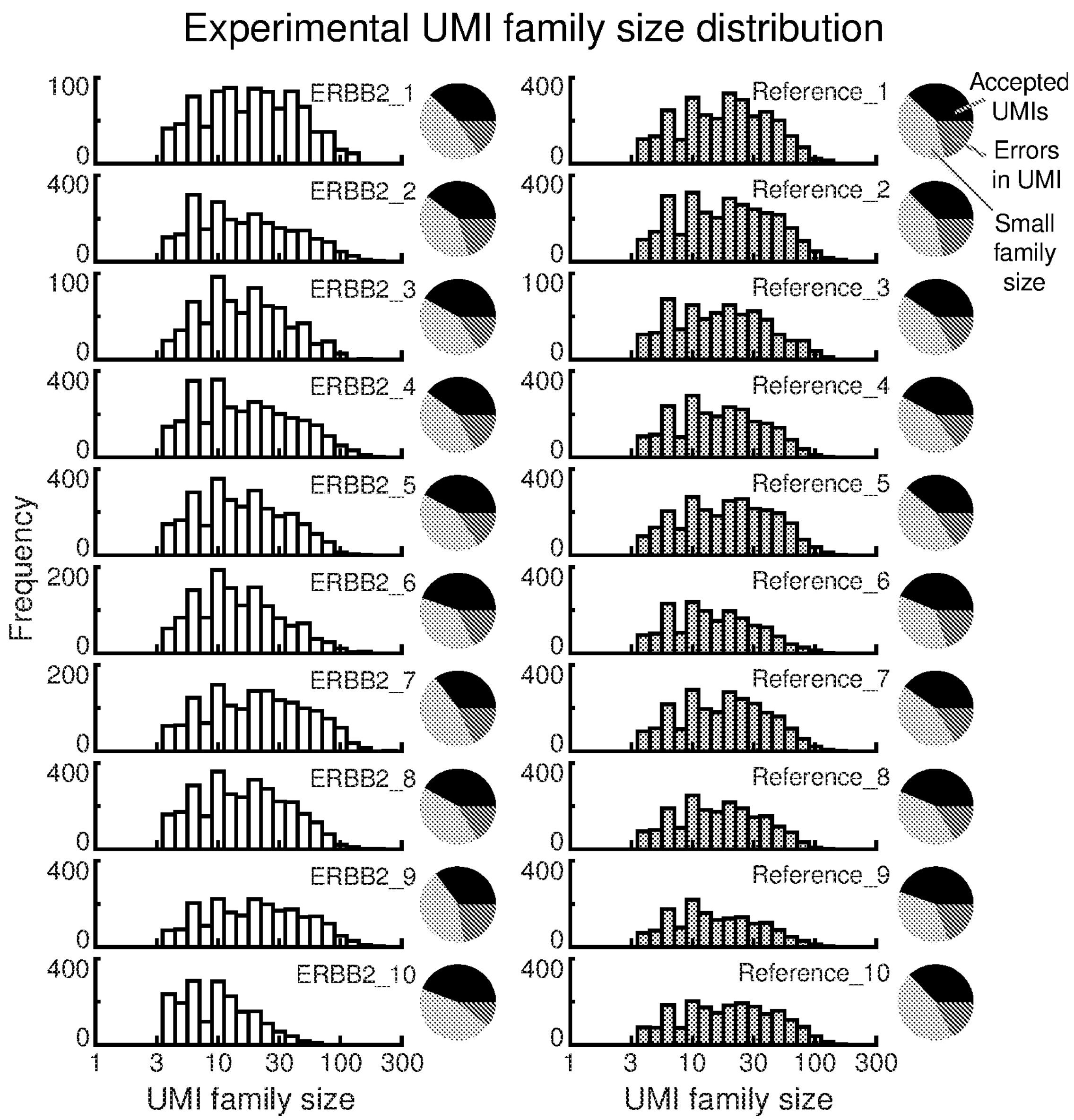

FIG. 5. Example of experimental UMI family size distribution. Example UMI family size distribution of 10 ERBB2 amplicons and 10 Reference amplicons in the same NGS library. We used a normal cell line gDNA NA18562 (purchased from Coriell) as template input for the 20-plex QASeq experiment; input sample contains 2500 haploid genomic copies. The prepared NGS library was sequenced using 1.5 million reads, by Illumina MISEQ® Reagent Kit v3 (150-cycle). The fractions of accepted and discarded UMIs are shown as pie charts. Among all the UMIs, about 20% are discarded due to PCR or sequencing errors (i.e. G bases are found in poly(H) UMIs); about 40% are discarded due to small family size (≤3).

Figure 6:
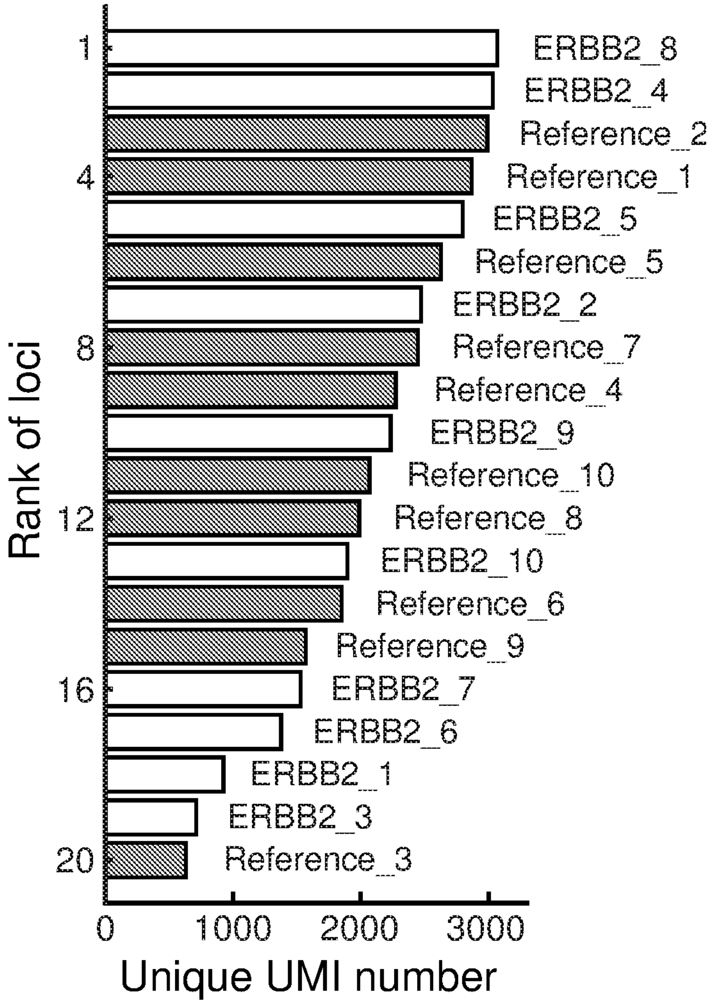

FIG. 6. Example of experimental unique UMI number for different loci. Example unique UMI number of each locus, corresponding to data shown in FIG. 5; white bars are ERBB2 amplicons, and grey bars are Reference amplicons. Input sample contains 2500 haploid genomic copies. The prepared NGS library was sequenced using 1.5 million reads, by Illumina MISEQ® Reagent Kit v3 (150-cycle).

Figure 7:
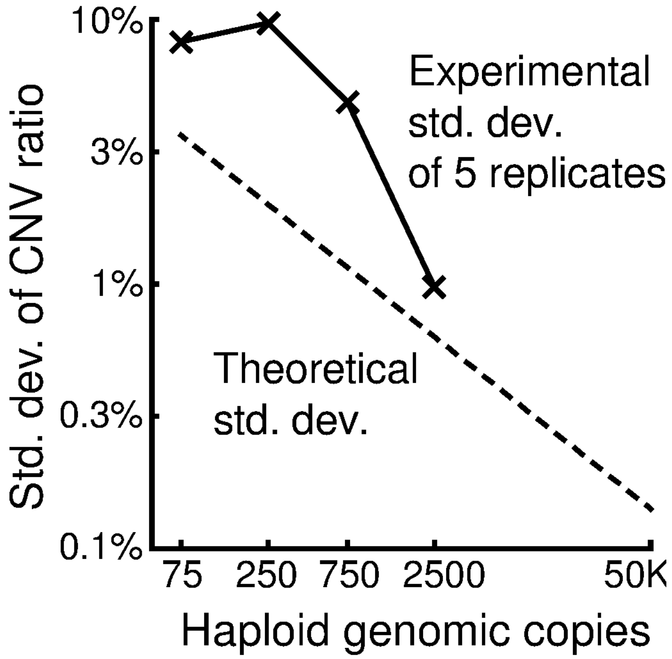

FIG. 7. Experimental calibration results on normal cell line gDNA NA18562 and simulated theoretical standard deviation limit. Standard deviation of CNV ratio ($\sigma_{CNV\ ratio}$) is plotted against input molecule number. LoD can be approximated as $$3\sigma_{CNV\ ratio}.$$

We performed 5 replicated experiments for each different input amount (75, 250, 750, and 2500 haploid genomic copies); experimental results are plotted as cross symbols. A simulation was performed assuming Poisson distribution of sampled molecule number; the simulated $$\sigma_{CNV\ ratio}$$

(plotted as dashed line) is the theoretical lower limit due to stochasticity of sampling.

Figure 8:
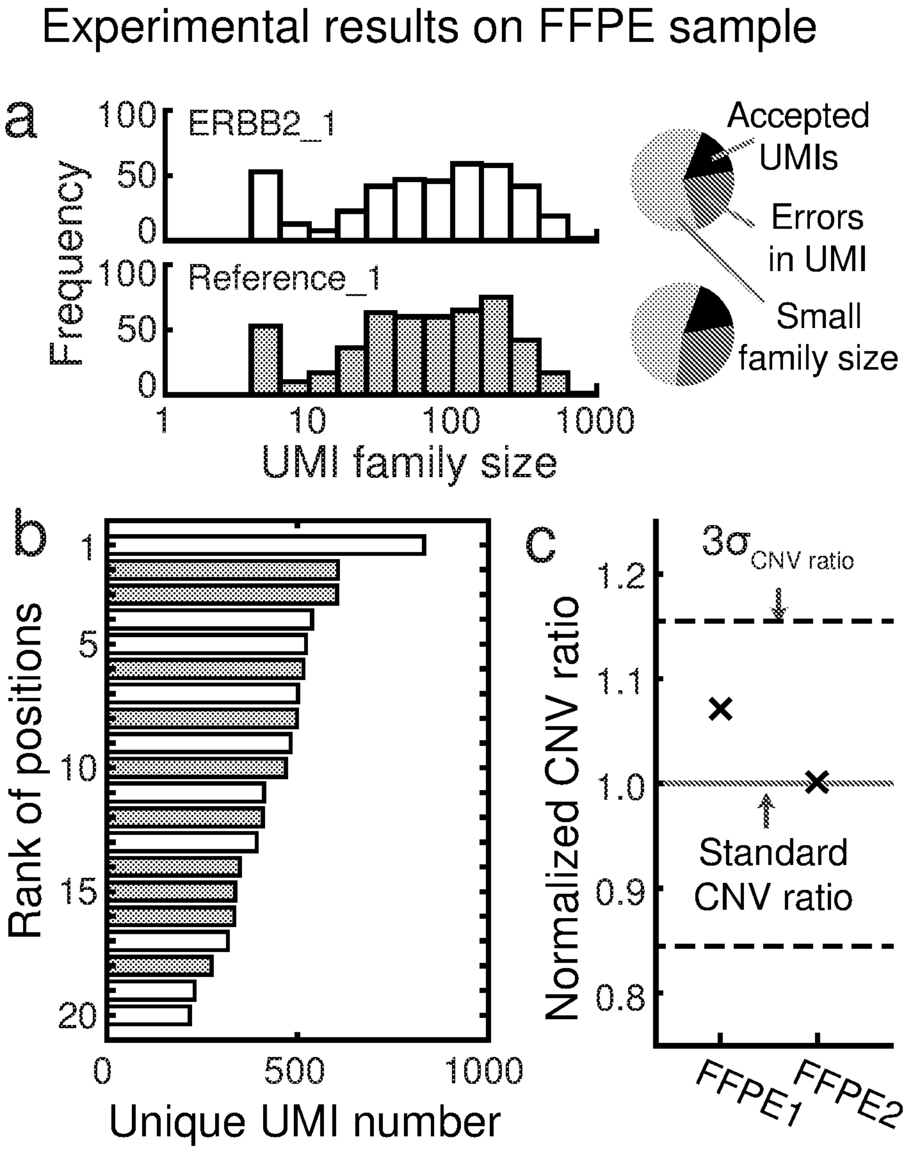

FIGS. 8A-C. Example of experimental results of CNV detection on FFPE samples. We tested 2 lung cancer FFPE slides from the same tumor, in which ERBB2 CNVs are not likely to occur. Input extracted DNA samples contain 2500 haploid genomic copies for each NGS library. The prepared NGS library was sequenced using 1.5 million reads, by Illumina MISEQ® Reagent Kit v3 (150-cycle). (FIG. 8A) Example distribution of UMI family size is plotted for amplicons ERBB2_1 and Reference_1; the fractions of accepted and discarded UMIs are shown as pie charts. (FIG. 8B) Example unique UMI numbers for each amplicon region. White bars are ERBB2 amplicons; grey bars are Reference amplicons. (FIG. 8C) CNV ratios are plotted for 2 FFPE slides from the same lung cancer tumor. CNV of ERBB2 is not detected in these FFPE slides using QASeq based on previous calibration data. Mean and LoD=$3\sigma_{CNV}$ ratio are calculated based on the data of 750-genomic copy input cell line gDNA libraries (see FIG. 7), which have similar unique UMI numbers to the FFPE samples.

FIGS. 9A-E. Primer dimer reduction using primary experimental workflow. (FIG. 9A) The simplest workflow we have tested was a one-pot reaction: after UMI addition, index primers were directly added into the reaction as an open-tube step on the thermocycler, and index PCR (i.e. universal PCR) was performed afterwards. On-target rate was low (0.5%) for this workflow; off-target NGS reads were mostly primer dimers. (FIG. 9B) A SPRI purification step was added after 6 cycles of universal PCR to reduce primer dimer; on-target rate was improved to 20%. (FIG. 9C) A size selection step using agarose gel was added after index PCR to further reduce primer dimer; on-target rate was improved compared to FIG. 9B but still lower than 50%. (FIG. 9D) Primary experimental workflow including both adapter replacement and purification after universal PCR have high average on-target rate of 66%. (FIG. 9E) Source of primer dimers in workflow FIGS. 9A-D.

Figure 10:
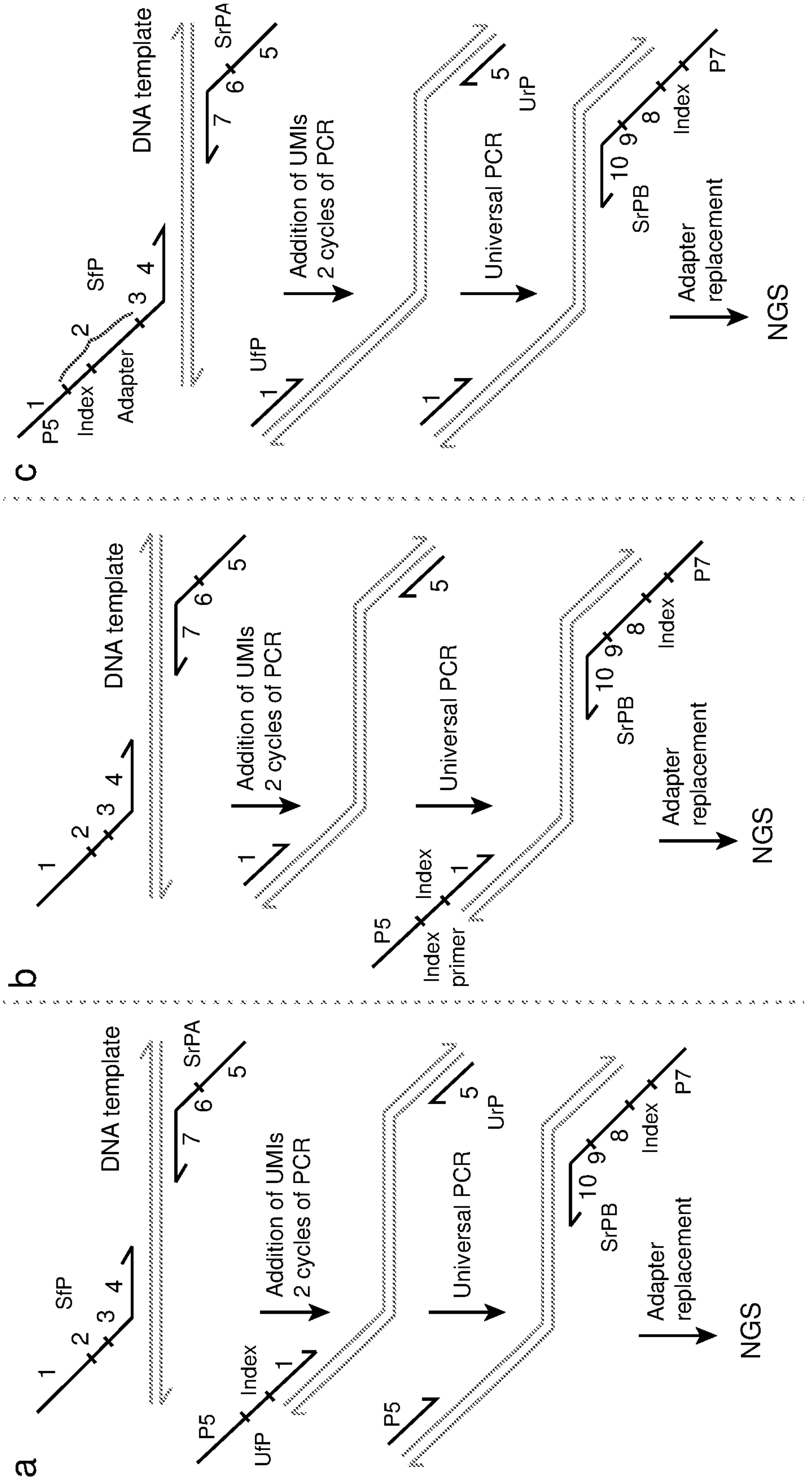

FIGS. 10A-C. Example workflows that do not require NGS index PCR. (FIG. 10A) The index and P5 sequences are added onto the 5' of UfP; the other index and P7 sequences are added onto the 5' of SrPB. The amplicons obtained from adapter replacement contain P5, P7, and dual index, thus are ready for sequencing. (FIG. 10B) The index and P7 sequences are added onto the 5' of SrPB, and the index primer is added together with SrPB in the adapter replacement step. The amplicons are ready for sequencing. (FIG. 10C) The index and P5 sequences are added onto the 5' of SfP; a primer bearing the P5 sequence is used as UfP in the universal PCR step. The other index and P7 sequences are added onto the 5' of SrPB. The amplicons are ready for sequencing.

Figure 11:
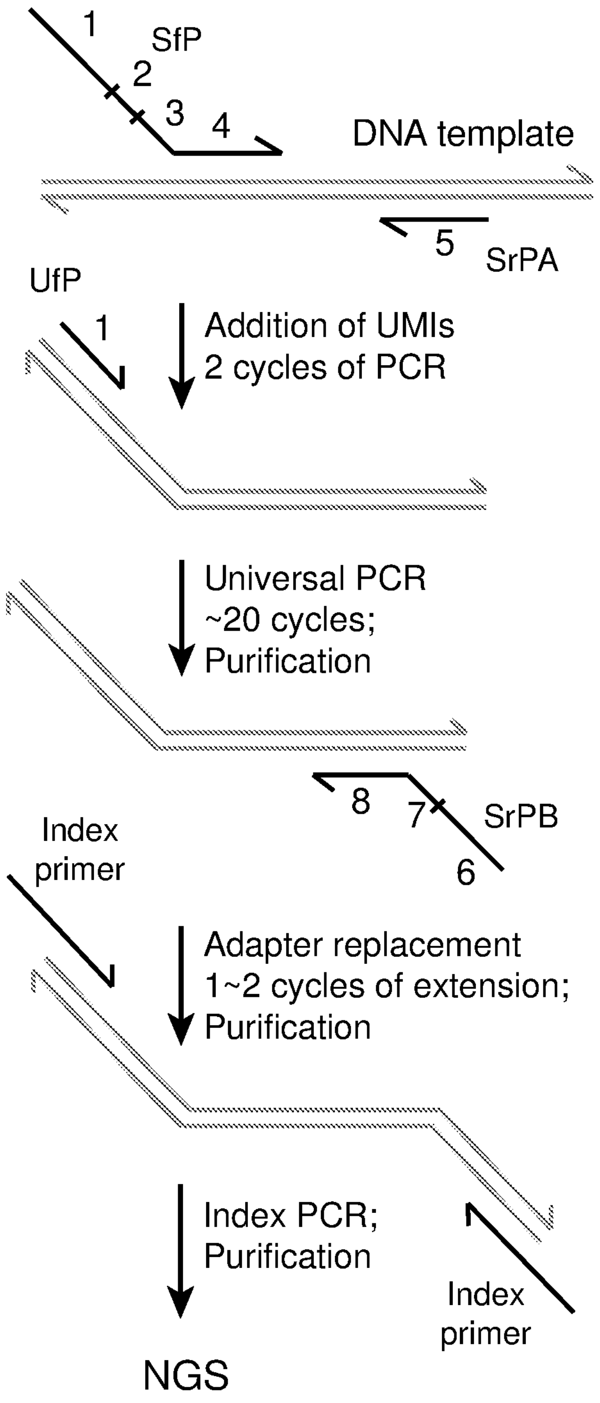

FIG. 11. A variant of QASeq primer design and workflow. Each primer set contains 3 different oligos: a Specific Forward Primer (SfP), a Specific Reverse Primer A (SrPA), and a Specific Reverse Primer B (SrPB). Compared to the original design, SrPA only needs the template-binding region, and Universal Reverse Primer (UrP) is not necessary. Each QASeq panel only needs one Universal Forward Primer (UfP); there can be additional bases at 5'-end of region 1 in UfP. Compared to the original experimental workflow, more cycles of PCR are needed in the universal PCR step; ≥10 cycles are recommended.

Figure 12:
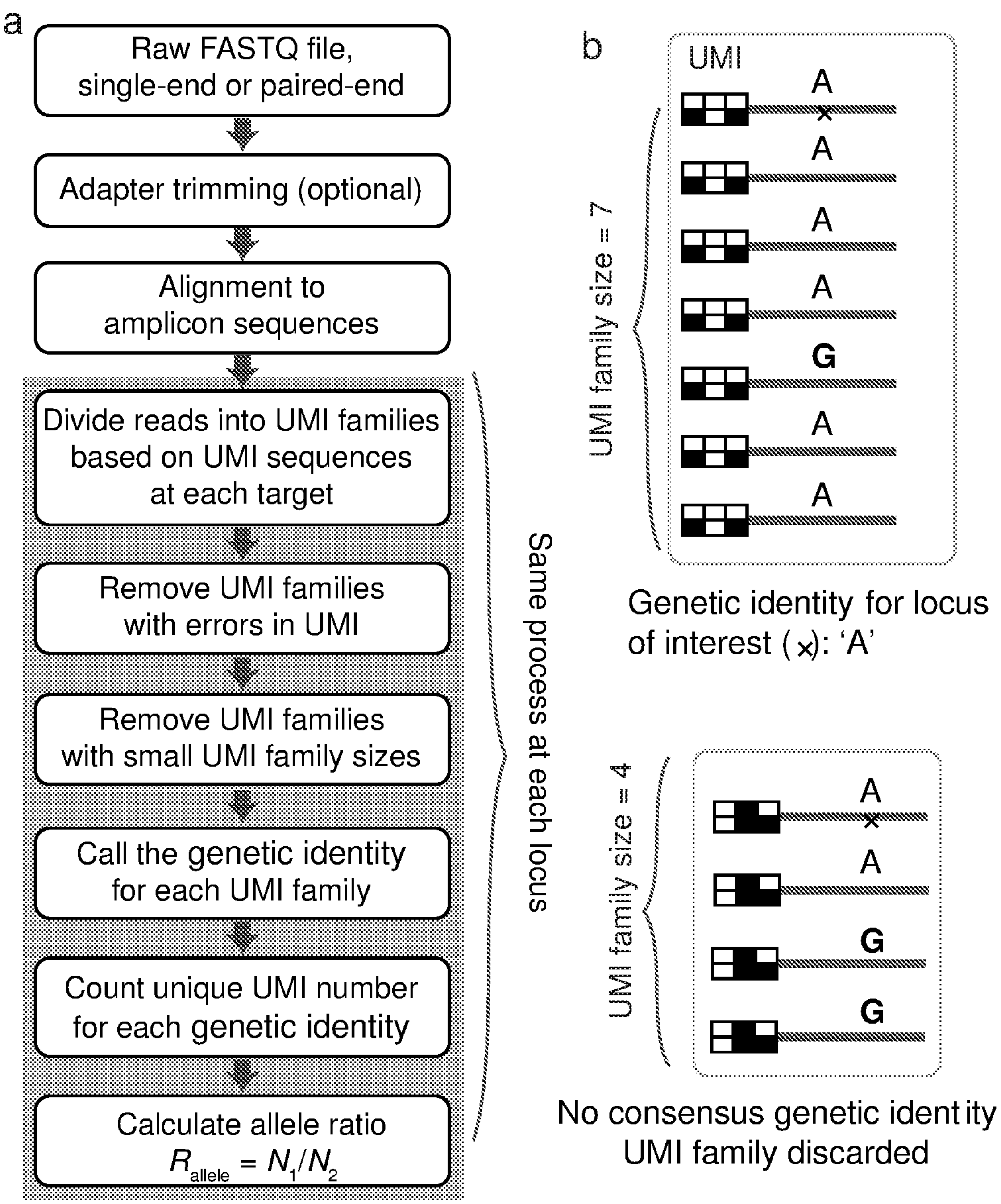

FIGS. 12A-B. Data analysis for QASeq-based allele ratio quantitation. (FIG. 12A) Data analysis workflow for allele ratio quantitation. NGS reads in the FASTQ output file are analyzed to generate allele ratio between different genetic identities. Allele ratio for each targeted locus is calculated as $R_{allele}=N_1/N_2$, where $N_1$ is unique UMI number for the first genetic identity, and $N_2$ is unique UMI number for the second genetic identity. (FIG. 12B) Genetic identity calling for each UMI family based on majority vote.

Figure 13:
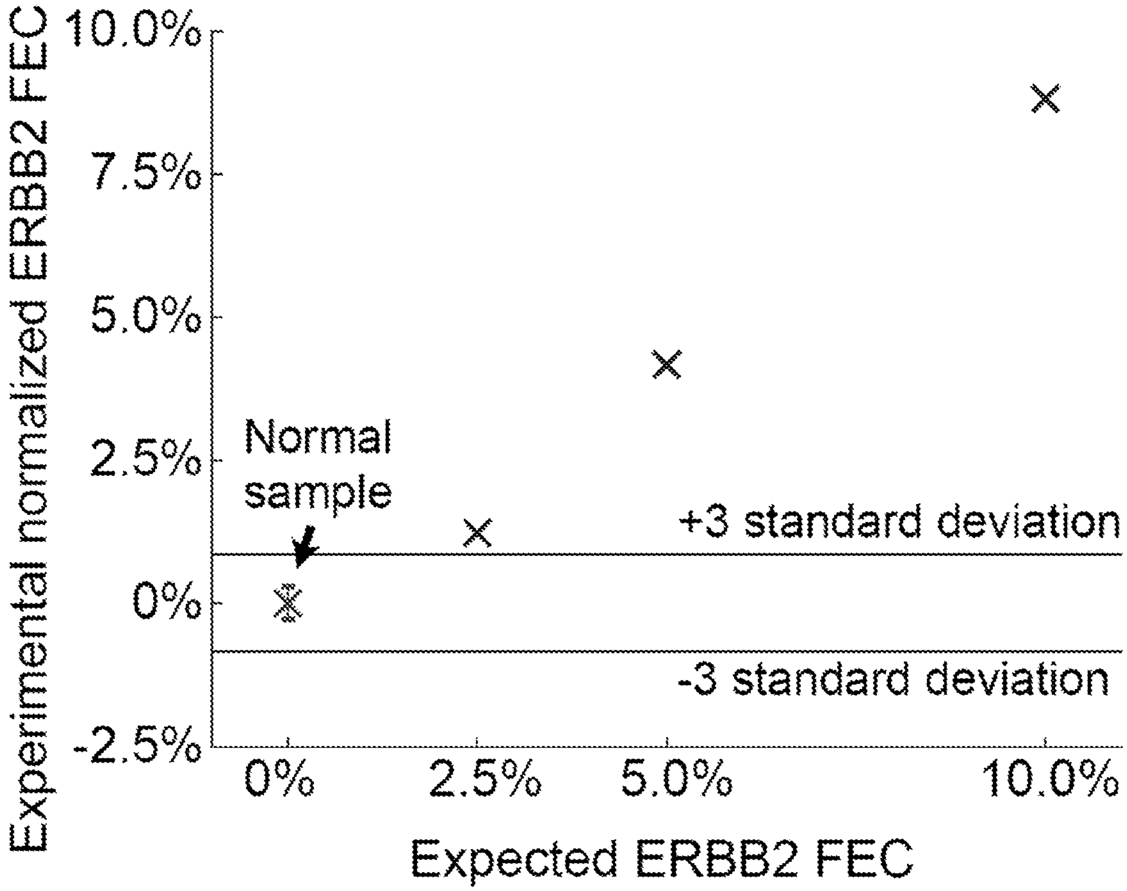

FIG. 13. Example of experimental results of CNV detection on spike-in clinical FFPE samples. Two previously characterized FFPE DNA samples (1 "normal" sample and 1 "ERBB2 amplified abnormal" sample) were mixed to generate 2.5%, 5%, and 10% ERBB2 FEC samples. The "normal" sample has an ERBB2 FEC of 0%, and the "ERBB2 amplified abnormal" sample has an ERBB2 FEC of 78%. The experimental normalized FEC values were plotted against expected ERBB2 FEC. The "normal" sample was tested in 5 replicates, and the LoD of the 100-plex CNV panel was estimated as 3 standard deviation of the "normal" sample. CNV in 2.5%, 5%, and 10% ERBB2 FEC samples were successfully detected, because their calculated FEC were outside the 3 standard deviation range.

Figure 14:
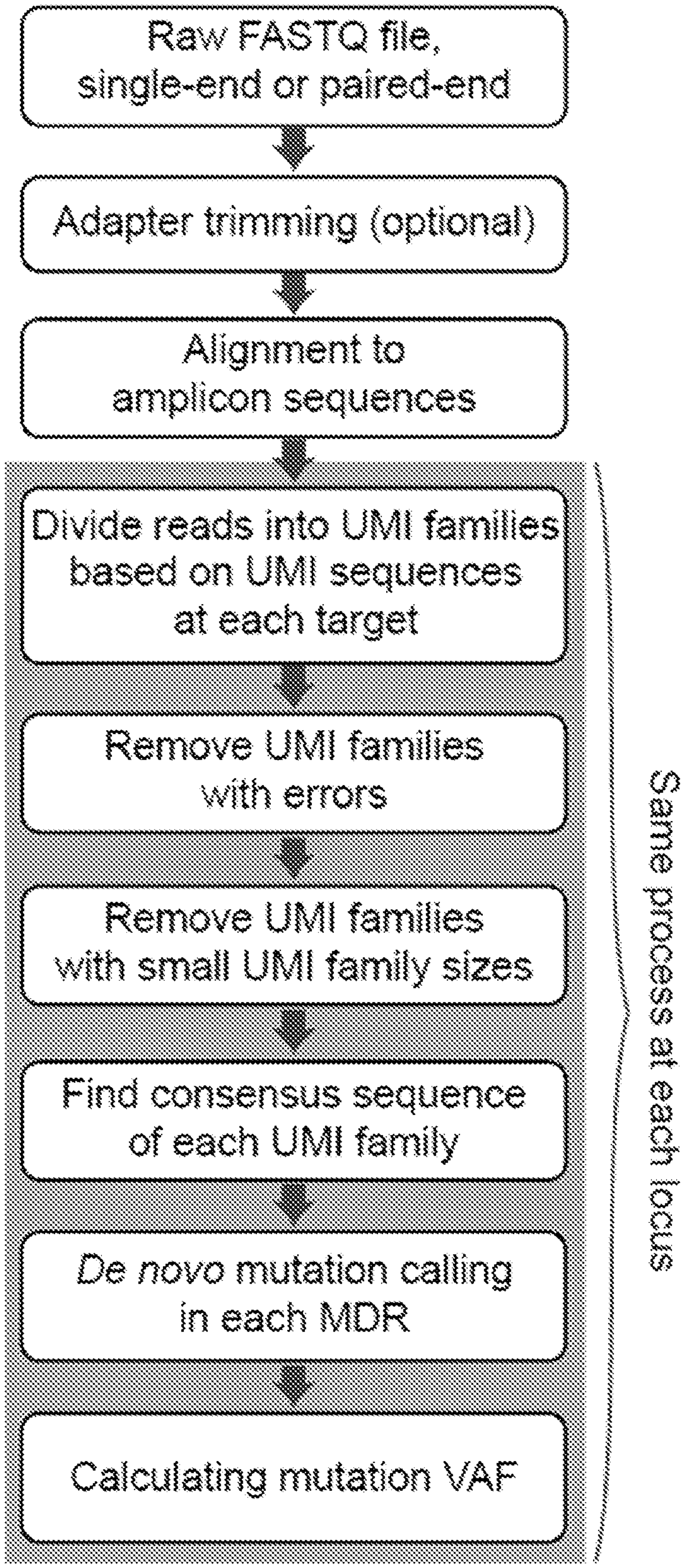

FIG. 14. Bioinformatics workflow for mutation quantitation using QASeq. Shown is a summary of the data processing workflow for mutation quantitation.

Figure 15:
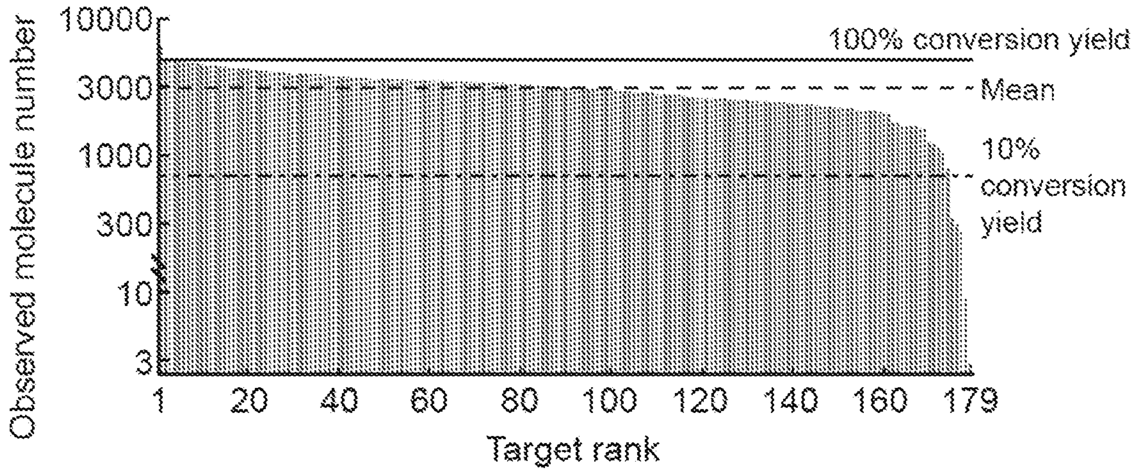

FIG. 15. Observed molecule number for the 179-plex comprehensive panel. The input was 8.3 ng (5000 expected molecule number) of 100% Multiplex I Wild Type cfDNA Reference Standard (Horizon Discovery). The conversion rate has an average of 62%; 97% of the plexes have >10% conversion rate.

Figure 16:
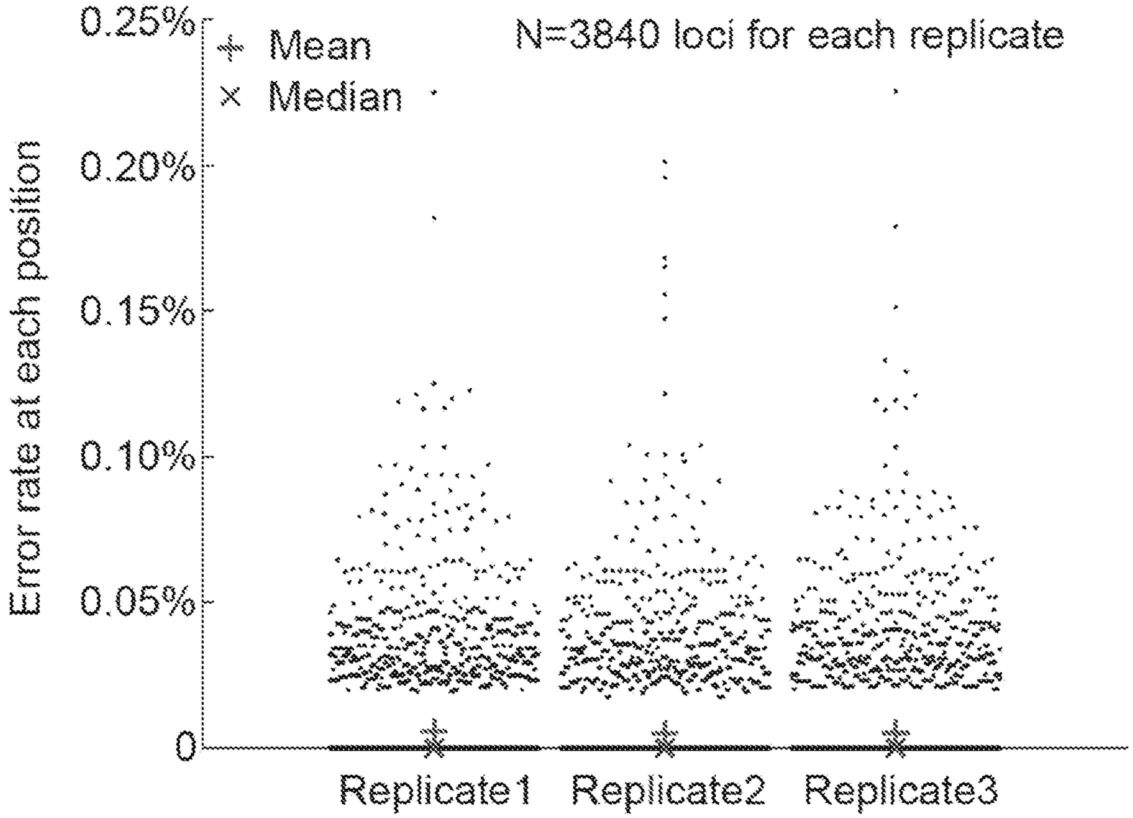

FIG. 16. Error rates for the 179-plex comprehensive panel. The input was 8.3 ng of 100% Multiplex I Wild Type cfDNA Reference Standard (Horizon Discovery); the same sample was tested in triplicate. Error rates in 3840 different loci (after error correction using UMI) were plotted. Highest error rates were 0.23%, 0.20%, and 0.23%, and average error rates were 0.006%, 0.005%, and 0.005% for the 3 replicates.

Figure 17:
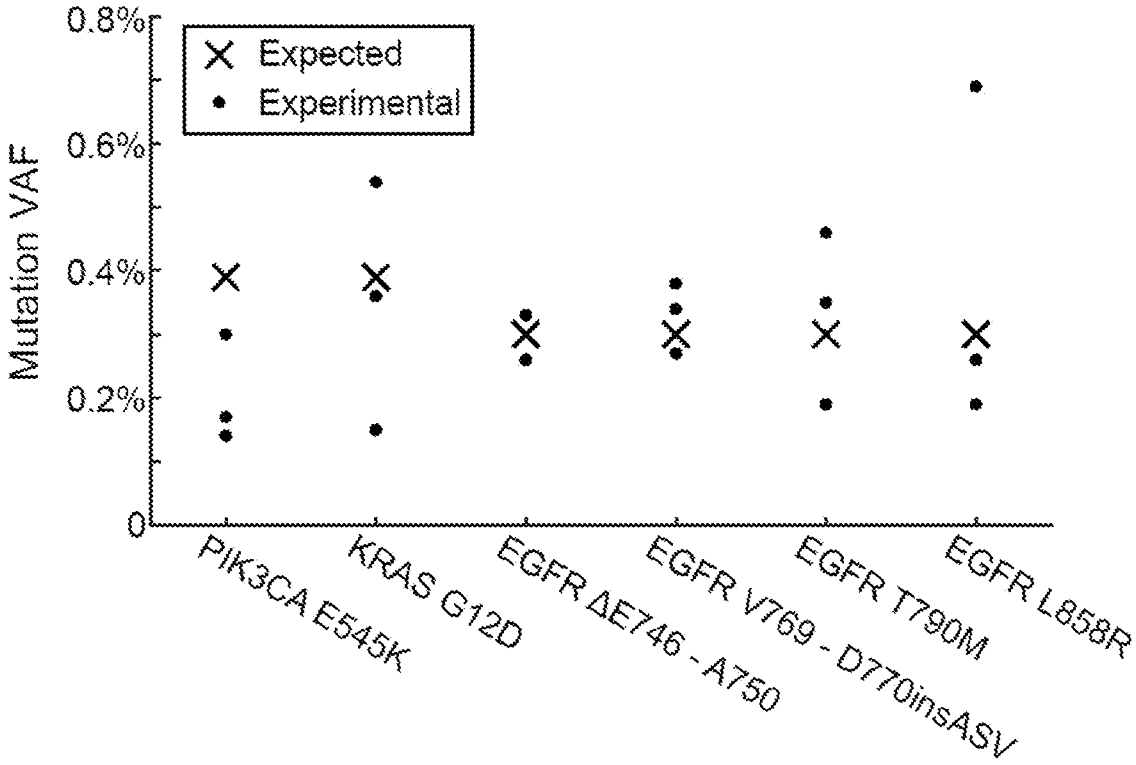

FIG. 17. Mutation quantitation results for the 179-plex comprehensive panel. Sample used was 0.3% cfDNA Reference Standard (created by mixing 0.1% Multiplex I cfDNA Reference Standard and 1% Multiplex I cfDNA Reference Standard from Horizon Discovery) tested in triplicates. The experimental VAF of 6 mutations were generally consistent with the expected VAF; the difference was mostly due to stochasticity in sampling a small number (≤9) of mutation molecules.

DETAILED DESCRIPTION

Provided herein are methods of quantitative amplicon sequencing, for labeling each strand of targeted genomic loci in the original DNA sample with an oligonucleotide barcode sequence by polymerase chain reaction, and amplifying the genomic region(s) for high-throughput sequencing. Also provided herein are methods to allow the simultaneous detection of copy number variation (CNV) in a set of genes of interest, by quantitating the frequency of extra copies of each gene. Quantitation of the allele ratio of different genetic identities for targeted genomic loci using multiplexed PCR is also provided by the disclosed methods. These methods can be applied to the detection of CNV for gene(s) of interest in tumor samples, guiding the choice of targeted therapy, and helping the understanding of cancer formation and progression.

Current standard method for prenatal diagnosis of monogenic diseases is to sequence the fetal genetic material obtained from invasive and risky chorionic villus sampling or amniocentesis. Genetic noninvasive prenatal testing (NIPT) of monogenic disease is based on the circulation of fetal-derived cell-free DNA (cfDNA) in maternal plasma. Due to the presence of background maternal DNA, it becomes challenging to confidently detect the allele ratio change arising from fetal cfDNA, especially when the maternal DNA is heterozygous at the locus of interest. Droplet digital PCR (ddPCR) has been used to quantify the allele ratio between mutant alleles carrying disease-causing mutations and wild type alleles for NIPT (Lun et al., 2008), but the practical feasibility is limited by precision and reliability of the technology. QASeq enables absolute quantitation of DNA molecule by adding unique molecular identifier to each strand of original input molecules, and can be applied to allele ratio quantitation for NIPT. As such, QASeq can also be used for allele ratio quantitation. Allele ratio quantitation aims to quantify the ratio of DNA molecules with different genetic identities. Accurate allele ratio quantitation is key to NIPT of monogenic diseases, such as β-thalassemia and cystic fibrosis.

I. Frequency of Extra Copies of CNVS

The frequency of extra copies (FEC) of a CNV in a genomic DNA sample is defined herein as:

$$FEC = \frac{\text{Copies of the target genomic region} - \text{Haploid genomic copies}}{\text{Haploid genomic copies}}$$

A positive value of FEC indicates amplification of the target genomic region in the sample, and a negative value of FEC indicates deletion of the target genomic region in the sample.

While QASeq can be used to quantitate FEC, it does not provide information on the percentage of cells containing CNV in the tumor tissue sample. For example, if 1% of cells in a tumor sample contain 4 copies of ERBB2, and the rest 99% of cells contain 2 copies, the FEC is 1%; if 0.5% of cells in the sample contain 6 copies of ERBB2, and the rest 99.5% of cells contain 2 copies, the FEC is still 1%. Additionally, QASeq does not provide information on the genomic locations of the extra copies.

II. Multiplexed PCR Panel Design

In a QASeq multiplexed PCR panel, one target gene needs M (M=1~1000) sets of primers, each amplifying a non-overlapping small region (40 nt to 500 nt, usually ≤200 nt) in the target gene region. If the panel has multiple target genes, the number of primer sets used for each gene is similar (≈M). The panel also contains a similar number (≈M) of primer sets amplifying reference genomic regions. The reference loci serve as internal standards for the amount of genomic DNA (gDNA) loaded, so that accurate quantitation of DNA concentration in the sample is not needed. At least one reference primer set may be used for each panel. Because increasing the number of input molecules or loci in the target gene can both decrease variations in random sampling, a greater number of primer sets per gene can be used to improve the LoD for sample types containing smaller amounts of DNA; the number of reference primer sets needs to be increased proportionally in this case.

Figure 1:
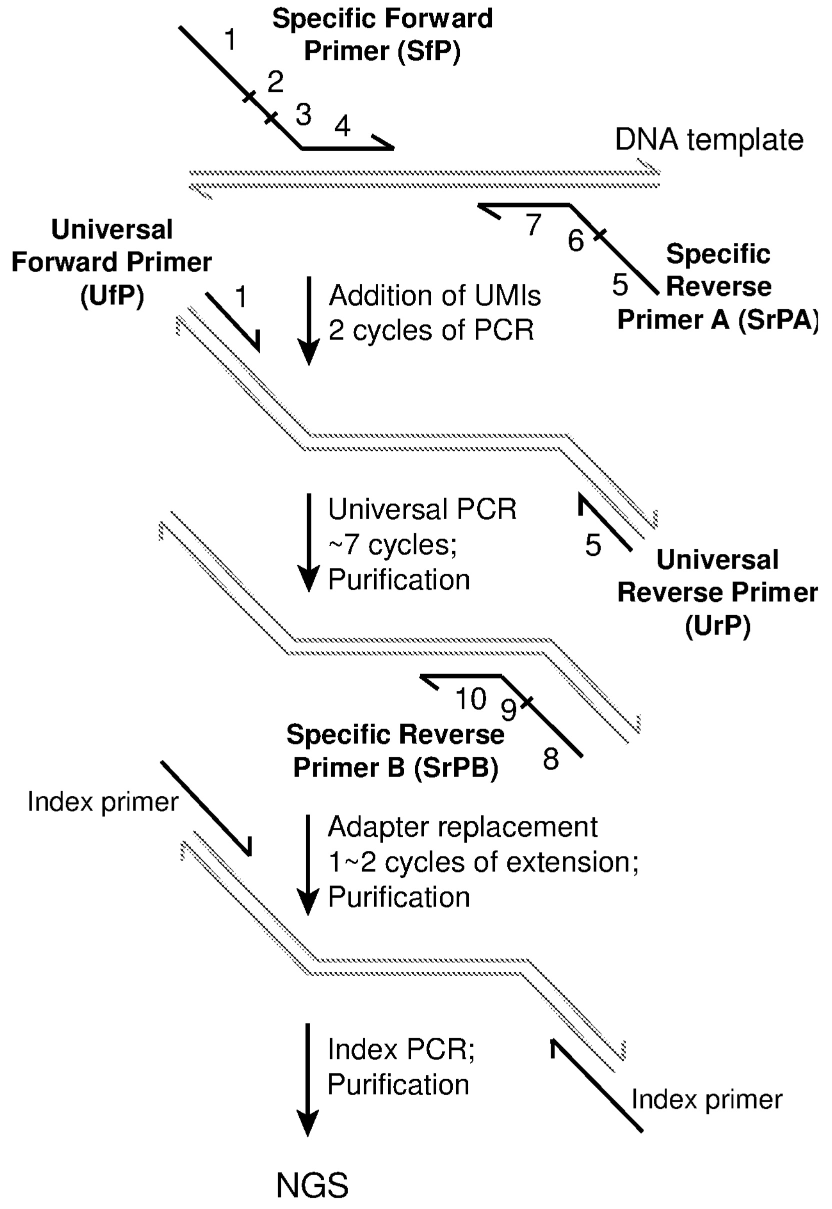
FIG. 1. Schematic of QASeq primers design and experimental workflow. Each primer set contains 3 different oligos: a Specific Forward Primer (SfP), a Specific Reverse Primer A (SrPA), and a Specific Reverse Primer B (SrPB). Each QASeq panel only needs one Universal Forward Primer (UfP) and one Universal Reverse Primer (UrP). There can be additional bases at 5'-end of region 1 or region 5 in UfP or UrP. For one recommended workflow, the DNA sample is firstly mixed with all the SfP, SrPA, DNA polymerase, dNTPs, and PCR buffer. 2 cycles of long-extension PCR are performed for addition of UMI on all target loci. Next, in order to amplify the molecules while preventing addition of multiple UMIs onto the same original molecule, the annealing temperature is raised by about 8° C. in PCR amplification for about 7 cycles using UfP and UrP (short-extension, about 30 s); note that addition of UfP and UrP into the reaction is an open-tube step on the thermocycler. After purification using SPRI magnetic beads or columns, SrPB primers, DNA polymerase, dNTPs, and PCR buffer are mixed with the PCR product for adapter replacement; after 2 cycles of long extension (about 30 min), the NGS adapters are only added onto the correct PCR products, not the primer dimers or non-specific products. After another purification using SPRI magnetic beads or columns, standard NGS index PCR is performed; libraries are normalized and loaded onto an Illumina sequencer.

Each primer set contains three different oligos: a Specific Forward Primer (SfP), a Specific Reverse Primer A (SrPA), and a Specific Reverse Primer B (SrPB) (see FIG. 1). SfP comprises, from 5' to 3', regions 1, 2, 3, and 4. Region 4 is the template-binding region; region 3 is the UMI; region 1 is a full or partial NGS adapter; region 2 is an optional spacer region (typically 0~15 nt) added for uniform amplification of UMIs. SrPA comprises, from 5' to 3', regions 5, 6, and 7. Region 7 is the template-binding region; region 5 is the custom adapter (i.e., a sequence that is different from the NGS adapters and cannot be found in the human genome) for universal amplification; region 6 is an optional spacer region (typically 0~15 nt) added for uniform amplification of different loci. SrPB comprises, from 5' to 3', regions 8, 9, and 10. Region 10 is the template-binding region, the 3'-end of which is closer to region 4 than region 7 by at least 1 base; region 8 is a full or partial NGS adapter; region 9 is an optional spacer region (typically 0~15 nt) added for uniform amplification of different loci. Each QASeq panel only needs one Universal Forward Primer (UfP) and one Universal Reverse Primer (UrP). UfP comprises region 1, and UrP comprises region 5; there can be additional bases at the 5'-end of region 1 or region 5 in UfP or UrP. The melting temperature (Tm) of template-binding regions 4, 7, and 10 are about the same as the PCR annealing temperature, and the Tm of UfP and UrP are not lower than regions 4, 7, and 10 in the experimental PCR conditions.

When designing primers, single nucleotide polymorphisms (SNPs) with significant minor allele frequency (MAF) should be avoided in the primer-binding regions, so that the primers' binding affinities will not likely be affected by nucleotide sequence variations in different patient samples. In addition, whole human genome nucleotide sequences should be searched to ensure that the primers are not prone to nonspecific amplification of non-target regions.

In an example panel targeting CNVs of ERBB2 in Formalin-Fixed Paraffin-Embedded (FFPE) specimen of tumor samples, 10 sets of primers, each amplifying a 60 to 70 nt amplicon, were designed in the ERBB2 gene region. In addition, 10 sets of reference primers were designed, each amplifying a region in a different housekeeping gene from different chromosomes (Table 1). Primers were designed automatically using a Matlab code to satisfy the above-mentioned design principles while minimize primer interactions. In addition, non-pathogenic SNPs with >0.2% MAF in the population were avoided. Online tool Primer-BLAST was used to ensure that each primer set only has one amplicon in the human genome. Primer sequences are shown in Table 2.

TABLE 1

Locations of amplicons

| Amplicon name | Chromosome | Gene |
|---|---|---|
| ERBB2 1~10 | Chr. 17 | ERBB2 |
| Reference 1 | Chr. 1 | PSMB2 |
| Reference 2 | Chr. 3 | RPL32 |
| Reference 3 | Chr. 5 | RACK1 |
| Reference 4 | Chr. 6 | TBP |
| Reference 5 | Chr. 9 | VCP |
| Reference 6 | Chr. 11 | HMBS |
| Reference 7 | Chr. 12 | NACA |
| Reference 8 | Chr. 15 | B2M |
| Reference 9 | Chr. 19 | GPI |
| Reference 10 | Chr. 20 | TOP1 |

TABLE 2

Primer sequences in an exemplary QASeq panel

| Name | Sequence | SEQ ID NO: |
|---|---|---|
| SfP-ERBB2-1 | ACACGACGCTCTTCCGATCTATCAHHHHHHHHHHHHHHHHAATCATAAAAGCTAACATATAGCCTGGG | 1 |
| SfP-ERBB2-2 | ACACGACGCTCTTCCGATCTATCAHHHHHHHHHHHHHHHHGCTGACTTGGGGACACAGG | 2 |
| SfP-ERBB2-3 | ACACGACGCTCTTCCGATCTATCAHHHHHHHHHHHHHHHHCTTTGCAAGATGGAGGTTGCA | 3 |
| SfP-ERBB2-4 | ACACGACGCTCTTCCGATCTATCAHHHHHHHHHHHHHHHHCTTGCCCTACCAGCCTCTC | 4 |
| SfP-ERBB2-5 | ACACGACGCTCTTCCGATCTATCAHHHHHHHHHHHHHHHHCCACAACTGGAATCTGACGC | 5 |
| SfP-ERBB2-6 | ACACGACGCTCTTCCGATCTATCAHHHHHHHHHHHHHHHHGGCTGCGGATTGTGCG | 6 |
| SfP-ERBB2-7 | ACACGACGCTCTTCCGATCTATCAHHHHHHHHHHHHHHHHCAGATATAAGGGCCAAAAGTTACACA | 7 |
| SfP-ERBB2-8 | ACACGACGCTCTTCCGATCTATCAHHHHHHHHHHHHHHHHTGCTTTGGTCTCCCTTTTTGC | 8 |
| SfP-ERBB2-9 | ACACGACGCTCTTCCGATCTATCAHHHHHHHHHHHHHHHHGAATGAAATTAAACAGGGCTTGGC | 9 |
| SfP-ERBB2-10 | ACACGACGCTCTTCCGATCTATCAHHHHHHHHHHHHHHHHAAAGAAAAAAAAAAGAATATGGGTCCAGA | 10 |
| SfP-Ref-1 | ACACGACGCTCTTCCGATCTATCAHHHHHHHHHHHHHHHHGCACAACATTTTGTCTCCGGAAAATA | 11 |
| SfP-Ref-2 | ACACGACGCTCTTCCGATCTATCAHHHHHHHHHHHHHHHHGACAAATGCCCAGAAATGGAACTTA | 12 |
| SfP-Ref-3 | ACACGACGCTCTTCCGATCTATCAHHHHHHHHHHHHHHHHATGCGGTTTCACCATTGGC | 13 |
| SfP-Ref-4 | ACACGACGCTCTTCCGATCTATCAHHHHHHHHHHHHHHHHCCCAAGGAATTGAGGAAGTTGCT | 14 |
| SfP-Ref-5 | ACACGACGCTCTTCCGATCTATCAHHHHHHHHHHHHHHHHACTGGAATGCTGTTCCTTACAATCA | 15 |
| SfP-Ref-6 | ACACGACGCTCTTCCGATCTATCAHHHHHHHHHHHHHHHHGGCCTGGATAGGCAGCTTG | 16 |
| SfP-Ref-7 | ACACGACGCTCTTCCGATCTATCAHHHHHHHHHHHHHHHHCAACTCAGACTATTCAGGAATACGTTT | 17 |

TABLE 2-continued

Primer sequences in an exemplary QASeq panel

| Name | Sequence | SEQ ID NO: |
|---|---|---|
| SfP-Ref-8 | ACACGACGCTCTTCCGATCTATCAHHHHHHHHHHHHHHHTCCAT CCGACATTGAAGTTGACTTA | 18 |
| SfP-Ref-9 | ACACGACGCTCTTCCGATCTATCAHHHHHHHHHHHHHHHGAATG AAGCCCTAATCCCTTAAGC | 19 |
| SfP-Ref-10 | ACACGACGCTCTTCCGATCTATCAHHHHHHHHHHHHHHHCAGGC AGAGGAAATATCGTTGAC | 20 |
| SrPA-ERBB2-1 | GGATATTCCTTTCTACTCTTTGACATCATCTATGCATGCAAAAC ACCACAAAC | 21 |
| SrPA-ERBB2-2 | GGATATTCCTTTCTACTCTTTGACATCATCTCAGATCTGGCCCA GCACC | 22 |
| SrPA-ERBB2-3 | GGATATTCCTTTCTACTCTTTGACATCATCTCCTGGCAGGCACT CTCG | 23 |
| SrPA-ERBB2-4 | GGATATTCCTTTCTACTCTTTGACATCATCTCCTAAGGTCAAAT CCTAGGGGG | 24 |
| SrPA-ERBB2-5 | GGATATTCCTTTCTACTCTTTGACATCATCTCGGGGCTCTGGTC ATTGC | 25 |
| SrPA-ERBB2-6 | GGATATTCCTTTCTACTCTTTGACATCATCTTCAGCGGGTCTCC ATTGTCTA | 26 |
| SrPA-ERBB2-7 | GGATATTCCTTTCTACTCTTTGACATCATCTGCTTGGTGGTTAA GAGACTGTGG | 27 |
| SrPA-ERBB2-8 | GGATATTCCTTTCTACTCTTTGACATCATCTCCATTTACCCCTC ACAACAACCA | 28 |
| SrPA-ERBB2-9 | GGATATTCCTTTCTACTCTTTGACATCATCTCGAGTAACAACAG TCACTGCTC | 29 |
| SrPA-ERBB2-10 | GGATATTCCTTTCTACTCTTTGACATCATCTATGTTTTTCCATG TTCTAACACCGT | 30 |
| SrPA-Ref-1 | GGATATTCCTTTCTACTCTTTGACATCATCTGCTCCAGATGGGC AGCAC | 31 |
| SrPA-Ref-2 | GGATATTCCTTTCTACTCTTTGACATCATCTTTGGCAGTCTTTA AGATCCATAGAAATAC | 32 |
| SrPA-Ref-3 | GGATATTCCTTTCTACTCTTTGACATCATCTACTTTGGAAGGCA GAGGCG | 33 |
| SrPA-Ref-4 | GGATATTCCTTTCTACTCTTTGACATCATCTTGGAACTCGTCTC ACTATTCAATTTTT | 34 |
| SrPA-Ref-5 | GGATATTCCTTTCTACTCTTTGACATCATCTCTGCTTGTGGATG AGGCCATA | 35 |
| SrPA-Ref-6 | GGATATTCCTTTCTACTCTTTGACATCATCTAGGCAGTCACTGT TCCTTTCC | 36 |
| SrPA-Ref-7 | GGATATTCCTTTCTACTCTTTGACATCATCTATGCATTTACTTC TGAAACAGTCCTT | 37 |
| SrPA-Ref-8 | GGATATTCCTTTCTACTCTTTGACATCATCTCAAGTCTGAATGC TCCACTTTTTCA | 38 |
| SrPA-Ref-9 | GGATATTCCTTTCTACTCTTTGACATCATCTGTCTCATTCTAGA AAGAAGTTAACTCATTATACA | 39 |
| SrPA-Ref-10 | GGATATTCCTTTCTACTCTTTGACATCATCTAGGAATCAACAAA TGACAAGGCAAAT | 40 |
| SrPB-ERBB2-1 | AGACGTGTGCTCTTCCGATCTCATGCAAAACACCACAAACAGTT C | 41 |
| SrPB-ERBB2-2 | AGACGTGTGCTCTTCCGATCTGATCTGGCCCAGCACCTTAA | 42 |

TABLE 2-continued

| Primer sequences in an exemplary QASeq panel | | |
|---|---|---|
| Name | Sequence | SEQ ID NO: |
| SrPB-ERBB2-3 | AGACGTGTGCTCTTCCGATCTCTCTCGGTGGATCTGCATAACAT | 43 |
| SrPB-ERBB2-4 | AGACGTGTGCTCTTCCGATCTGTCAAATCCTAGGGGGTAATACGA | 44 |
| SrPB-ERBB2-5 | AGACGTGTGCTCTTCCGATCTCTGGTCATTGCAGAGACCTCT | 45 |
| SrPB-ERBB2-6 | AGACGTGTGCTCTTCCGATCTTCTCCATTGTCTAGCACGGC | 46 |
| SrPB-ERBB2-7 | AGACGTGTGCTCTTCCGATCTAGACTGTGGAGTCTGAAACTCAG | 47 |
| SrPB-ERBB2-8 | AGACGTGTGCTCTTCCGATCTCCCCTCACAACAACCAGACG | 48 |
| SrPB-ERBB2-9 | AGACGTGTGCTCTTCCGATCTGTCACTGCTCTGTAGAAAGCCT | 49 |
| SrPB-ERBB2-10 | AGACGTGTGCTCTTCCGATCTATGTTCTAACACCGTGATCTGGAT | 50 |
| SrPB-Ref-1 | AGACGTGTGCTCTTCCGATCTATGGGCAGCACAGTGGG | 51 |
| SrPB-Ref-2 | AGACGTGTGCTCTTCCGATCTGCAGTCTTTAAGATCCATAGAAATACTCTT | 52 |
| SrPB-Ref-3 | AGACGTGTGCTCTTCCGATCTCAGAGGCGAGTGGATCACTT | 53 |
| SrPB-Ref-4 | AGACGTGTGCTCTTCCGATCTACTATTCAATTTTTTCCTAGAGCATCTCC | 54 |
| SrPB-Ref-5 | AGACGTGTGCTCTTCCGATCTGGCCATAGAAAGGGTAGTGTTGAA | 55 |
| SrPB-Ref-6 | AGACGTGTGCTCTTCCGATCTTTCCTTTCCTCCTCCTCCCAT | 56 |
| SrPB-Ref-7 | AGACGTGTGCTCTTCCGATCTGCATTTACTTCTGAAACAGTCCTTAATG | 57 |
| SrPB-Ref-8 | AGACGTGTGCTCTTCCGATCTAATGCTCCACTTTTTCAATTCTCTCT | 58 |
| SrPB-Ref-9 | AGACGTGTGCTCTTCCGATCTATTCTAGAAAGAAGTTAACTCATTATACACAGT | 59 |
| SrPB-Ref-10 | AGACGTGTGCTCTTCCGATCTACAAATGACAAGGCAAATGAGACAT | 60 |
| UfP | ACACTCTTTCCCTACACGACGCTCTTCCGATCT | 61 |
| UrP | CCTATGGTAGTTAAATGTACATTGGATATTCCTTTCTACTCTTTGACATCATCT | 62 |

TABLE 3

| Primer sequences in the 179-plex comprehensive panel | | |
|---|---|---|
| Name | Primer sequence | SEQ ID NO: |
| UfP | ACACTCTTTCCCTACACGACGCTCTTCCGATCT | 61 |
| UrP | CCTATGGTAGTTAAATGTACATTGGATATTCCTTTCTACTCTTTGACATCATCT | 62 |

TABLE 3-continued

Primer sequences in the 179-plex comprehensive panel

| Name | Primer sequence | SEQ ID NO: |
| --- | --- | --- |
| fP-ERBB2-1 | ACACGACGCTCTTCCGATCTATCAHHHHHHHHHHHHHHH CCTTAGACAACTACCTTTCTACGGAC | 63 |
| fP-ERBB2-10 | ACACGACGCTCTTCCGATCTATCAHHHHHHHHHHHHHHH TGCTTTGGTCTCCCTTTTTGC | 64 |
| fP-ERBB2-11 | ACACGACGCTCTTCCGATCTATCAHHHHHHHHHHHHHHH AAAGAAAAAAAAAAAGAATATGGGTCCAGA | 65 |
| fP-ERBB2-12 | ACACGACGCTCTTCCGATCTATCAHHHHHHHHHHHHHHH CGAGGCGATAGGGTTAAGGG | 66 |
| fP-ERBB2-13 | ACACGACGCTCTTCCGATCTATCAHHHHHHHHHHHHHHH CTTCTAGTCGCAATTGAAGTACCAC | 67 |
| fP-ERBB2-14 | ACACGACGCTCTTCCGATCTATCAHHHHHHHHHHHHHHH CCTCACCCCTTGTCAACTTTTC | 68 |
| fP-ERBB2-15 | ACACGACGCTCTTCCGATCTATCAHHHHHHHHHHHHHHH GTCTGGTGCTTTAGCCCAAAG | 69 |
| fP-ERBB2-16 | ACACGACGCTCTTCCGATCTATCAHHHHHHHHHHHHHHH AAAGCAAAGCTATATTCAAGACCACAT | 70 |
| fP-ERBB2-17 | ACACGACGCTCTTCCGATCTATCAHHHHHHHHHHHHHHH GGCATTGTCTGCCAGTCCG | 71 |
| fP-ERBB2-18 | ACACGACGCTCTTCCGATCTATCAHHHHHHHHHHHHHHH TCCTTTAGCTCGTGGAATCTCAAG | 72 |
| fP-ERBB2-19 | ACACGACGCTCTTCCGATCTATCAHHHHHHHHHHHHHHH CTGGGGCATTCCAACTAGAACT | 73 |
| fP-ERBB2-2 | ACACGACGCTCTTCCGATCTATCAHHHHHHHHHHHHHHH ATTCCAGTGGCCATCAAAGTGT | 74 |
| fP-ERBB2-20 | ACACGACGCTCTTCCGATCTATCAHHHHHHHHHHHHHHH GGGAAAACCATTATTTGATATTAAAACAAATAGG | 75 |
| fP-ERBB2-21 | ACACGACGCTCTTCCGATCTATCAHHHHHHHHHHHHHHH AGGAAGTATAAGAATGAAGTTGTGAAGC | 76 |
| fP-ERBB2-22 | ACACGACGCTCTTCCGATCTATCAHHHHHHHHHHHHHHH CTCCCCGCTCCCCTTCA | 77 |
| fP-ERBB2-23 | ACACGACGCTCTTCCGATCTATCAHHHHHHHHHHHHHHH AGCCTGGGCCAGGTATACT | 78 |
| fP-ERBB2-24 | ACACGACGCTCTTCCGATCTATCAHHHHHHHHHHHHHHH ACTCTGTCCTCTGCAGGAACT | 79 |
| fP-ERBB2-25 | ACACGACGCTCTTCCGATCTATCAHHHHHHHHHHHHHHH GTATGGGTTTTACAAATTGCAGCAAATA | 80 |
| fP-ERBB2-26 | ACACGACGCTCTTCCGATCTATCAHHHHHHHHHHHHHHH CAAAGCATGTTTAATTTTCTCGTGGTT | 81 |
| fP-ERBB2-27 | ACACGACGCTCTTCCGATCTATCAHHHHHHHHHHHHHHH GCGTGAGGGGCCAGTGT | 82 |
| fP-ERBB2-28 | ACACGACGCTCTTCCGATCTATCAHHHHHHHHHHHHHHH GGACACAGGTCATTTTACTGTAGTATTC | 83 |
| fP-ERBB2-29 | ACACGACGCTCTTCCGATCTATCAHHHHHHHHHHHHHHH CCACCCGTTCTGACCCTC | 84 |
| fP-ERBB2-3 | ACACGACGCTCTTCCGATCTATCAHHHHHHHHHHHHHHH CAGGAAGCATACGTGATGGCT | 85 |
| fP-ERBB2-30 | ACACGACGCTCTTCCGATCTATCAHHHHHHHHHHHHHHH ACCTGCAGTGTGCAAGGG | 86 |
| fP-ERBB2-31 | ACACGACGCTCTTCCGATCTATCAHHHHHHHHHHHHHHH GCGTCTGTGTTTCCGCTAAATC | 87 |

TABLE 3-continued

Primer sequences in the 179-plex comprehensive panel

| Name | Primer sequence | SEQ ID NO: |
|---|---|---|
| fP-ERBB2-32 | ACACGACGCTCTTCCGATCTATCAHHHHHHHHHHHHHHH AAGATCTCCAAGTACTGGGGAAC | 88 |
| fP-ERBB2-33 | ACACGACGCTCTTCCGATCTATCAHHHHHHHHHHHHHHH TGGCCTTCACCGTCATTGAAA | 89 |
| fP-ERBB2-34 | ACACGACGCTCTTCCGATCTATCAHHHHHHHHHHHHHHH GCAGATATAAGGGCCAAAAGTTACAC | 90 |
| fP-ERBB2-35 | ACACGACGCTCTTCCGATCTATCAHHHHHHHHHHHHHHH CAGCTGGCTCTCACACTGAT | 91 |
| fP-ERBB2-36 | ACACGACGCTCTTCCGATCTATCAHHHHHHHHHHHHHHH CCACCCCTGTTCTCCGATG | 92 |
| fP-ERBB2-37 | ACACGACGCTCTTCCGATCTATCAHHHHHHHHHHHHHHH CTCCTAAATGTTAGCTTTTATTCTATAGCCT | 93 |
| fP-ERBB2-38 | ACACGACGCTCTTCCGATCTATCAHHHHHHHHHHHHHHH AGTCTCTGCCTTCTACTCTCTACC | 94 |
| fP-ERBB2-39 | ACACGACGCTCTTCCGATCTATCAHHHHHHHHHHHHHHH GCCTTTGGTGGGTGGGG | 95 |
| fP-ERBB2-4 | ACACGACGCTCTTCCGATCTATCAHHHHHHHHHHHHHHH GATGAGCTACCTGGAGGATGTG | 96 |
| fP-ERBB2-40 | ACACGACGCTCTTCCGATCTATCAHHHHHHHHHHHHHHH CAGCCAGTTCCCTGGTTCA | 97 |
| fP-ERBB2-41 | ACACGACGCTCTTCCGATCTATCAHHHHHHHHHHHHHHH CCCTTCAGACTATGAAAAGGTTCTAAG | 98 |
| fP-ERBB2-42 | ACACGACGCTCTTCCGATCTATCAHHHHHHHHHHHHHHH ACAGTGCTGGCAATGTTTATCAC | 99 |
| fP-ERBB2-43 | ACACGACGCTCTTCCGATCTATCAHHHHHHHHHHHHHHH GGGTGGTTCCCAGAATTGTTG | 100 |
| fP-ERBB2-44 | ACACGACGCTCTTCCGATCTATCAHHHHHHHHHHHHHHH CTTCAAAGTTCTGGTGTCGGG | 101 |
| fP-ERBB2-45 | ACACGACGCTCTTCCGATCTATCAHHHHHHHHHHHHHHH TGACCTGTGGGTGGAAATTTTG | 102 |
| fP-ERBB2-46 | ACACGACGCTCTTCCGATCTATCAHHHHHHHHHHHHHHH AGAGGGTTCTGATTGCCTACAAG | 103 |
| fP-ERBB2-47 | ACACGACGCTCTTCCGATCTATCAHHHHHHHHHHHHHHH GGGATCCTCATCAAGCGACG | 104 |
| fP-ERBB2-48 | ACACGACGCTCTTCCGATCTATCAHHHHHHHHHHHHHHH CCCTTTTACAGTCAAAGTCCAAAGC | 105 |
| fP-ERBB2-49 | ACACGACGCTCTTCCGATCTATCAHHHHHHHHHHHHHHH GGGTCGTCAAAGACGTTTTTGC | 106 |
| fP-ERBB2-5 | ACACGACGCTCTTCCGATCTATCAHHHHHHHHHHHHHHH GATGGCGCTGGAGTCCATT | 107 |
| fP-ERBB2-50 | ACACGACGCTCTTCCGATCTATCAHHHHHHHHHHHHHHH ACCTGTCCTAAGGAACCTTCCT | 108 |
| fP-ERBB2-6 | ACACGACGCTCTTCCGATCTATCAHHHHHHHHHHHHHHH CTTTGCAAGATGGAGGTTGCA | 109 |
| fP-ERBB2-7 | ACACGACGCTCTTCCGATCTATCAHHHHHHHHHHHHHHH CTTGCCCTACCAGCCTCTC | 110 |
| fP-ERBB2-8 | ACACGACGCTCTTCCGATCTATCAHHHHHHHHHHHHHHH CCACAACTGGAATCTGACGC | 111 |
| fP-ERBB2-9 | ACACGACGCTCTTCCGATCTATCAHHHHHHHHHHHHHHH GGCTGCGGATTGTGCG | 112 |

TABLE 3-continued

Primer sequences in the 179-plex comprehensive panel

| Name | Primer sequence | SEQ ID NO: |
|---|---|---|
| fP-Mut1 | ACACGACGCTCTTCCGATCTATCAHHHHHHHHHHHHHHH GGGACCCACTCCATCGAGA | 113 |
| fP-Mut2 | ACACGACGCTCTTCCGATCTATCAHHHHHHHHHHHHHHH GGAGTATTTCATGAAACAAATGAATGATGC | 114 |
| fP-Mut4 | ACACGACGCTCTTCCGATCTATCAHHHHHHHHHHHHHHH GCCGCCAGGTCTTGATGTACT | 115 |
| fP-Mut5 | ACACGACGCTCTTCCGATCTATCAHHHHHHHHHHHHHHH CTCACCATCGCTATCTGAGCAG | 116 |
| fP-Mut6 | ACACGACGCTCTTCCGATCTATCAHHHHHHHHHHHHHHH TCGTCAAGGCACTCTTGCCTA | 117 |
| fP-mut10 | ACACGACGCTCTTCCGATCTTCTTHHHHHHHHHHHHHHH GAGTATTTGGATGACAGAAACACTTT | 118 |
| fP-mut11 | ACACGACGCTCTTCCGATCTTCTTHHHHHHHHHHHHHHH CACACGCAAATTTCCTTCCAC | 119 |
| fP-mut12 | ACACGACGCTCTTCCGATCTTCTTHHHHHHHHHHHHHHH CCGCTCATGATCAAACGCTCTAA | 120 |
| fP-mut13 | ACACGACGCTCTTCCGATCTTCTTHHHHHHHHHHHHHHH TCCATGATCAGGTCCACCTTCT | 121 |
| fP-mut14 | ACACGACGCTCTTCCGATCTTCTTHHHHHHHHHHHHHHH TCACTCTCTCTCTGCGCATTC | 122 |
| fP-mut15 | ACACGACGCTCTTCCGATCTTCTTHHHHHHHHHHHHHHH AGTAACAAAGGCATGGAGCATCT | 123 |
| fP-mut16 | ACACGACGCTCTTCCGATCTTCTTHHHHHHHHHHHHHHH GTGGGGTGAGATTTTTGTCAACTT | 124 |
| fP-mut17 | ACACGACGCTCTTCCGATCTTCTTHHHHHHHHHHHHHHH AGCAGTATCAGTAGTATGAGCAGC | 125 |
| fP-mut18 | ACACGACGCTCTTCCGATCTTCTTHHHHHHHHHHHHHHH TTCTGATGTGCTTTGTTCTGGATTT | 126 |
| fP-mut19 | ACACGACGCTCTTCCGATCTTCTTHHHHHHHHHHHHHHH TGAGCCAAATGTGTATGGGTGA | 127 |
| fP-mut20 | ACACGACGCTCTTCCGATCTTCTTHHHHHHHHHHHHHHH GTTGCACATTCCTCTTCTGCATTT | 128 |
| fP-mut21 | ACACGACGCTCTTCCGATCTTCTTHHHHHHHHHHHHHHH GGTGCATTTGTTAACTTCAGCTCTG | 129 |
| fP-mut22 | ACACGACGCTCTTCCGATCTTCTTHHHHHHHHHHHHHHH TAGGTTTCTGCTGTGCCTGAC | 130 |
| fP-mut23 | ACACGACGCTCTTCCGATCTTCTTHHHHHHHHHHHHHHH GGTGGGCTTAGATTTCTACTGACTACTA | 131 |
| fP-mut24 | ACACGACGCTCTTCCGATCTTCTTHHHHHHHHHHHHHHH TCTAGGATTCTCTGAGCATGGC | 132 |
| fP-mut25 | ACACGACGCTCTTCCGATCTTCTTHHHHHHHHHHHHHHH ACTAAATAGGAAAATACCAGCTTCATAGAC | 133 |
| fP-mut26 | ACACGACGCTCTTCCGATCTTCTTHHHHHHHHHHHHHHH ACACTCTTGTGCTGACTTACCA | 134 |
| fP-mut27 | ACACGACGCTCTTCCGATCTTCTTHHHHHHHHHHHHHHH AACATCAGGGAATTCATTTAAAGTAAATAGC | 135 |
| fP-mut28 | ACACGACGCTCTTCCGATCTTCTTHHHHHHHHHHHHHHH GGAACCAAATGATACTGATCCATTAGATTC | 136 |
| fP-mut29 | ACACGACGCTCTTCCGATCTTCTTHHHHHHHHHHHHHHH AGATTCTAAACTGCCAAGTCATGC | 137 |

TABLE 3-continued

Primer sequences in the 179-plex comprehensive panel

| Name | Primer sequence | SEQ ID NO: |
|---|---|---|
| fP-mut30 | ACACGACGCTCTTCCGATCTTCTTHHHHHHHHHHHHHH TGCCTGTAGTAATCAAGTGTCTCATTT | 138 |
| fP-mut31 | ACACGACGCTCTTCCGATCTTCTTHHHHHHHHHHHHHH CAACCAAAGTCTTTGTTCCACCTT | 139 |
| fP-mut32 | ACACGACGCTCTTCCGATCTTCTTHHHHHHHHHHHHHH AGACATCATCTGGATTATACATATTTCGC | 140 |
| fP-mut33 | ACACGACGCTCTTCCGATCTTCTTHHHHHHHHHHHHHH AAAGAGCTAACATACAGTTAGCAGC | 141 |
| fP-mut34 | ACACGACGCTCTTCCGATCTTCTTHHHHHHHHHHHHHH TTCCATTCTAGGACTTGCCCC | 142 |
| fP-mut35 | ACACGACGCTCTTCCGATCTTCTTHHHHHHHHHHHHHH ACTGAATTCTCCTCAGATGACTCC | 143 |
| fP-mut36 | ACACGACGCTCTTCCGATCTTCTTHHHHHHHHHHHHHH ACAGACACTCCTTGTTCAGCA | 144 |
| fP-mut37 | ACACGACGCTCTTCCGATCTTCTTHHHHHHHHHHHHHH TGTGTATATAATTATTTCTTACCCTATTCGAGTC | 145 |
| fP-mut38 | ACACGACGCTCTTCCGATCTTCTTHHHHHHHHHHHHHH TTGCTGTCATTTGGACTGGGAA | 146 |
| fP-mut39 | ACACGACGCTCTTCCGATCTTCTTHHHHHHHHHHHHHH CAAAAAGATACCCACCTTTCCTCCA | 147 |
| fP-mut3new | ACACGACGCTCTTCCGATCTTCTTHHHHHHHHHHHHHH CAATTTCTACACGAGATCCTCTCTCT | 148 |
| fP-mut40 | ACACGACGCTCTTCCGATCTTCTTHHHHHHHHHHHHHH GACATTACGGGCTGCCAAATC | 149 |
| fP-mut41 | ACACGACGCTCTTCCGATCTTCTTHHHHHHHHHHHHHH CTCAGACACACACCCAGCAA | 150 |
| fP-mut42 | ACACGACGCTCTTCCGATCTTCTTHHHHHHHHHHHHHH ACTTACTTTATAAACCGTTCCAAAAGCA | 151 |
| fP-mut43 | ACACGACGCTCTTCCGATCTTCTTHHHHHHHHHHHHHH TGAGTAATGTACTTACTACAATTTTCAGCTT | 152 |
| fP-mut44 | ACACGACGCTCTTCCGATCTTCTTHHHHHHHHHHHHHH GCTGTTGTCAGTAATATAGATGTTTCCTG | 153 |
| fP-mut45 | ACACGACGCTCTTCCGATCTTCTTHHHHHHHHHHHHHH AACTAGGGCAGGCACGC | 154 |
| fP-mut46 | ACACGACGCTCTTCCGATCTTCTTHHHHHHHHHHHHHH GGATAATAAAAGAGAGAAATCACAGACATACAA | 155 |
| fP-mut47 | ACACGACGCTCTTCCGATCTTCTTHHHHHHHHHHHHHH AGGCATATCGATCCTCATAAAGTTTTG | 156 |
| fP-mut48 | ACACGACGCTCTTCCGATCTTCTTHHHHHHHHHHHHHH TCCAGGTTGCCCATGACAAC | 157 |
| fP-mut49 | ACACGACGCTCTTCCGATCTTCTTHHHHHHHHHHHHHH AGTGCCAGAAGGAACCCAC | 158 |
| fP-mut50 | ACACGACGCTCTTCCGATCTTCTTHHHHHHHHHHHHHH AAGTGTTACTCAAGAAGCAGAAAGG | 159 |
| fP-mut51 | ACACGACGCTCTTCCGATCTTCTTHHHHHHHHHHHHHH AAAATCCCTTTGGGTTATAAATAGTGCA | 160 |
| fP-mut52 | ACACGACGCTCTTCCGATCTTCTTHHHHHHHHHHHHHH ATGTGTTTTATAATTTAGACTAGTGAATATTTTTCTTTG | 161 |
| fP-mut53 | ACACGACGCTCTTCCGATCTTCTTHHHHHHHHHHHHHH CTGGAAAAATGGCTTTGAATCTTTGG | 162 |

TABLE 3-continued

Primer sequences in the 179-plex comprehensive panel

| Name | Primer sequence | SEQ ID NO: |
|---|---|---|
| fP-mut54 | ACACGACGCTCTTCCGATCTTCTTHHHHHHHHHHHHHHH TGGAAAAGCTCATTAACTTAACTGACAT | 163 |
| fP-mut55 | ACACGACGCTCTTCCGATCTTCTTHHHHHHHHHHHHHHH TCCTTGGGATTACGCTCCCT | 164 |
| fP-mut56 | ACACGACGCTCTTCCGATCTTCTTHHHHHHHHHHHHHHH ACCCAGTGGAGAAGCTCCC | 165 |
| fP-mut57 | ACACGACGCTCTTCCGATCTTCTTHHHHHHHHHHHHHHH AGGTGAGAAAGTTAAAATTCCCGTC | 166 |
| fP-mut58 | ACACGACGCTCTTCCGATCTTCTTHHHHHHHHHHHHHHH AGGCAGATGCCCAGCAGG | 167 |
| fP-mut59 | ACACGACGCTCTTCCGATCTTCTTHHHHHHHHHHHHHHH CCTCCACCGTGCAGCTCAT | 168 |
| fP-mut60 | ACACGACGCTCTTCCGATCTTCTTHHHHHHHHHHHHHHH AGCCAGGAACGTACTGGTG | 169 |
| fP-mut61 | ACACGACGCTCTTCCGATCTTCTTHHHHHHHHHHHHHHH ACAATGTCACCACATTACATACTTACC | 170 |
| fP-mut62 | ACACGACGCTCTTCCGATCTTCTTHHHHHHHHHHHHHHH ACAGGCTCCCAGACATGACA | 171 |
| fP-mut63 | ACACGACGCTCTTCCGATCTTCTTHHHHHHHHHHHHHHH TTCAGATATTTCTTTCCTTAACTAAAGTACTCA | 172 |
| fP-mut64 | ACACGACGCTCTTCCGATCTTCTTHHHHHHHHHHHHHHH TGTTTGTTTTGTTTTAAGGTTTTTGGATTC | 173 |
| fP-mut65 | ACACGACGCTCTTCCGATCTTCTTHHHHHHHHHHHHHHH TCCTAAGTGCAAAAGATAACTTTATATCACTT | 174 |
| fP-mut66 | ACACGACGCTCTTCCGATCTTCTTHHHHHHHHHHHHHHH GTTGCAGCAATTCACTGTAAAGCT | 175 |
| fP-mut67 | ACACGACGCTCTTCCGATCTTCTTHHHHHHHHHHHHHHH CACAAGAGGCCCTAGATTTCTATGG | 176 |
| fP-mut68 | ACACGACGCTCTTCCGATCTTCTTHHHHHHHHHHHHHHH TTGAGTTCCCTCAGCCGTTAC | 177 |
| fP-mut69 | ACACGACGCTCTTCCGATCTTCTTHHHHHHHHHHHHHHH TCTTCATACCAGGACCAGAGGAA | 178 |
| fP-mut7 | ACACGACGCTCTTCCGATCTTCTTHHHHHHHHHHHHHHH AGTGAGCCCTGCTCCCC | 179 |
| fP-mut70 | ACACGACGCTCTTCCGATCTTCTTHHHHHHHHHHHHHHH GCGTGCAGATAATGACAAGGAATATCT | 180 |
| fP-mut71 | ACACGACGCTCTTCCGATCTTCTTHHHHHHHHHHHHHHH GGTTTTCATTTTAAATTTTCTTTCTCTAGGTGAA | 181 |
| fP-mut72 | ACACGACGCTCTTCCGATCTTCTTHHHHHHHHHHHHHHH TCGTGGCCATGAATGAATTCTCTA | 182 |
| fP-mut73 | ACACGACGCTCTTCCGATCTTCTTHHHHHHHHHHHHHHH TCTACAACAAGCTAACTTTCCAGCT | 183 |
| fP-mut74 | ACACGACGCTCTTCCGATCTTCTTHHHHHHHHHHHHHHH GTGATGTTCCTCCCTCATCTCTAA | 184 |
| fP-mut75 | ACACGACGCTCTTCCGATCTTCTTHHHHHHHHHHHHHHH AGCAACATTGATGGATTTGTGAACT | 185 |
| fP-mut76 | ACACGACGCTCTTCCGATCTTCTTHHHHHHHHHHHHHHH ACGATTGGCTGAAGTACCAGAC | 186 |
| fP-mut77 | ACACGACGCTCTTCCGATCTTCTTHHHHHHHHHHHHHHH TGGACACGACAACAACCAGC | 187 |

TABLE 3-continued

Primer sequences in the 179-plex comprehensive panel

| Name | Primer sequence | SEQ ID NO: |
|---|---|---|
| fP-mut78 | ACACGACGCTCTTCCGATCTTCTTHHHHHHHHHHHHHHH GCAACTTACACGTGGACGAC | 188 |
| fP-mut79 | ACACGACGCTCTTCCGATCTTCTTHHHHHHHHHHHHHHH TCCCTCTTATTGTTCCCTACAGATTG | 189 |
| fP-mut8 | ACACGACGCTCTTCCGATCTTCTTHHHHHHHHHHHHHHH GTGCGCCGGTCTCTCC | 190 |
| fP-mut9 | ACACGACGCTCTTCCGATCTTCTTHHHHHHHHHHHHHHH TGACCTGGAGTCTTCCAGTGT | 191 |
| fP-Ref-1 | ACACGACGCTCTTCCGATCTATCAHHHHHHHHHHHHHHH GCTTGTCTAAGGAAAAAACTTGATTATTTTGTAA | 192 |
| fP-Ref-10 | ACACGACGCTCTTCCGATCTATCAHHHHHHHHHHHHHHH AGGAAGACGCTTGGTTGGG | 193 |
| fP-Ref-11 | ACACGACGCTCTTCCGATCTATCAHHHHHHHHHHHHHHH TGAGACCTATAATGCTAAGGAAATTTCTTTAC | 194 |
| fP-Ref-12 | ACACGACGCTCTTCCGATCTATCAHHHHHHHHHHHHHHH TGGAAGCGTTCGTTCCATCC | 195 |
| fP-Ref-13 | ACACGACGCTCTTCCGATCTATCAHHHHHHHHHHHHHHH GCTTGGCATCTGTTCTTGCTTTAA | 196 |
| fP-Ref-14 | ACACGACGCTCTTCCGATCTATCAHHHHHHHHHHHHHHH AAAATTCTGCAAAAATAAAGGCCAAGA | 197 |
| fP-Ref-15 | ACACGACGCTCTTCCGATCTATCAHHHHHHHHHHHHHHH TTTATTGCATGTCCTCATCCACAG | 198 |
| fP-Ref-16 | ACACGACGCTCTTCCGATCTATCAHHHHHHHHHHHHHHH ATTGGGGATGTCCAGAATAAATTCAG | 199 |
| fP-Ref-17 | ACACGACGCTCTTCCGATCTATCAHHHHHHHHHHHHHHH CAAACAGTTCAGTGACTTGCCC | 200 |
| fP-Ref-18 | ACACGACGCTCTTCCGATCTATCAHHHHHHHHHHHHHHH CAGGCATCTCACCTCTCTTCC | 201 |
| fP-Ref-19 | ACACGACGCTCTTCCGATCTATCAHHHHHHHHHHHHHHH GGCATTATTCCAGTATTGTAGAAGAAGAA | 202 |
| fP-Ref-2 | ACACGACGCTCTTCCGATCTATCAHHHHHHHHHHHHHHH CTACATTACCAGTAGAACAGAACTAGTCTA | 203 |
| fP-Ref-20 | ACACGACGCTCTTCCGATCTATCAHHHHHHHHHHHHHHH GCTAACCGTGCTTTCCTCTTTCAT | 204 |
| fP-Ref-21 | ACACGACGCTCTTCCGATCTATCAHHHHHHHHHHHHHHH CCCTAGCAGAAGCCGACCA | 205 |
| fP-Ref-22 | ACACGACGCTCTTCCGATCTATCAHHHHHHHHHHHHHHH CAAACCACCACTTATTTCTTTATTTTATCCT | 206 |
| fP-Ref-23 | ACACGACGCTCTTCCGATCTATCAHHHHHHHHHHHHHHH TCATTTTGTAGTCATTGTAAAACTCTTATGC | 207 |
| fP-Ref-24 | ACACGACGCTCTTCCGATCTATCAHHHHHHHHHHHHHHH AGAGTAGCGACATGCAAATGATCT | 208 |
| fP-Ref-25 | ACACGACGCTCTTCCGATCTATCAHHHHHHHHHHHHHHH CCCAGCATTTGTTATATAGGCATCTT | 209 |
| fP-Ref-26 | ACACGACGCTCTTCCGATCTATCAHHHHHHHHHHHHHHH GAGTAGACAGGGAAATATAGAAGCCT | 210 |
| fP-Ref-27 | ACACGACGCTCTTCCGATCTATCAHHHHHHHHHHHHHHH CCATCCTTTTTAGTGCTGTCCTCA | 211 |
| fP-Ref-28 | ACACGACGCTCTTCCGATCTATCAHHHHHHHHHHHHHHH TCAGCTGGCCTAGCAGTTC | 212 |

TABLE 3-continued

Primer sequences in the 179-plex comprehensive panel

| Name | Primer sequence | SEQ ID NO: |
|---|---|---|
| fP-Ref-29 | ACACGACGCTCTTCCGATCTATCAHHHHHHHHHHHHHHH GCATAATTTATAATGAAAACAAATACATTCTCACAG | 213 |
| fP-Ref-3 | ACACGACGCTCTTCCGATCTATCAHHHHHHHHHHHHHHH CTTATTTGCATTTGTGGCATAATATGAAAC | 214 |
| fP-Ref-30 | ACACGACGCTCTTCCGATCTATCAHHHHHHHHHHHHHHH CTAGGGTTAGTCAGGTGGTTCAA | 215 |
| fP-Ref-31 | ACACGACGCTCTTCCGATCTATCAHHHHHHHHHHHHHHH CAGAAGGGCTCTCACTGGG | 216 |
| fP-Ref-32 | ACACGACGCTCTTCCGATCTATCAHHHHHHHHHHHHHHH GCCTTATATTATTCCCTTTGAACCTTACAATAAT | 217 |
| fP-Ref-33 | ACACGACGCTCTTCCGATCTATCAHHHHHHHHHHHHHHH CCTGCAGCGGGAGTTTTCA | 218 |
| fP-Ref-34 | ACACGACGCTCTTCCGATCTATCAHHHHHHHHHHHHHHH CGGCGCCACGTGTTCA | 219 |
| fP-Ref-35 | ACACGACGCTCTTCCGATCTATCAHHHHHHHHHHHHHHH TGGCCCATTTTAACCTTTTTTTTTTAAAGTA | 220 |
| fP-Ref-36 | ACACGACGCTCTTCCGATCTATCAHHHHHHHHHHHHHHH TGTGAACAGCCAGAAGCGAT | 221 |
| fP-Ref-37 | ACACGACGCTCTTCCGATCTATCAHHHHHHHHHHHHHHH CCAGCCCCTGATCCTACCAG | 222 |
| fP-Ref-38 | ACACGACGCTCTTCCGATCTATCAHHHHHHHHHHHHHHH AGTAACTGAACGACGAATTCTTTGTAA | 223 |
| fP-Ref-39 | ACACGACGCTCTTCCGATCTATCAHHHHHHHHHHHHHHH CAGCTCCCACCACAGTGC | 224 |
| fP-Ref-4 | ACACGACGCTCTTCCGATCTATCAHHHHHHHHHHHHHHH CACACAGCGGGCTCTCA | 225 |
| fP-Ref-40 | ACACGACGCTCTTCCGATCTATCAHHHHHHHHHHHHHHH TCCCTTCTCCTACACTTCCTCC | 226 |
| fP-Ref-41 | ACACGACGCTCTTCCGATCTATCAHHHHHHHHHHHHHHH ACTACAGGAGCAACTGCCAC | 227 |
| fP-Ref-42 | ACACGACGCTCTTCCGATCTATCAHHHHHHHHHHHHHHH AGAGGTAGGGATTATTAGCCCCAT | 228 |
| fP-Ref-43 | ACACGACGCTCTTCCGATCTATCAHHHHHHHHHHHHHHH TGTGTATCCAACAGGAACTCCAAA | 229 |
| fP-Ref-44 | ACACGACGCTCTTCCGATCTATCAHHHHHHHHHHHHHHH CTGGTCTTAAAATGTCCTGGGGA | 230 |
| fP-Ref-45 | ACACGACGCTCTTCCGATCTATCAHHHHHHHHHHHHHHH ACGCCCGGCCATCTCA | 231 |
| fP-Ref-46 | ACACGACGCTCTTCCGATCTATCAHHHHHHHHHHHHHHH TTTTCACTGTTTCCTACAAGAAAATGC | 232 |
| fP-Ref-47 | ACACGACGCTCTTCCGATCTATCAHHHHHHHHHHHHHHH GAAACCTGGATTTTTGAAATCTAGTGTTTAA | 233 |
| fP-Ref-48 | ACACGACGCTCTTCCGATCTATCAHHHHHHHHHHHHHHH GCAAGGACGGAAATAGGTAAATGT | 234 |
| fP-Ref-49 | ACACGACGCTCTTCCGATCTATCAHHHHHHHHHHHHHHH CGAGGCACTGCGTTTGG | 235 |
| fP-Ref-5 | ACACGACGCTCTTCCGATCTATCAHHHHHHHHHHHHHHH AGCAGATGGGTTGAGAGTTGG | 236 |
| fP-Ref-50 | ACACGACGCTCTTCCGATCTATCAHHHHHHHHHHHHHHH TCCAATCTCTATCTGTTAGAAGTCTCC | 237 |

TABLE 3-continued

Primer sequences in the 179-plex comprehensive panel

| Name | Primer sequence | SEQ ID NO: |
|---|---|---|
| fP-Ref-6 | ACACGACGCTCTTCCGATCTATCAHHHHHHHHHHHHHHH GGCTCTGATTTCCGCCCAAT | 238 |
| fP-Ref-7 | ACACGACGCTCTTCCGATCTATCAHHHHHHHHHHHHHHH TGCAAAGATTGTAGGAGCTCTGTA | 239 |
| fP-Ref-8 | ACACGACGCTCTTCCGATCTATCAHHHHHHHHHHHHHHH AATTAGATAAAAAGCATCCACAGAGGAG | 240 |
| fP-Ref-9 | ACACGACGCTCTTCCGATCTATCAHHHHHHHHHHHHHHH AGTCTTTAACAATGAGAGTCAAACCATT | 241 |
| rPin-ERBB2-1 | AGACGTGTGCTCTTCCGATCTGTGCAGGGGGCAGACGA | 242 |
| rPin-ERBB2-10 | AGACGTGTGCTCTTCCGATCTCCCCTCACAACAACCAGA CG | 243 |
| rPin-ERBB2-11 | AGACGTGTGCTCTTCCGATCTATGTTCTAACACCGTGAT CTGGAT | 244 |
| rPin-ERBB2-12 | AGACGTGTGCTCTTCCGATCTTGGAAAACACTTCAGTTT GCTCATTAA | 245 |
| rPin-ERBB2-13 | AGACGTGTGCTCTTCCGATCTGCAAAGGTTCTACCCCGC AT | 246 |
| rPin-ERBB2-14 | AGACGTGTGCTCTTCCGATCTGGCTACTTCTTACTCATT CCAACCC | 247 |
| rPin-ERBB2-15 | AGACGTGTGCTCTTCCGATCTCCATCACCAGCTAGTCTG AGTC | 248 |
| rPin-ERBB2-16 | AGACGTGTGCTCTTCCGATCTCCCCGTTTTATCTGTGAC TCTTTG | 249 |
| rPin-ERBB2-17 | AGACGTGTGCTCTTCCGATCTCCATCCTCTCTGCATCCC AAATC | 250 |
| rPin-ERBB2-18 | AGACGTGTGCTCTTCCGATCTGGCAGGTGTTATCATTCC CCATTT | 251 |
| rPin-ERBB2-19 | AGACGTGTGCTCTTCCGATCTGGGCCTCCTTATTTTTAT GTGCTAAAT | 252 |
| rPin-ERBB2-2 | AGACGTGTGCTCTTCCGATCTAGGGTGGAGGGGCTTACG | 253 |
| rPin-ERBB2-20 | AGACGTGTGCTCTTCCGATCTAGCTTGCATCCTACTCCA TCC | 254 |
| rPin-ERBB2-21 | AGACGTGTGCTCTTCCGATCTTCCCCTGGTTTCTCCGGT | 255 |
| rPin-ERBB2-22 | AGACGTGTGCTCTTCCGATCTCGACCCCGCCAGAAGC | 256 |
| rPin-ERBB2-23 | AGACGTGTGCTCTTCCGATCTGCATGCAAAACACCACAA ACAGTT | 257 |
| rPin-ERBB2-24 | AGACGTGTGCTCTTCCGATCTGGCTACCTCCCTCTGTTT ATGG | 258 |
| rPin-ERBB2-25 | AGACGTGTGCTCTTCCGATCTAAAATATGAAGGAGTTCT GCAAGATTAAAAG | 259 |
| rPin-ERBB2-26 | AGACGTGTGCTCTTCCGATCTGGTTCATACAGCAGGAAT ATGGGTAAT | 260 |
| rPin-ERBB2-27 | AGACGTGTGCTCTTCCGATCTAGGACAGGCACAACTACC CT | 261 |
| rPin-ERBB2-28 | AGACGTGTGCTCTTCCGATCTAGCAGAAAAGCCAATACT TCCCT | 262 |
| rPin-ERBB2-29 | AGACGTGTGCTCTTCCGATCTAACACCACAGGCTCTACG G | 263 |

TABLE 3-continued

Primer sequences in the 179-plex comprehensive panel

| Name | Primer sequence | SEQ ID NO: |
|---|---|---|
| rPin-ERBB2-3 | AGACGTGTGCTCTTCCGATCTCCCAGAAGGCGGGAGACATA | 264 |
| rPin-ERBB2-30 | AGACGTGTGCTCTTCCGATCTCAGGGAGAAGCCTGACTGAAG | 265 |
| rPin-ERBB2-31 | AGACGTGTGCTCTTCCGATCTGGTGGACAGGGGACATGATCA | 266 |
| rPin-ERBB2-32 | AGACGTGTGCTCTTCCGATCTGGAACACTGCCACCCCC | 267 |
| rPin-ERBB2-33 | AGACGTGTGCTCTTCCGATCTCCCCCTGGTTAGCAGTGG | 268 |
| rPin-ERBB2-34 | AGACGTGTGCTCTTCCGATCTAACTCAGCCCCATCACTCAC | 269 |
| rPin-ERBB2-35 | AGACGTGTGCTCTTCCGATCTGGAGGGGCATGGCTTACAG | 270 |
| rPin-ERBB2-36 | AGACGTGTGCTCTTCCGATCTCGGCTCTGACAATCCTCAGAA | 271 |
| rPin-ERBB2-37 | AGACGTGTGCTCTTCCGATCTGGTCTCAAAAACAAAACGAAAGGTAAA | 272 |
| rPin-ERBB2-38 | AGACGTGTGCTCTTCCGATCTACTGACAGGGGATATAGGGACA | 273 |
| rPin-ERBB2-39 | AGACGTGTGCTCTTCCGATCTAGTCCTTGTTCACGGATAGCAT | 274 |
| rPin-ERBB2-4 | AGACGTGTGCTCTTCCGATCTGTTCCGAGCGGCCAAGTC | 275 |
| rPin-ERBB2-40 | AGACGTGTGCTCTTCCGATCTCCGCAGGGGACTTTTAGGG | 276 |
| rPin-ERBB2-41 | AGACGTGTGCTCTTCCGATCTCTAGCACAGCCACAGTCACA | 277 |
| rPin-ERBB2-42 | AGACGTGTGCTCTTCCGATCTCATTTAGTTGTCTTTAAATTGAAATGCATGAA | 278 |
| rPin-ERBB2-43 | AGACGTGTGCTCTTCCGATCTCCTTGTCATCCAGGTCCACA | 279 |
| rPin-ERBB2-44 | AGACGTGTGCTCTTCCGATCTACTCTAACTTGACCCCCTTATTCCT | 280 |
| rPin-ERBB2-45 | AGACGTGTGCTCTTCCGATCTACAGGAATGTACACCTGATGATTTTG | 281 |
| rPin-ERBB2-46 | AGACGTGTGCTCTTCCGATCTCTGCCTTGGCTCCCCG | 282 |
| rPin-ERBB2-47 | AGACGTGTGCTCTTCCGATCTCAGTCTCCGCATCGTGTACT | 283 |
| rPin-ERBB2-48 | AGACGTGTGCTCTTCCGATCTCTGTGCCCAGCTTAATTTTGTACA | 284 |
| rPin-ERBB2-49 | AGACGTGTGCTCTTCCGATCTGGGGTGTCAAGTACTCGGG | 285 |
| rPin-ERBB2-5 | AGACGTGTGCTCTTCCGATCTACACATCACTCTGGTGGGTGAA | 286 |
| rPin-ERBB2-50 | AGACGTGTGCTCTTCCGATCTTGGACCCCTTCCAGCCA | 287 |
| rPin-ERBB2-6 | AGACGTGTGCTCTTCCGATCTCTCTCGGTGGATCTGCATAACAT | 288 |
| rPin-ERBB2-7 | AGACGTGTGCTCTTCCGATCTGTCAAATCCTAGGGGGTAATACGA | 289 |

TABLE 3-continued

Primer sequences in the 179-plex comprehensive panel

| Name | Primer sequence | SEQ ID NO: |
|---|---|---|
| rPin-ERBB2-8 | AGACGTGTGCTCTTCCGATCTCTGGTCATTGCAGAGACC TCT | 290 |
| rPin-ERBB2-9 | AGACGTGTGCTCTTCCGATCTTCTCCATTGTCTAGCACG GC | 291 |
| rPin-Mut1 | AGACGTGTGCTCTTCCGATCTCTCACAGTAAAAATAGGT GATTTTGGTCT | 292 |
| rPin-Mut2 | AGACGTGTGCTCTTCCGATCTAAGATCCAATCCATTTTT GTTGTCCAG | 293 |
| rPin-Mut4 | AGACGTGTGCTCTTCCGATCTGTCTGACGGGTAGAGTGT GC | 294 |
| rPin-Mut5 | AGACGTGTGCTCTTCCGATCTCACATGACGGAGGTTGTG AGG | 295 |
| rPin-Mut6 | AGACGTGTGCTCTTCCGATCTCTGAAAATGACTGAATAT AAACTTGTGGTAGT | 296 |
| rPin-mut10 | AGACGTGTGCTCTTCCGATCTCCAGTTGCAAACCAGACC TCA | 297 |
| rPin-mut11 | AGACGTGTGCTCTTCCGATCTTCCTCACTGATTGCTCTT AGGTCT | 298 |
| rPin-mut12 | AGACGTGTGCTCTTCCGATCTCCAACAAGGCACTGACCA TC | 299 |
| rPin-mut13 | AGACGTGTGCTCTTCCGATCTGAGCGCCAGACGAGACC | 300 |
| rPin-mut14 | AGACGTGTGCTCTTCCGATCTCGGTGGATATGGTCCTTC TCTTC | 301 |
| rPin-mut15 | AGACGTGTGCTCTTCCGATCTCGGTGGGCGTCCAGCA | 302 |
| rPin-mut16 | AGACGTGTGCTCTTCCGATCTTGGTCAATGGAAGAAACC ACCA | 303 |
| rPin-mut17 | AGACGTGTGCTCTTCCGATCTCATCTTCAACCTCTGCAT TGAAAGT | 304 |
| rPin-mut18 | AGACGTGTGCTCTTCCGATCTAACAGCTACCCTTCCATC ATAAGT | 305 |
| rPin-mut19 | AGACGTGTGCTCTTCCGATCTCTGTTTTTAGCAAAAGCG TCCAG | 306 |
| rPin-mut20 | AGACGTGTGCTCTTCCGATCTAGGTTTCAAAGCGCCAGT CA | 307 |
| rPin-mut21 | AGACGTGTGCTCTTCCGATCTGTAACAAGCCAAATGAAC AGACAAGT | 308 |
| rPin-mut22 | AGACGTGTGCTCTTCCGATCTAGTTGTTCTAGCAGTGAA GAGATAAAGA | 309 |
| rPin-mut23 | AGACGTGTGCTCTTCCGATCTAAAGCACCTAAAAAGAAT AGGCTGAG | 310 |
| rPin-mut24 | AGACGTGTGCTCTTCCGATCTAGGTAGATCTGAATGCTG ATCCC | 311 |
| rPin-mut25 | AGACGTGTGCTCTTCCGATCTGGATCTGATTCTTCTGAA GATACCGTTAA | 312 |
| rPin-mut26 | AGACGTGTGCTCTTCCGATCTGATTTATCTGCTCTTCGC GTTGAA | 313 |
| rPin-mut27 | AGACGTGTGCTCTTCCGATCTACTGTTTCATATACTTCA TCTTCTAGGACA | 314 |

TABLE 3-continued

Primer sequences in the 179-plex comprehensive panel

| Name | Primer sequence | SEQ ID NO: |
|---|---|---|
| rPin-mut28 | AGACGTGTGCTCTTCCGATCTGGAGATTTTGTCACTTCC ACTCTC | 315 |
| rPin-mut29 | AGACGTGTGCTCTTCCGATCTTTGAATTTGACAAAACCA TTTCCTCATTT | 316 |
| rPin-mut30 | AGACGTGTGCTCTTCCGATCTGTTTCAGGACATCCATTT TATCAAGTTTC | 317 |
| rPin-mut31 | AGACGTGTGCTCTTCCGATCTGTTAATATTCCTAACACA CTGTTCAACTCT | 318 |
| rPin-mut32 | AGACGTGTGCTCTTCCGATCTTTCTAGTCTCTTTTGTTG GGCCT | 319 |
| rPin-mut33 | AGACGTGTGCTCTTCCGATCTCTTATCAAAACTGAAAAA TTACAATGAAAGGTTT | 320 |
| rPin-mut34 | AGACGTGTGCTCTTCCGATCTCTTTATTGCCAGTAAATT GTAACATTCGT | 321 |
| rPin-mut35 | AGACGTGTGCTCTTCCGATCTCAAGTTCTTCGTCAGCTA TTGAATTACT | 322 |
| rPin-mut36 | AGACGTGTGCTCTTCCGATCTCCTTCTCTCCACATATGT TTCTCTTATTAA | 323 |
| rPin-mut37 | AGACGTGTGCTCTTCCGATCTCATCCCACCTCCCATCTA TACTTC | 324 |
| rPin-mut38 | AGACGTGTGCTCTTCCGATCTTTTGTGTCTGATGGGCAA TCTTTC | 325 |
| rPin-mut39 | AGACGTGTGCTCTTCCGATCTTTTTGGGCTAGCCAGACT CTTG | 326 |
| rPin-mut3new | AGACGTGTGCTCTTCCGATCTGAATCTCCATTTTAGCAC TTACCTGTG | 327 |
| rPin-mut40 | AGACGTGTGCTCTTCCGATCTTTGATATTTTTCAGGGAA TGATGTACCTG | 328 |
| rPin-mut41 | AGACGTGTGCTCTTCCGATCTGAAATCATGGTATTGCAT TTTTTTCTTACAG | 329 |
| rPin-mut42 | AGACGTGTGCTCTTCCGATCTAGCACCCAATCAAGCTCA ACT | 330 |
| rPin-mut43 | AGACGTGTGCTCTTCCGATCTACTCTTCAGCACAATCAA CCAGA | 331 |
| rPin-mut44 | AGACGTGTGCTCTTCCGATCTGCATCACCTCTCTACAGT TCCAGT | 332 |
| rPin-mut45 | AGACGTGTGCTCTTCCGATCTGCTGAATGTTAACATTAA TGCTTATTTTACC | 333 |
| rPin-mut46 | AGACGTGTGCTCTTCCGATCTAGTGACTGCTGCCATCGA G | 334 |
| rPin-mut47 | AGACGTGTGCTCTTCCGATCTGCTACGTGTTAGTGGCTC TTAATCA | 335 |
| rPin-mut48 | AGACGTGTGCTCTTCCGATCTATAAACTGAGCTCTCTCT CTGACC | 336 |
| rPin-mut49 | AGACGTGTGCTCTTCCGATCTTGAAGCCGGCGACAGG | 337 |
| rPin-mut50 | AGACGTGTGCTCTTCCGATCTGGTTCAATTACTTTTAAA AAGGGTTGAAAAAG | 338 |
| rPin-mut51 | AGACGTGTGCTCTTCCGATCTATTTGACTTTACCTTATC AATGTCTCGAA | 339 |

TABLE 3-continued

Primer sequences in the 179-plex comprehensive panel

| Name | Primer sequence | SEQ ID NO: |
|---|---|---|
| rPin-mut52 | AGACGTGTGCTCTTCCGATCTGTGTCTGTGTAATCAAAC AAGTTTATATTTCC | 340 |
| rPin-mut53 | AGACGTGTGCTCTTCCGATCTAGTAACACCAATAGGGTT CAGCAA | 341 |
| rPin-mut54 | AGACGTGTGCTCTTCCGATCTAAAGAGTCTCAAACACAA ACTAGAGTC | 342 |
| rPin-mut55 | AGACGTGTGCTCTTCCGATCTTTTATTGTATTTGCATAG CACAAATTTTTGTT | 343 |
| rPin-mut56 | AGACGTGTGCTCTTCCGATCTCCGTGCCGAACGCACC | 344 |
| rPin-mut57 | AGACGTGTGCTCTTCCGATCTGCAAAGCAGAAACTCACA TCGA | 345 |
| rPin-mut58 | AGACGTGTGCTCTTCCGATCTCTCCAGGAAGCCTACGTG ATG | 346 |
| rPin-mut59 | AGACGTGTGCTCTTCCGATCTCGGACATAGTCCAGGAGG CAG | 347 |
| rPin-mut60 | AGACGTGTGCTCTTCCGATCTGCATGGTATTCTTTCTCT TCCGCA | 348 |
| rPin-mut61 | AGACGTGTGCTCTTCCGATCTGGGCAGATTACAGTGGGA CAA | 349 |
| rPin-mut62 | AGACGTGTGCTCTTCCGATCTGGATACAGGTCAAGTCTA AGTCGAATC | 350 |
| rPin-mut63 | AGACGTGTGCTCTTCCGATCTCCTGTATACGCCTTCAAG TCTTTCT | 351 |
| rPin-mut64 | AGACGTGTGCTCTTCCGATCTGCAAGCATACAAATAAGA AAACATACTTACAG | 352 |
| rPin-mut65 | AGACGTGTGCTCTTCCGATCTTCTGCAATTAAATTTGGC GGTGT | 353 |
| rPin-mut66 | AGACGTGTGCTCTTCCGATCTCGATGTAATAAATATGCA CATATCATTACACC | 354 |
| rPin-mut67 | AGACGTGTGCTCTTCCGATCTCAGGAAGAGGAAAGGAAA AACATCAA | 355 |
| rPin-mut68 | AGACGTGTGCTCTTCCGATCTGATATTTCTCCCAATGAA AGTAAAGTACAAAC | 356 |
| rPin-mut69 | AGACGTGTGCTCTTCCGATCTTCGATTTCTTGATCACAT AGACTTCCAT | 357 |
| rPin-mut7 | AGACGTGTGCTCTTCCGATCTGGGCGTGAGCGCTTCG | 358 |
| rPin-mut70 | AGACGTGTGCTCTTCCGATCTCTTAAAATTTGGAGAAAA GTATCGGTTGG | 359 |
| rPin-mut71 | AGACGTGTGCTCTTCCGATCTAGCCTCTGGATTTGACGG C | 360 |
| rPin-mut72 | AGACGTGTGCTCTTCCGATCTGATGGCAAACTTCCCATC GTAG | 361 |
| rPin-mut73 | AGACGTGTGCTCTTCCGATCTGGGACAGCTGGCTACACA A | 362 |
| rPin-mut74 | AGACGTGTGCTCTTCCGATCTAGGCCCTGACACAGGATG T | 363 |
| rPin-mut75 | AGACGTGTGCTCTTCCGATCTCCCATTGAGGCCGGTGAT | 364 |
| rPin-mut76 | AGACGTGTGCTCTTCCGATCTTTGACCATCACCATGTAG ACATCA | 365 |

TABLE 3-continued

Primer sequences in the 179-plex comprehensive panel

| Name | Primer sequence | SEQ ID NO: |
|---|---|---|
| rPin-mut77 | AGACGTGTGCTCTTCCGATCTAGCTGTCTCTCTCCCAGTTCATT | 366 |
| rPin-mut78 | AGACGTGTGCTCTTCCGATCTCCCATGGCAAACACCATGAG | 367 |
| rPin-mut79 | AGACGTGTGCTCTTCCGATCTCACCATGTGTGACTTGATTAGCAG | 368 |
| rPin-mut8 | AGACGTGTGCTCTTCCGATCTGTGGTAATCTACTGGGACGGAAC | 369 |
| rPin-mut9 | AGACGTGTGCTCTTCCGATCTTCCACTACAACTACATGTGTAACAGTT | 370 |
| rPin-Ref-1 | AGACGTGTGCTCTTCCGATCTGTAACAGTAGGTGTTTCAATATGACTTTTATT | 371 |
| rPin-Ref-10 | AGACGTGTGCTCTTCCGATCTCTCCCCTCCTCCATAGGAACTT | 372 |
| rPin-Ref-11 | AGACGTGTGCTCTTCCGATCTACATACCAGGTTCTGCGCTT | 373 |
| rPin-Ref-12 | AGACGTGTGCTCTTCCGATCTATCAAGGCACCGCTCTAACTT | 374 |
| rPin-Ref-13 | AGACGTGTGCTCTTCCGATCTATCCCGGTGTGCATTTGAGA | 375 |
| rPin-Ref-14 | AGACGTGTGCTCTTCCGATCTGGGCTATGGGGGCTTCCT | 376 |
| rPin-Ref-15 | AGACGTGTGCTCTTCCGATCTGATGTGCCCTGACATCAGAAATATAC | 377 |
| rPin-Ref-16 | AGACGTGTGCTCTTCCGATCTAGTGTTGATCTGAAGGAACTTCCT | 378 |
| rPin-Ref-17 | AGACGTGTGCTCTTCCGATCTTGGGACCATGTTTGGCCAT | 379 |
| rPin-Ref-18 | AGACGTGTGCTCTTCCGATCTTCCCATCATTGCTGCTGTCA | 380 |
| rPin-Ref-19 | AGACGTGTGCTCTTCCGATCTCAAACACGTGTGATCAATAGTACCAT | 381 |
| rPin-Ref-2 | AGACGTGTGCTCTTCCGATCTTCTCATATCAGAACTTAAATACATAGCAGTAG | 382 |
| rPin-Ref-20 | AGACGTGTGCTCTTCCGATCTGGGGAAGGAAGATGTCACATTATGA | 383 |
| rPin-Ref-21 | AGACGTGTGCTCTTCCGATCTGCATGCGCAAGAGCTACCC | 384 |
| rPin-Ref-22 | AGACGTGTGCTCTTCCGATCTACGATAAAATTCTCTTATCTTGAAGGATTGAT | 385 |
| rPin-Ref-23 | AGACGTGTGCTCTTCCGATCTAGTGTTTCTGATATTGAAAAATTTTAAGTGCT | 386 |
| rPin-Ref-24 | AGACGTGTGCTCTTCCGATCTTTTCATCCTTCGCACATGTATACTG | 387 |
| rPin-Ref-25 | AGACGTGTGCTCTTCCGATCTCTGGAGCAGATGACTCACATTTC | 388 |
| rPin-Ref-26 | AGACGTGTGCTCTTCCGATCTAGGGGGCTTGGTCTTTTTTCT | 389 |
| rPin-Ref-27 | AGACGTGTGCTCTTCCGATCTCACCTTTTTTAACAACCGGATCTAGT | 390 |

TABLE 3-continued

Primer sequences in the 179-plex comprehensive panel

| Name | Primer sequence | SEQ ID NO: |
|---|---|---|
| rPin-Ref-28 | AGACGTGTGCTCTTCCGATCTGAGGCCCTGTAATCTGTATTTTAACC | 391 |
| rPin-Ref-29 | AGACGTGTGCTCTTCCGATCTCCTTAATATCAGACTTCCCAGCCTTC | 392 |
| rPin-Ref-3 | AGACGTGTGCTCTTCCGATCTGGAGCTCTGAGACAGGAACC | 393 |
| rPin-Ref-30 | AGACGTGTGCTCTTCCGATCTTGGCAAAGCAGAAGACAATAGTAGA | 394 |
| rPin-Ref-31 | AGACGTGTGCTCTTCCGATCTCCCTTTCAGGGAGTCCTGTACA | 395 |
| rPin-Ref-32 | AGACGTGTGCTCTTCCGATCTTTTTCGTTACTGTAAAATGGGAATGTTC | 396 |
| rPin-Ref-33 | AGACGTGTGCTCTTCCGATCTCGGTGAACTTTCGGGAAAGG | 397 |
| rPin-Ref-34 | AGACGTGTGCTCTTCCGATCTCCCACGTACAAGAGGATTTCAAAGT | 398 |
| rPin-Ref-35 | AGACGTGTGCTCTTCCGATCTAGTGTGAATGTACTTAATGACACTTAGC | 399 |
| rPin-Ref-36 | AGACGTGTGCTCTTCCGATCTGTGAGGCAGGTGCTCACTT | 400 |
| rPin-Ref-37 | AGACGTGTGCTCTTCCGATCTCTGGTGTTCTTTTATACCCATTTTTTCTTTA | 401 |
| rPin-Ref-38 | AGACGTGTGCTCTTCCGATCTCTGTTGCTCTTGACTCTGAGCT | 402 |
| rPin-Ref-39 | AGACGTGTGCTCTTCCGATCTCCTCAGGTCCTTGTGGCTAAC | 403 |
| rPin-Ref-4 | AGACGTGTGCTCTTCCGATCTAGGAGCCGTGGGAATCAAAA | 404 |
| rPin-Ref-40 | AGACGTGTGCTCTTCCGATCTCAGCATGGCAAGGCAACTT | 405 |
| rPin-Ref-41 | AGACGTGTGCTCTTCCGATCTTGAGGGACAGAAAATCAGGTCG | 406 |
| rPin-Ref-42 | AGACGTGTGCTCTTCCGATCTGGCTAATGAGTTGATCTCTCTGAGC | 407 |
| rPin-Ref-43 | AGACGTGTGCTCTTCCGATCTAAAAGAAAACAAAGGACATAGATTTTCCC | 408 |
| rPin-Ref-44 | AGACGTGTGCTCTTCCGATCTAGAGTGCTCAAACCTTGGGAA | 409 |
| rPin-Ref-45 | AGACGTGTGCTCTTCCGATCTGCTATCATGCCATGAAGAATATTCATATATTCATA | 410 |
| rPin-Ref-46 | AGACGTGTGCTCTTCCGATCTAGAGAACCCACTTGGGACCA | 411 |
| rPin-Ref-47 | AGACGTGTGCTCTTCCGATCTACCATATTCTTAATTTTTAAAATTCACAGCCA | 412 |
| rPin-Ref-48 | AGACGTGTGCTCTTCCGATCTCTCTGTCGTAAGTCAAGTCTTTGTG | 413 |
| rPin-Ref-49 | AGACGTGTGCTCTTCCGATCTCTATCGAATCAGAATGCAAAGCAAATT | 414 |
| rPin-Ref-5 | AGACGTGTGCTCTTCCGATCTCGTTTCGGATACTCAGTCTCTGAA | 415 |

TABLE 3-continued

Primer sequences in the 179-plex comprehensive panel

| Name | Primer sequence | SEQ ID NO: |
|---|---|---|
| rPin-Ref-50 | AGACGTGTGCTCTTCCGATCTACAAATTACCTAAACTGACTCAAGAAGAA | 416 |
| rPin-Ref-6 | AGACGTGTGCTCTTCCGATCTGGCTCCTTTCGTGAGCGAAG | 417 |
| rPin-Ref-7 | AGACGTGTGCTCTTCCGATCTAGAGGTAGTGGAGGTCAAGGT | 418 |
| rPin-Ref-8 | AGACGTGTGCTCTTCCGATCTTGACTTGCGTTCATCTTGTTATTTAAAC | 419 |
| rPin-Ref-9 | AGACGTGTGCTCTTCCGATCTCCTGAAAAGGTAGGTTGGTGC | 420 |
| rPout-ERBB2-1 | GGATATTCCTTTCTACTCTTTGACATCATCTTCACCTCTTGGTTGTGCAGG | 421 |
| rPout-ERBB2-10 | GGATATTCCTTTCTACTCTTTGACATCATCTCATTTACCCCTCACAACAACCAG | 422 |
| rPout-ERBB2-11 | GGATATTCCTTTCTACTCTTTGACATCATCTCCATGTTCTAACACCGTGATCTG | 423 |
| rPout-ERBB2-12 | GGATATTCCTTTCTACTCTTTGACATCATCTCATGGAAAACACTTCAGTTTGCTC | 424 |
| rPout-ERBB2-13 | GGATATTCCTTTCTACTCTTTGACATCATCTACAGCAAAGGTTCTACCCCG | 425 |
| rPout-ERBB2-14 | GGATATTCCTTTCTACTCTTTGACATCATCTCCAGGCTACTTCTTACTCATTCCAA | 426 |
| rPout-ERBB2-15 | GGATATTCCTTTCTACTCTTTGACATCATCTACCTCCATCACCAGCTAGTCT | 427 |
| rPout-ERBB2-16 | GGATATTCCTTTCTACTCTTTGACATCATCTGGTGCCCCCGTTTTATCTGT | 428 |
| rPout-ERBB2-17 | GGATATTCCTTTCTACTCTTTGACATCATCTCCAAGCAAACCCATCCTCTCTG | 429 |
| rPout-ERBB2-18 | GGATATTCCTTTCTACTCTTTGACATCATCTAGGAGGCAGGTGTTATCATTCC | 430 |
| rPout-ERBB2-19 | GGATATTCCTTTCTACTCTTTGACATCATCTTTTATCTGAAATTCAAATTTAACTGGGCC | 431 |
| rPout-ERBB2-2 | GGATATTCCTTTCTACTCTTTGACATCATCTGGAGAGGGTGGAGGGGCT | 432 |
| rPout-ERBB2-20 | GGATATTCCTTTCTACTCTTTGACATCATCTGGGGAGCTTGCATCCTACTC | 433 |
| rPout-ERBB2-21 | GGATATTCCTTTCTACTCTTTGACATCATCTGGCTCCCCTGGTTTCTCC | 434 |
| rPout-ERBB2-22 | GGATATTCCTTTCTACTCTTTGACATCATCTACACCCGACCCCGCC | 435 |
| rPout-ERBB2-23 | GGATATTCCTTTCTACTCTTTGAcATcATcTTGTTCTAGGATTAAAGGAGAATGCATG | 436 |
| rPout-ERBB2-24 | GGATATTCCTTTCTACTCTTTGACATCATCTCCATAGAAGGCTACCTCCCTCT | 437 |
| rPout-ERBB2-25 | GGATATTCCTTTCTACTCTTTGACATCATCTGGAATTAAAATATGAAGGAGTTCTGCAAG | 438 |
| rPout-ERBB2-26 | GGATATTCCTTTCTACTCTTTGACATCATCTTTAAAAGTTAAGACAAGACAGGTTCATACA | 439 |
| rPout-ERBB2-27 | GGATATTCCTTTCTACTCTTTGACATCATCTCCCAAGGACAGGCACAACTAC | 440 |

TABLE 3-continued

Primer sequences in the 179-plex comprehensive panel

| Name | Primer sequence | SEQ ID NO: |
|---|---|---|
| rPout-ERBB2-28 | GGATATTCCTTTCTACTCTTTGACATCATCTCTCACAGC AGAAAAGCCAATACTT | 441 |
| rPout-ERBB2-29 | GGATATTCCTTTCTACTCTTTGACATCATCTCCGATAAA CACCACAGGCTCTA | 442 |
| rPout-ERBB2-3 | GGATATTCCTTTCTACTCTTTGACATCATCTGTCAGGCA GATGCCCAGAAG | 443 |
| rPout-ERBB2-30 | GGATATTCCTTTCTACTCTTTGACATCATCTCTCCAAGT CATGCCACCTCA | 444 |
| rPout-ERBB2-31 | GGATATTCCTTTCTACTCTTTGACATCATCTAGGTGGAC AGGGGACATGA | 445 |
| rPout-ERBB2-32 | GGATATTCCTTTCTACTCTTTGACATCATCTCTGAAATA GGAACACTGCCACC | 446 |
| rPout-ERBB2-33 | GGATATTCCTTTCTACTCTTTGACATCATCTCAAAGCCT CCCCCTGGTTAG | 447 |
| rPout-ERBB2-34 | GGATATTCCTTTCTACTCTTTGACATCATCTTGTGGAGT CTGAAACTCAGCC | 448 |
| rPout-ERBB2-35 | GGATATTCCTTTCTACTCTTTGACATCATCTCAGGGAGG GGCATGGC | 449 |
| rPout-ERBB2-36 | GGATATTCCTTTCTACTCTTTGACATCATCTCTGAGACT CACGGCTCTGAC | 450 |
| rPout-ERBB2-37 | GGATATTCCTTTCTACTCTTTGACATCATCTCTAAATTC GGTCTCAAAAACAAAACGAA | 451 |
| rPout-ERBB2-38 | GGATATTCCTTTCTACTCTTTGACATCATCTCCACACTG ACAGGGGATATAGG | 452 |
| rPout-ERBB2-39 | GGATATTCCTTTCTACTCTTTGAcATcATcTcATACAAG TCCTTGTTCACGGATAG | 453 |
| rPout-ERBB2-4 | GGATATTCCTTTCTACTCTTTGACATCATCTGACCAGCA CGTTCCGAGC | 454 |
| rPout-ERBB2-40 | GGATATTCCTTTCTACTCTTTGACATCATCTAGGGACCG CAGGGGAC | 455 |
| rPout-ERBB2-41 | GGATATTCCTTTCTACTCTTTGACATCATCTCCCTAGCA CAGCCACAGTC | 456 |
| rPout-ERBB2-42 | GGATATTCCTTTCTACTCTTTGACATCATCTTTTTCTCA TTTAGTTGTCTTTAAATTGAAATGC | 457 |
| rPout-ERBB2-43 | GGATATTCCTTTCTACTCTTTGACATCATCTGGCAGCCC TTGTCATCCAG | 458 |
| rPout-ERBB2-44 | GGATATTCCTTTCTACTCTTTGACATCATCTCACCCTGA CTCTAACTTGACCC | 459 |
| rPout-ERBB2-45 | GGATATTCCTTTCTACTCTTTGACATCATCTCATGGGTA CAGGAATGTACACCT | 460 |
| rPout-ERBB2-46 | GGATATTCCTTTCTACTCTTTGACATCATCTTCTAAAAC CTGCCTTGGCTCC | 461 |
| rPout-ERBB2-47 | GGATATTCCTTTCTACTCTTTGACATcATcTCAGCAGTC TCCGCATCGT | 462 |
| rPout-ERBB2-48 | GGATATTCCTTTCTACTCTTTGACATCATCTCACTGTGC CCAGCTTAATTTTGT | 463 |
| rPout-ERBB2-49 | GGATATTCCTTTCTACTCTTTGACATCATCTCCCTGGGG TGTCAAGTACTC | 464 |
| rPout-ERBB2-5 | GGATATTCCTTTCTACTCTTTGACATCATCTCATAACTC CACACATCACTCTGGT | 465 |

TABLE 3-continued

Primer sequences in the 179-plex comprehensive panel

| Name | Primer sequence | SEQ ID NO: |
|---|---|---|
| rPout-ERBB2-50 | GGATATTCCTTTCTACTCTTTGACATCATCTTGTTCCTCTTCCAACGAGGC | 466 |
| rPout-ERBB2-6 | GGATATTCCTTTCTACTCTTTGACATCATCTCAGGCACTCTCGGTGGATC | 467 |
| rPout-ERBB2-7 | GGATATTCCTTTCTACTCTTTGACATCATCTCCTAAGGTCAAATCCTAGGGGGTAATA | 468 |
| rPout-ERBB2-8 | GGATATTCCTTTCTACTCTTTGACATCATCTCCGGGGCTCTGGTCATTG | 469 |
| rPout-ERBB2-9 | GGATATTCCTTTCTACTCTTTGACATCATCTGTTCAGCGGGTCTCCATTGT | 470 |
| rPout-Mut1 | GGATATTCCTTTCTACTCTTTGACATCATCTTGAAGACCTCACAGTAAAAATAGGTGATT | 471 |
| rPout-Mut2 | GGATATTCCTTTCTACTCTTTGACATCATCTTGTGGAAGATCCAATCCATTTTTGTTG | 472 |
| rPout-Mut4 | GGATATTCCTTTCTACTCTTTGACATCATCTGAGGGTCTGACGGGTAGAGT | 473 |
| rPout-Mut5 | GGATATTCCTTTCTACTCTTTGACATCATCTACAGCACATGACGGAGGTTG | 474 |
| rPout-Mut6 | GGATATTCCTTTCTACTCTTTGACATCATCTTTATAAGGCCTGCTGAAAATGACTGAA | 475 |
| rPout-mut10 | GGATATTCCTTTCTACTCTTTGACATCATCTGACCCCAGTTGCAAACCAGAC | 476 |
| rPout-mut11 | GGATATTCCTTTCTACTCTTTGACATCATCTTCTGATTCCTCACTGATTGCTCTTAG | 477 |
| rPout-mut12 | GGATATTCCTTTCTACTCTTTGACATCATCTCGGGGGCTCAGCATCCA | 478 |
| rPout-mut13 | GGATATTCCTTTCTACTCTTTGACATCATCTCAAACAGTAGCTTCCCTGGGT | 479 |
| rPout-mut14 | GGATATTCCTTTCTACTCTTTGACATCATCTCAGGACTCGGTGGATATGGTC | 480 |
| rPout-mut15 | GGATATTCCTTTCTACTCTTTGACATCATCTGGCGCATGTAGGCGGTG | 481 |
| rPout-mut16 | GGATATTCCTTTCTACTCTTTGACATCATCTGGAGATGTGGTCAATGGAAGAAAC | 482 |
| rPout-mut17 | GGATATTCCTTTCTACTCTTTGACATCATCTTCGTGTTGGCAACATACCATCT | 483 |
| rPout-mut18 | GGATATTCCTTTCTACTCTTTGACATCATCTCTTCTAACAGCTACCCTTCCATCAT | 484 |
| rPout-mut19 | GGATATTCCTTTCTACTCTTTGACATCATCTAGGAAAGTTCTGCTGTTTTTAGCAAA | 485 |
| rPout-mut20 | GGATATTCCTTTCTACTCTTTGACATCATCTCTCAGTATTTGCAGAATACATTCAAGGT | 486 |
| rPout-mut21 | GGATATTCCTTTCTACTCTTTGACATCATCTGAAGAGTAACAAGCCAAATGAACAGA | 487 |
| rPout-mut22 | GGATATTCCTTTCTACTCTTTGACATCATCTTTGATAGTTGTTCTAGCAGTGAAGAGA | 488 |
| rPout-mut23 | GGATATTCCTTTCTACTCTTTGACATCATCTACAATTCAAAAGCACCTAAAAAGAATAGG | 489 |
| rPout-mut24 | GGATATTCCTTTCTACTCTTTGACATCATCTACAGAAAAAAAGGTAGATCTGAATGCT | 490 |

TABLE 3-continued

Primer sequences in the 179-plex comprehensive panel

| Name | Primer sequence | SEQ ID NO: |
|---|---|---|
| rPout-mut25 | GGATATTCCTTTCTACTCTTTGACATCATCTAGGATCTG ATTCTTCTGAAGATACCG | 491 |
| rPout-mut26 | GGATATTCCTTTCTACTCTTTGACATCATCTTGGATTTA TCTGCTCTTCGCGT | 492 |
| rPout-mut27 | GGATATTCCTTTCTACTCTTTGACATCATCTGTATCTAC AACTGTTTCATATACTTCATCTTCT | 493 |
| rPout-mut28 | GGATATTCCTTTCTACTCTTTGACATCATCTCAGGCCAA AGACGGTACAACT | 494 |
| rPout-mut29 | GGATATTCCTTTCTACTCTTTGACATCATCTCTCTTCTT TTTCCAATTCTTGAATTTGACA | 495 |
| rPout-mut30 | GGATATTCCTTTCTACTCTTTGACATCATCTGCAGTTTC AGGACATCCATTTTATCAA | 496 |
| rPout-mut31 | GGATATTCCTTTCTACTCTTTGACATCATCTCCAAGTTA ATATTCCTAACACACTGTTCA | 497 |
| rPout-mut32 | GGATATTCCTTTCTACTCTTTGACATCATCTAATAAGGC TTCTAGTCTCTTTTGTTGG | 498 |
| rPout-mut33 | GGATATTCCTTTCTACTCTTTGACATCATCTACAAGCAC TTATCAAAACTGAAAAATTACAAT | 499 |
| rPout-mut34 | GGATATTCCTTTCTACTCTTTGACATCATCTGGCTTAAT AATGTCCTCATTAAGGTCTATC | 500 |
| rPout-mut35 | GGATATTCCTTTCTACTCTTTGACATCATCTCAATGCAA GTTCTTCGTCAGCTA | 501 |
| rPout-mut36 | GGATATTCCTTTCTACTCTTTGACATCATCTTTTAAACT ATTTCTAACAACGCCTTCTCT | 502 |
| rPout-mut37 | GGATATTCCTTTCTACTCTTTGACATCATCTTCAACATC CCACCTCCCATCTA | 503 |
| rPout-mut38 | GGATATTCCTTTCTACTCTTTGACATCATCTGAATCATA TTTGTGTCTGATGGGCAAT | 504 |
| rPout-mut39 | GGATATTCCTTTCTACTCTTTGACATCATCTAAACCATG TGAAAATCACAGATTTTGG | 505 |
| rPout-mut3new | GGATATTCCTTTCTACTCTTTGACATCATCTCAGAGAAT CTCCATTTTAGCACTTACC | 506 |
| rPout-mut40 | GGATATTCCTTTCTACTCTTTGACATCATCTTGAATATC ATTAAGGAACTTGATATTTTTCAGG | 507 |
| rPout-mut41 | GGATATTCCTTTCTACTCTTTGACATCATCTAAATTTGA GTTGAAATCATGGTATTGCAT | 508 |
| rPout-mut42 | GGATATTCCTTTCTACTCTTTGACATCATCTCACAGCAC CCAATCAAGCTC | 509 |
| rPout-mut43 | GGATATTCCTTTCTACTCTTTGACATCATCTGACAACAC TCTTCAGCACAATCAA | 510 |
| rPout-mut44 | GGATATTCCTTTCTACTCTTTGACATCATCTAGGGCATC ACCTCTCTACAGTT | 511 |
| rPout-mut45 | GGATATTCCTTTCTACTCTTTGACATCATCTGTTTGCTG AATGTTAACATTAATGCTTATTT | 512 |
| rPout-mut46 | GGATATTCCTTTCTACTCTTTGACATCATCTACGGACCT TACGTCAGTGACT | 513 |
| rPout-mut47 | GGATATTCCTTTCTACTCTTTGACATCATCTGGCTACGT GTTAGTGGCTCTTA | 514 |
| rPout-mut48 | GGATATTCCTTTCTACTCTTTGACATCATCTACGGAGAA TAAACTGAGCTCTCTC | 515 |

TABLE 3-continued

Primer sequences in the 179-plex comprehensive panel

| Name | Primer sequence | SEQ ID NO: |
|---|---|---|
| rPout-mut49 | GGATATTCCTTTCTACTCTTTGACATCATCTCCAAAAAATGAAGCCGGCGA | 516 |
| rPout-mut50 | GGATATTCCTTTCTACTCTTTGACATCATCTTGCCTACTGGTTCAATTACTTTTAAAAAG | 517 |
| rPout-mut51 | GGATATTCCTTTCTACTCTTTGACATCATCTCATCAGCATTTGACTTTACCTTATCAATG | 518 |
| rPout-mut52 | GGATATTCCTTTCTACTCTTTGACATCATCTCTAGAGTGTCTGTGTAATCAAACAAGTTT | 519 |
| rPout-mut53 | GGATATTCCTTTCTACTCTTTGACATCATCTTGATCCAGTAACACCAATAGGGTTC | 520 |
| rPout-mut54 | GGATATTCCTTTCTACTCTTTGACATCATCTAGTGAAAAGAGTCTCAAACACAAACTAG | 521 |
| rPout-mut55 | GGATATTCCTTTCTACTCTTTGACATCATCTTTTTTTCCAGTTTATTGTATTTGCATAGCA | 522 |
| rPout-mut56 | GGATATTCCTTTCTACTCTTTGACATCATCTCCTTATACACCGTGCCGAACG | 523 |
| rPout-mut57 | GGATATTCCTTTCTACTCTTTGACATCATCTCACAGCAAAGCAGAAACTCACA | 524 |
| rPout-mut58 | GGATATTCCTTTCTACTCTTTGACATCATCTCCCTCCCTCCAGGAAGCCTA | 525 |
| rPout-mut59 | GGATATTCCTTTCTACTCTTTGACATCATCTGGAGCCAATATTGTCTTTGTGTTCC | 526 |
| rPout-mut60 | GGATATTCCTTTCTACTCTTTGACATCATCTCTCCTTCTGCATGGTATTCTTTCTC | 527 |
| rPout-mut61 | GGATATTCCTTTCTACTCTTTGACATCATCTTGATGGGCAGATTACAGTGGG | 528 |
| rPout-mut62 | GGATATTCCTTTCTACTCTTTGACATCATCTTGGATACAGGTCAAGTCTAAGTCG | 529 |
| rPout-mut63 | GGATATTCCTTTCTACTCTTTGACATCATCTCAATATTGTTCCTGTATACGCCTTCA | 530 |
| rPout-mut64 | GGATATTCCTTTCTACTCTTTGACATCATCTTTGCAAGCATACAAATAAGAAAACATACTT | 531 |
| rPout-mut65 | GGATATTCCTTTCTACTCTTTGACATCATCTTCATACCTACCTCTGCAATTAAATTTGG | 532 |
| rPout-mut66 | GGATATTCCTTTCTACTCTTTGACATCATCTCCCCGATGTAATAAATATGCACATATCA | 533 |
| rPout-mut67 | GGATATTCCTTTCTACTCTTTGACATCATCTTGTTTTCCAATAAATTCTCAGATCCAGG | 534 |
| rPout-mut68 | GGATATTCCTTTCTACTCTTTGACATCATCTTGGATATTTCTCCCAATGAAAGTAAAGTAC | 535 |
| rPout-mut69 | GGATATTCCTTTCTACTCTTTGACATCATCTTGCTATCGATTTCTTGATCACATAGACT | 536 |
| rPout-mut7 | GGATATTCCTTTCTACTCTTTGACATCATCTCGTGGGCGTGAGCGC | 537 |
| rPout-mut70 | GGATATTCCTTTCTACTCTTTGACATCATCTCTGACCTTAAAATTTGGAGAAAAGTATCG | 538 |
| rPout-mut71 | GGATATTCCTTTCTACTCTTTGACATCATCTCATCTGGTGTTACAGAAGTTGAACTG | 539 |
| rPout-mut72 | GGATATTCCTTTCTACTCTTTGACATCATCTCGAAGATGGCAAACTTCCCATC | 540 |

TABLE 3-continued

Primer sequences in the 179-plex comprehensive panel

| Name | Primer sequence | SEQ ID NO: |
|---|---|---|
| rPout-mut73 | GGATATTCCTTTCTACTCTTTGACATCATCTCTCAGACA CTTACGGGGACAG | 541 |
| rPout-mut74 | GGATATTCCTTTCTACTCTTTGACATCATCTGACAGGCC CTGACACAGG | 542 |
| rPout-mut75 | GGATATTCCTTTCTACTCTTTGACATCATCTATCTCTAA CCCATTGAGGCCG | 543 |
| rPout-mut76 | GGATATTCCTTTCTACTCTTTGACATCATCTACACTTGA CCATCACCATGTAGAC | 544 |
| rPout-mut77 | GGATATTCCTTTCTACTCTTTGACATCATCTTACAAGCT GTCTCTCTCCCAGT | 545 |
| rPout-mut78 | GGATATTCCTTTCTACTCTTTGACATCATCTCCAGCCCA TGGCAAACAC | 546 |
| rPout-mut79 | GGATATTCCTTTCTACTCTTTGACATCATCTCGCTCACC ATGTGTGACTTGAT | 547 |
| rPout-mut8 | GGATATTCCTTTCTACTCTTTGACATCATCTTCCTATCC TGAGTAGTGGTAATCTACT | 548 |
| rPout-mut9 | GGATATTCCTTTCTACTCTTTGACATCATCTTCTGACTG TACCACCATCCACT | 549 |
| rPout-Ref-1 | GGATATTCCTTTCTACTCTTTGACATCATCTAGTAACAG TAGGTGTTTCAATATGACTTTT | 550 |
| rPout-Ref-10 | GGATATTCCTTTCTACTCTTTGACATCATCTCCCTCCAG GAGCCCACC | 551 |
| rPout-Ref-11 | GGATATTCCTTTCTACTCTTTGACATCATCTACTGCTAC TACATACCAGGTTCTG | 552 |
| rPout-Ref-12 | GGATATTCCTTTCTACTCTTTGACATCATCTCTGATCAA GGCACCGCTCTAA | 553 |
| rPout-Ref-13 | GGATATTCCTTTCTACTCTTTGACATCATCTCTCCATCC CGGTGTGCAT | 554 |
| rPout-Ref-14 | GGATATTCCTTTCTACTCTTTGACATCATCTTCAAGGGC TATGGGGGCTT | 555 |
| rPout-Ref-15 | GGATATTCCTTTCTACTCTTTGACATCATCTAGATGTGC CCTGACATCAGAAATA | 556 |
| rPout-Ref-16 | GGATATTCCTTTCTACTCTTTGACATCATCTTCACTTAA CCTTCAGTGTTGATCTGA | 557 |
| rPout-Ref-17 | GGATATTCCTTTCTACTCTTTGACATCATCTAGGAGTGG GACCATGTTTGG | 558 |
| rPout-Ref-18 | GGATATTCCTTTCTACTCTTTGACATCATCTCCATCGCT CCCATCATTGCT | 559 |
| rPout-Ref-19 | GGATATTCCTTTCTACTCTTTGACATCATCTCTTTCAAA CACGTGTGATCAATAGTAC | 560 |
| rPout-Ref-2 | GGATATTCCTTTCTACTCTTTGACATCATCTCATTCTCA TATCAGAACTTAAATACATAGCAG | 561 |
| rPout-Ref-20 | GGATATTCCTTTCTACTCTTTGACATCATCTACAAGTCC ATCTTATAGGGGAAGGA | 562 |
| rPout-Ref-21 | GGATATTCCTTTCTACTCTTTGACATCATCTAAATGCAT GAGCATGCGCAA | 563 |
| rPout-Ref-22 | GGATATTCCTTTCTACTCTTTGACATCATCTCCACGATA AAATTCTCTTATCTTGAAGGATT | 564 |
| rPout-Ref-23 | GGATATTCCTTTCTACTCTTTGACATCATCTGTTCAAAG TGTTTCTGATATTGAAAAATTTTAAGT | 565 |

TABLE 3-continued

Primer sequences in the 179-plex comprehensive panel

| Name | Primer sequence | SEQ ID NO: |
|---|---|---|
| rPout-Ref-24 | GGATATTCCTTTCTACTCTTTGACATCATCTCCTTTTTC ATCCTTCGCACATGTATA | 566 |
| rPout-Ref-25 | GGATATTCCTTTCTACTCTTTGACATCATCTCCCTGGAG CAGATGACTCACA | 567 |
| rPout-Ref-26 | GGATATTCCTTTCTACTCTTTGACATCATCTAGGCAGGG GGCTTGGT | 568 |
| rPout-Ref-27 | GGATATTCCTTTCTACTCTTTGACATCATCTCACACCTT TTTTAACAACCGGATCT | 569 |
| rPout-Ref-28 | GGATATTCCTTTCTACTCTTTGACATCATCTAGGTGAGG CCCTGTAATCTGTA | 570 |
| rPout-Ref-29 | GGATATTCCTTTCTACTCTTTGACATCATCTACCTTAAT ATCAGACTTCCCAGCC | 571 |
| rPout-Ref-3 | GGATATTCCTTTCTACTCTTTGACATCATCTTTTTGGGA GCTCTGAGACAGG | 572 |
| rPout-Ref-30 | GGATATTCCTTTCTACTCTTTGACATCATCTCTGATGGC AAAGCAGAAGACAATA | 573 |
| rPout-Ref-31 | GGATATTCCTTTCTACTCTTTGACATCATCTAGCCCTTT CAGGGAGTCCT | 574 |
| rPout-Ref-32 | GGATATTCCTTTCTACTCTTTGACATCATCTTCTCTTAA TCTCAGTTTTCGTTACTGTAAAAT | 575 |
| rPout-Ref-33 | GGATATTCCTTTCTACTCTTTGACATCATCTCATAGCAC CACTCGGTGAACTT | 576 |
| rPout-Ref-34 | GGATATTCCTTTCTACTCTTTGACATCATCTAGGAGTGA GAACCCACGTACA | 577 |
| rPout-Ref-35 | GGATATTCCTTTCTACTCTTTGACATCATCTCAACAGTG TGAATGTACTTAATGACACT | 578 |
| rPout-Ref-36 | GGATATTCCTTTCTACTCTTTGACATCATCTCCTGTCCT GTGAGGCAGG | 579 |
| rPout-Ref-37 | GGATATTCCTTTCTACTCTTTGACATCATCTTGCCCTGC TGGTGTTCTTTTATA | 580 |
| rPout-Ref-38 | GGATATTCCTTTCTACTCTTTGACATCATCTTCGCTGCT GCTGTTGCT | 581 |
| rPout-Ref-39 | GGATATTCCTTTCTACTCTTTGACATCATCTGGGTCCTC AGGTCCTTGTG | 582 |
| rPout-Ref-4 | GGATATTCCTTTCTACTCTTTGACATCATCTGCGTTGGG AACTTCAACTGG | 583 |
| rPout-Ref-40 | GGATATTCCTTTCTACTCTTTGACATCATCTTTGTAGCC CAGCATGGCAA | 584 |
| rPout-Ref-41 | GGATATTCCTTTCTACTCTTTGACATCATCTTTTGCTTT TGAGGGACAGAAAATCA | 585 |
| rPout-Ref-42 | GGATATTCCTTTCTACTCTTTGACATCATCTACTTGGCT AATGAGTTGATCTCTCT | 586 |
| rPout-Ref-43 | GGATATTCCTTTCTACTCTTTGACATCATCTAGTTATTT TCAAAAGAAAACAAAGGACATAGATT | 587 |
| rPout-Ref-44 | GGATATTCCTTTCTACTCTTTGACATCATCTGCAAAGAG TGCTCAAACCTTGG | 588 |
| rPout-Ref-45 | GGATATTCCTTTCTACTCTTTGACATCATCTGTTACTAA TTTTTTTGGCTATCATGCCA | 589 |
| rPout-Ref-46 | GGATATTCCTTTCTACTCTTTGACATCATCTGTAGCAGA GAACCCACTTGGG | 590 |

TABLE 3-continued

| Primer sequences in the 179-plex comprehensive panel | | |
|---|---|---|
| Name | Primer sequence | SEQ ID NO: |
| rPout-Ref-47 | GGATATTCCTTTCTACTCTTTGACATCATCTAGCTCAAA CCATATTCTTAATTTTTAAAATTCAC | 591 |
| rPout-Ref-48 | GGATATTCCTTTCTACTCTTTGACATCATCTCTCCTCTG TCGTAAGTCAAGTCTTT | 592 |
| rPout-Ref-49 | GGATATTCCTTTCTACTCTTTGACATCATCTCAGTCTGG TAAAGTGCTATCGAATC | 593 |
| rPout-Ref-5 | GGATATTCCTTTCTACTCTTTGACATCATCTCTGAATAG TCCGTTTCGGATACTCA | 594 |
| rPout-Ref-50 | GGATATTCCTTTCTACTCTTTGACATCATCTAAAAACAC AAATTACCTAAACTGACTCAAG | 595 |
| rPout-Ref-6 | GGATATTCCTTTCTACTCTTTGACATCATCTAGCGCCTC CCGGCT | 596 |
| rPout-Ref-7 | GGATATTCCTTTCTACTCTTTGACATCATCTTGCCAGAG GTAGTGGAGGTC | 597 |
| rPout-Ref-8 | GGATATTCCTTTCTACTCTTTGACATCATCTAGTGACTT GCGTTCATCTTGTTATTTA | 598 |
| rPout-Ref-9 | GGATATTCCTTTCTACTCTTTGACATCATCTGGAGCCTG AAAAGGTAGGTTGG | 599 |

III. UMI Design

In the NGS library preparation process, PCR amplification steps can significantly increase the quantitation variation, making it difficult to differentiate small changes in original molecule number. UMI technology may be used to reduce PCR bias and achieve absolute quantitation of original DNA molecules. The concept of UMI is to give every original DNA molecule a different DNA sequence as a "barcode," so that the origin of each NGS read can be tracked based on the barcode sequence. Given enough NGS reads, the number of unique UMIs found in the NGS output can reflect the number of original DNA molecules. Previously, UMI technology was mostly used for error correction in NGS-based detection of low-frequency mutations; it has also been applied to quantitation. Labeling each original molecule uniquely is achieved by using a large number of different UMI sequences; for example, using $10^9$ different UMI sequences for 100,000 original molecules will generate <0.006% molecules carrying repeated UMIs.

Figure 2:
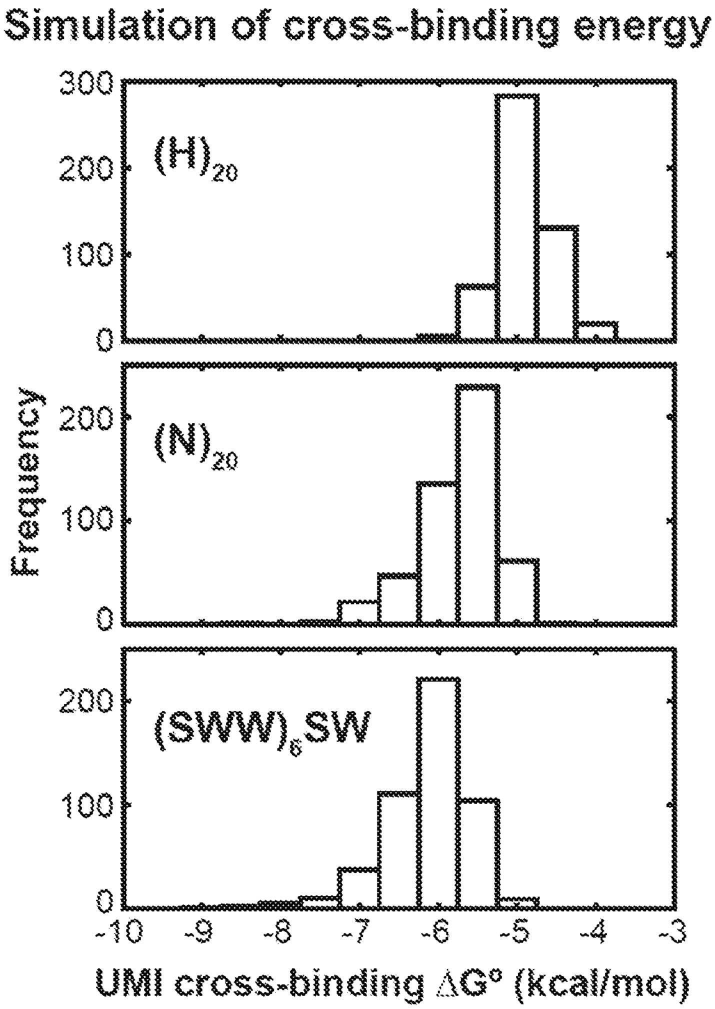
FIG. 2. Simulation of UMI cross-binding energy. Using $(H)_{20}$ instead of $(N)_{20}$ or $(SWW)_6SW$ as UMI sequences reduces the mean cross-binding energy, indicating fewer primer-dimer interactions. Here 500 simulations were performed for each UMI pattern; in each simulation, 2 sequences that are consistent with the pattern were randomly generated, and the cross-binding $\Delta G°$ between these sequences were calculated assuming 60° C. and 0.18 M $K^+$.

DNA sequences containing degenerate bases, such as poly(N) (i.e., a mix of A, T, C, or G at each position), are often used as UMI sequences. In QASeq, poly(H) (A, T, or C) is used as the UMI because it has weaker cross-binding energy compared to poly(N) or a mix of S (C or G) and W (A or T) bases, as indicated by simulation (FIG. 2). $(H)_{20}$ contains $3.5\times10^9$ different sequences, which are enough for 100,000 molecules as input; $(H)_{15}$ contains $1.4\times10^7$ different sequences, which are enough for 6,000 molecules as input.

IV. Spacer to Reduce PCR Bias

PCR efficiency varies for amplicons with different sequences. Because UMIs consist of many different sequences, a spacer between the primer and the variable UMI region may be used to achieve more uniform PCR efficiency.

Figure 3:
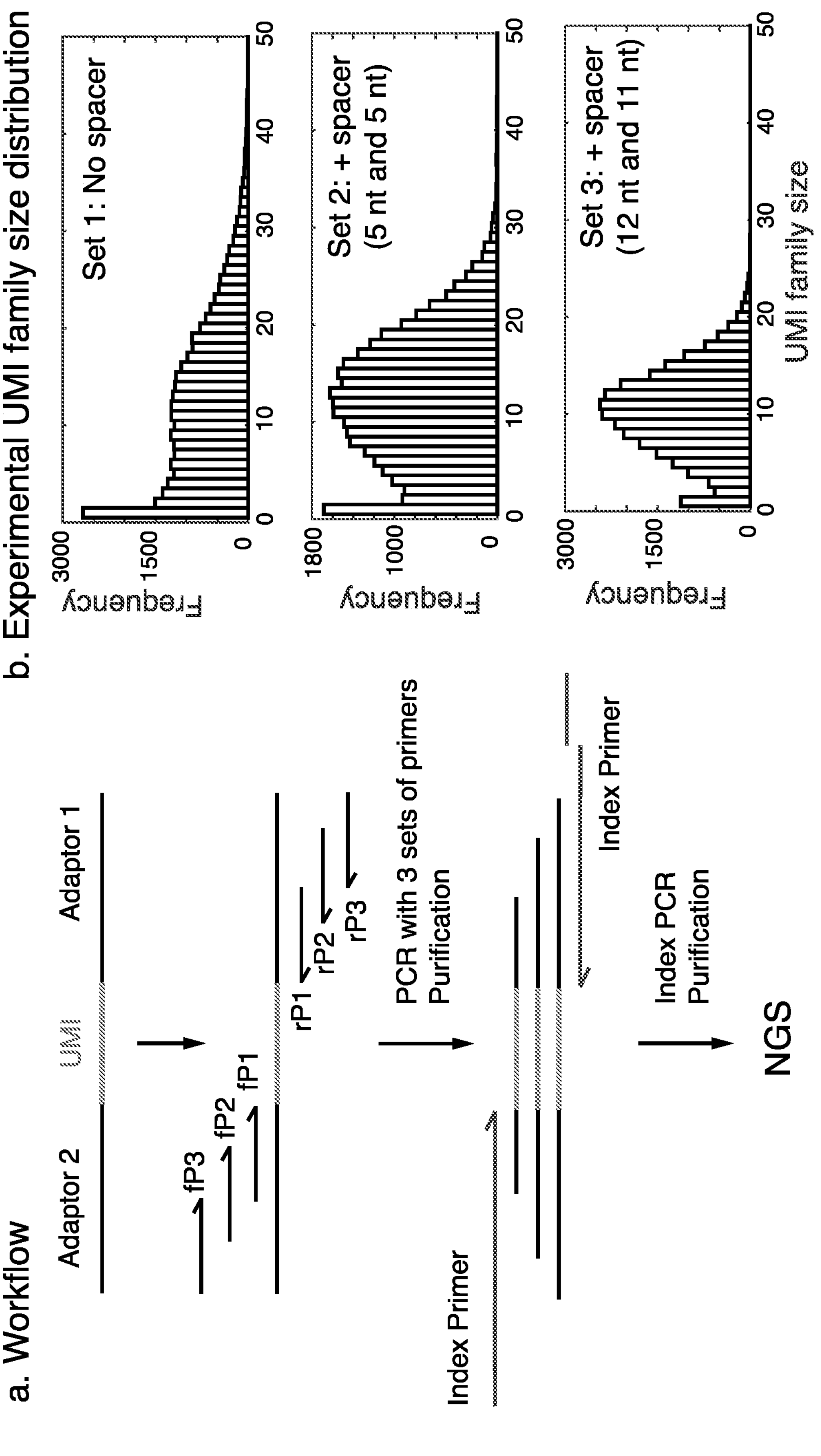
FIGS. 3A-B. Spacer between primer and UMI reduces PCR bias.

NGS was carried out to evaluate the influence of spacer on PCR bias (FIG. 3A). The template molecules have two adaptors on the 5' and 3' end for amplification, and a UMI region consists of $(D)_{15}$ in the middle. Three sets of primers, without any spacer (set 1), with a 5 nt spacer between the forward primer and the UMI and a 5 nt spacer between the reverse primer and the UMI (set 2), or with a 12 nt spacer between the forward primer and the UMI and a 11 nt spacer between the reverse primer and the UMI (set 3) were used to amplify the template separately. Indices were added via PCR before NGS analysis. $(D)_{15}$ contains $1.4\times10^7$ different sequences. Because the input template molecule number is far below the possible sequence number, each unique UMI sequence only has 1 copy before amplification. All NGS reads carrying the same UMI are presumably derived from the same molecule. As such, UMI family size (i.e., the number of reads carrying the same UMI) is an indication of the PCR efficiency.

UMI family size distribution was compared to evaluate the significance of spacers on PCR bias (FIG. 3B). More uniform distribution was observed when the spacer between primers and UMI was longer. In primer set 3, wherein the spacer length was longer than 10 nt at both ends, a significantly improved distribution was achieved.

V. QASeq Workflow

A schematic of the QASeq NGS library preparation workflow is shown in FIG. 1. First, a DNA sample is mixed with all the SfP, SrPA, DNA polymerase, dNTPs, and PCR buffer. Two cycles of long-extension (about 30 min) PCR are performed for addition of UMI on all target loci. Afterwards, each strand in one DNA molecule will carry a different UMI. Next, in order to amplify the molecules while preventing addition of multiple UMIs onto the same original molecule, the annealing temperature is raised by about 8° C. and amplification is performed for at least two cycles (e.g., for about seven cycles) using UfP and UrP and with a short-extension (about 30 s). Addition of UfP and UrP into the reaction is an open-tube step on the thermocycler. After purification using SPRI magnetic beads or columns, SrPB primers, DNA polymerase, dNTPs, and PCR buffer are mixed with the PCR product for adapter replacement; after at least one cycle (e.g., two cycles) of long extension (about 30 min), the NGS adapters are only added onto the correct PCR products, not the primer dimers or non-specific products. After another purification using SPRI magnetic beads or columns, standard NGS index PCR is performed; libraries are normalized and loaded onto an Illumina sequencer.

All types of DNA polymerases and PCR supermixes can be used. The standard annealing, extension, and denaturation temperature for the specific polymerase used should be followed (except for the universal PCR step, in which the annealing temperature is raised).

VI. Alternative QASeq Workflows

Figure 9:
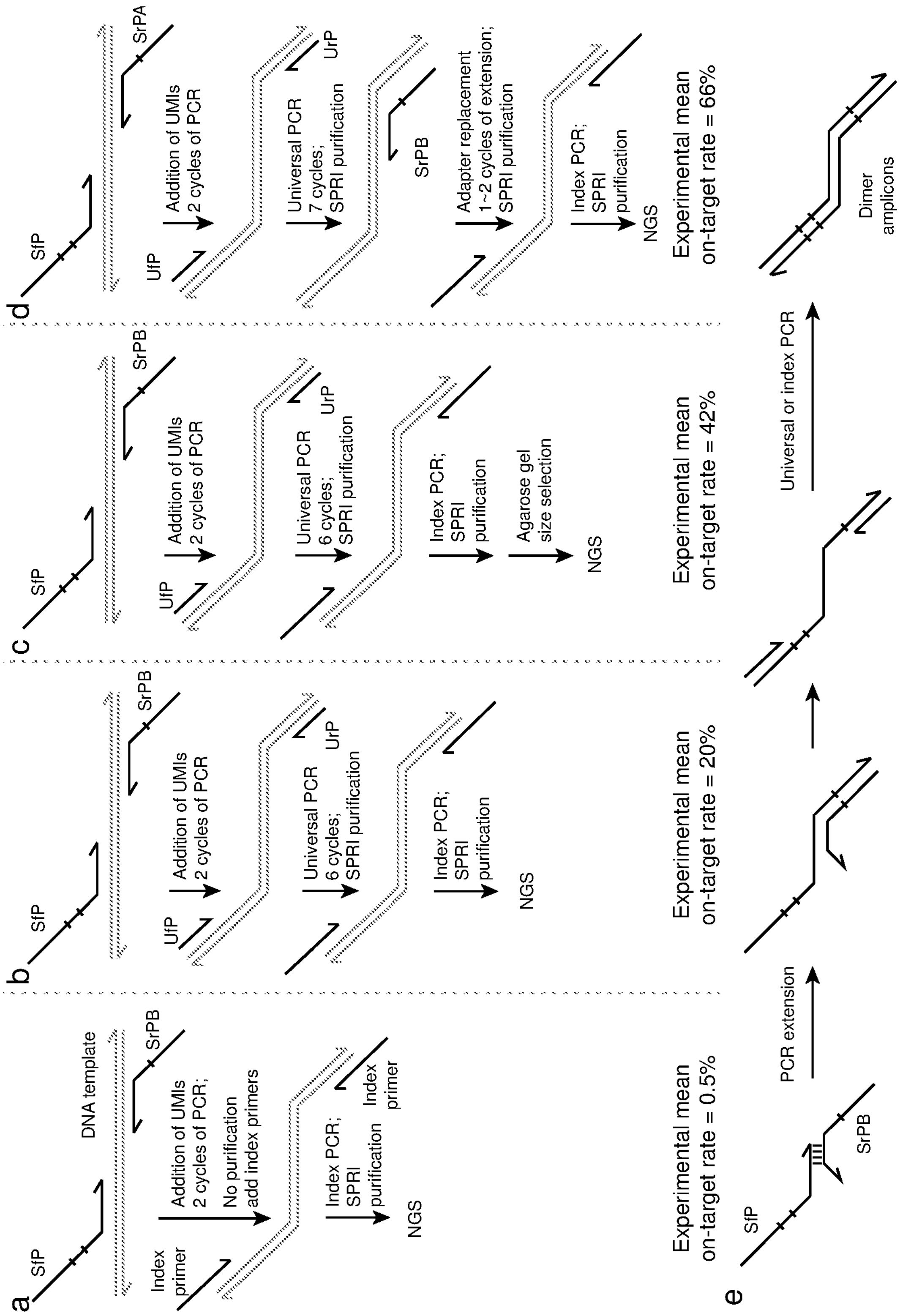

The workflow may be performed using SfP and SrPB to add UMIs using two cycles of PCR, and then directly adding index primers for index PCR. To test this, twenty sets of SfP and SrPB were used in the same reaction. The experimental on-target rate of this method is very low (0.5%), and thus this method may not be useful in an NGS assay for diagnostics (FIG. 9A). The off-target NGS reads were mostly primer dimers. In a second alternative workflow, universal PCR is performed using UfP and Urp for six cycles of universal PCR, which is following by a purification step. These additional steps improved the on-target rate to 12-28% (mean on-target rate=20%) for different libraries (FIG. 9B). A third alternative workflow based on the second alternative workflow was tested. For this, a size selection step using agarose gel was added after index PCR to further reduce primer dimers. The experimental mean on-target rate was improved to 42%, but still lower than 50% (FIG. 9C). Primer dimer reduction was achieved using the primary experimental workflow, which includes both adapter replacement and purification after universal PCR, and results in a high mean on-target rate of 66% (FIG. 9D). One source of primer dimers in the above-mentioned workflows is shown in FIG. 9E. If the 3' part of SfP binds to SfPB, or the 3' part of SfPB binds to SfP, a dimer strand with universal regions at both 5' and 3' ends can be generated and thus amplified in the universal or index PCR step.

The primary workflow includes a final index PCR step to add index sequences and the sequencer's P5/P7 sequences to the ends of the amplicon; however, there are alternative workflows that add the abovementioned sequences during UMI addition, universal PCR, or adapter replacement steps, and thus do not require the index PCR step. FIGS. 10A-C shows three examples. First, the index and P5 sequences are added onto the 5' of UfP; the other index and P7 sequences are added onto the 5' of SrPB. The amplicons obtained from adapter replacement contain P5, P7, and dual index, and thus are ready for sequencing (FIG. 10A). Second, the index and P7 sequences are added onto the 5' of SrPB, and this modified SrPB is mixed with the normal P5 index primer in the adapter replacement step (FIG. 10B). Third, the index and P5 sequences are added onto the 5' of SfP; a primer bearing the P5 sequence is used as UfP in the universal PCR step. The other index and P7 sequences are added onto the 5' of SrPB (FIG. 10C).

An alternative QASeq primer design and workflow is shown in FIG. 11. Each primer set comprises three different oligos: a Specific Forward Primer (SfP), a Specific Reverse Primer A (SrPA), and a Specific Reverse Primer B (SrPB). SfP comprises, from 5' to 3', regions 1, 2, 3, and 4. Region 4 is the template-binding region; region 3 is the UMI; region 1 is the full or partial NGS adapter; region 2 is an optional spacer region (0~15 nt) added for uniform amplification of UMIs. SrPA comprises region 5, which is the template-binding region. SrPB comprises, from 5' to 3', regions 6, 7, and 8. Region 8 is the template-binding region, the 3'-end of which is closer to region 4 than region 5 by at least 1 base; region 6 is the full or partial NGS adapter; region 7 is an optional spacer region (0~15 nt) added for uniform amplification of different loci. Each QASeq panel only needs one Universal Forward Primer (UfP), which comprises region 1; there can be additional bases at 5'-end of region 1 in UfP. The melting temperature (Tm) of template-binding regions 4, 5, and 8 are about the same as the PCR annealing temperature, and the Tm of UfP is not lower than regions 4, 5, and 8 in the experimental PCR conditions. Compared to the original design, SrPA only needs the template-binding region, and Universal Reverse Primer (UrP) is not necessary. In the experimental workflow, more cycles of PCR (e.g., at least 10 cycles) are needed in the universal PCR step under this alternative primer design.

VI. Data Analysis Workflow

Figure 4:
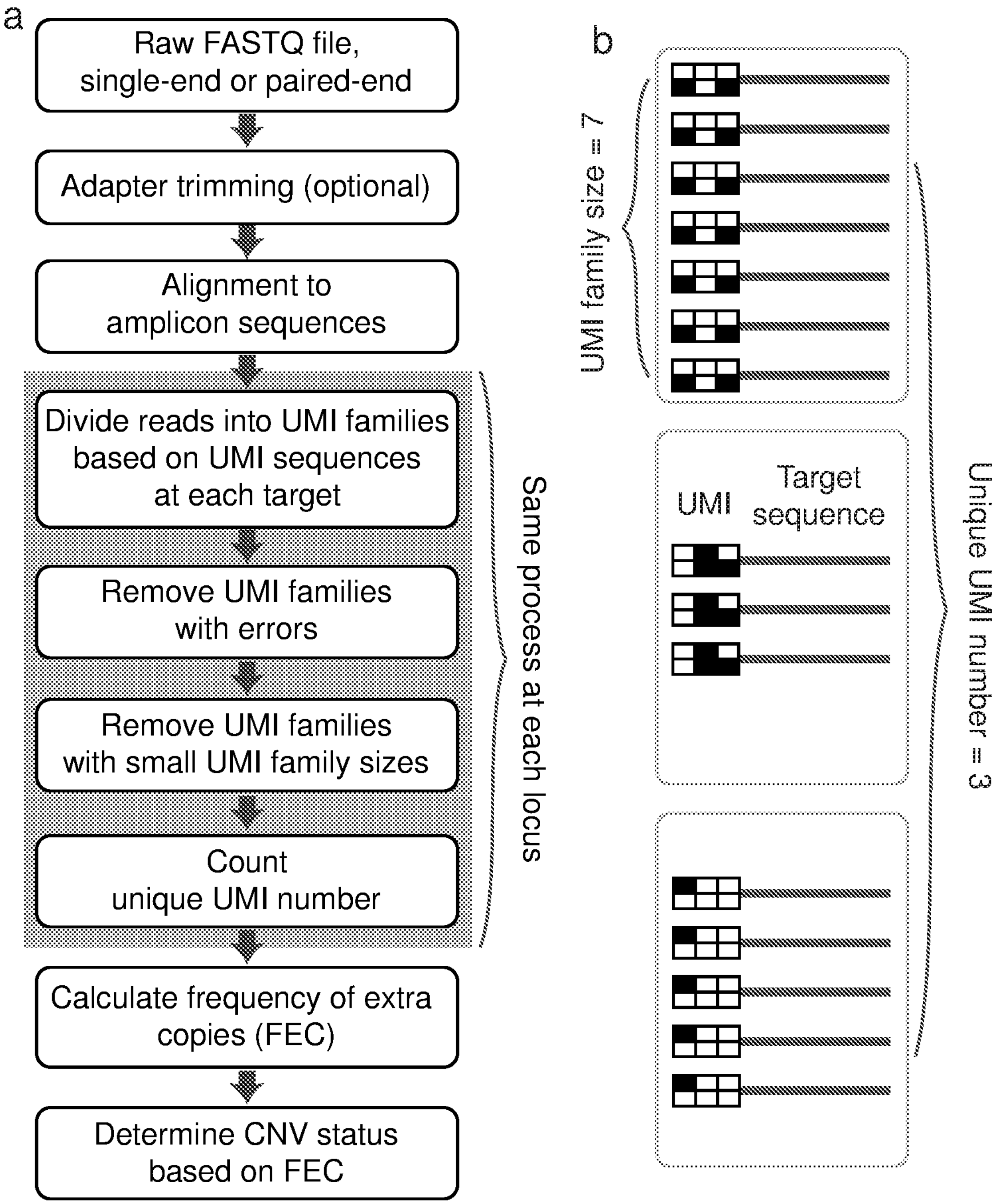
FIGS. 4A-B. Data analysis for UMI-based absolute quantitation for CNV.

A schematic of the data analysis workflow for CNV detection is shown in FIG. 4A. First, raw NGS reads are aligned to the amplicon regions; an optional adapter trimming can be performed before alignment. Unaligned reads are discarded, and the aligned reads are grouped by the loci they aligned to.

Then, all the reads aligned to the same locus are further divided by the UMI sequences, i.e., reads carrying the same UMI are grouped as one UMI family. UMI family size is the number of reads carrying the same UMI, and unique UMI number is the total count of different UMI sequences at one locus (FIG. 4B). Next, all unique UMI families that are likely results of PCR or NGS errors are removed. For example, a UMI sequence that is not consistent with designed UMI pattern (e.g., G bases found in a poly(H) UMI sequence) is an error and should be removed. Additionally, if two UMI sequences only differ by 1-2 bases, the one with a smaller UMI family size is likely mutated from the other, and thus can be optionally removed. After removal of UMI errors, the UMI families with family sizes $<F_{min}$ are also removed. $F_{min}$ is determined based on the distribution of UMI family size, and $F_{min}=4$ may be used most cases. The unique UMI number (N) after UMI removal is used for the next step.

FEC of a target gene may be calculated as:

$$FEC = k\frac{\sum_{i=1}^{u} N_{Tar,i}}{\sum_{j=1}^{w}\sum_{i=1}^{v} N_{Ref,i,j}} - 1, \text{ where } \sum_{i=1}^{u} N_{Tar,i}$$

is the sum of unique UMI number for all or part of the target gene loci, u is the number of loci to consider, u is no more than the total number of loci in the target gene;

$$\sum_{j=1}^{w}\sum_{i=1}^{v} N_{Ref,i,j}$$

is the sum of unique UMI number for all or part of Reference loci, v is the number of loci to consider for one reference, v is no more than the total number of loci in the reference; w is the number of reference to consider, w is no more than the total number of reference; and k is determined by experimental calibration. Before testing the QASeq panel on a clinical sample, calibration experiments were performed on DNA samples with well-characterized CNV status of the target gene. gDNA extracted from normal and cancer cell lines with CNV status characterized by ddPCR can be used for calibration. The FEC of normal calibration samples should be 0. The LoD of the assay is also determined by the calibration experiments; LoD is the smallest frequency of extra copies detectable by the assay. When testing a clinical sample, the FEC for a gene of interest will be used to infer the CNV status; if FEC>LoD, the sample is inferred to contain amplification of the target gene; if FEC≤LoD, the sample is inferred to contain deletion of the target gene.

VIII. Allele Ratio Quantitation

QASeq can be applied to quantifying the allele ratio of different genetic identities for 1~10,000 genomic loci using multiplexed PCR. The multiplexed PCR panel design for targeted genomic loci, and the experimental workflow for labeling each strand of targeted genomic loci with an oligonucleotide barcode sequence by PCR, followed by amplification of the genomic regions for high-throughput sequencing are similar to CNV detection.

A schematic of data analysis workflow for allele ratio quantitation is shown in FIG. 12A. First, raw NGS reads are aligned to the amplicon regions; an optional adapter trimming can be performed before alignment. Unaligned reads are discarded, and the aligned reads are grouped by the loci they aligned to. At each locus, the NGS reads are divided by the UMI sequence; all NGS reads carrying the same UMI sequence are grouped as one UMI family. The unique UMI families with errors in UMI, which are likely results of PCR or NGS errors are removed, as described in Data Analysis Workflow section.

The genetic identity (wild type or mutation) for each remaining UMI family is called based on majority vote; the genetic identity needs to be supported by at least 70% of the members (reads) in the same UMI family. As an example in FIG. 12B, for a UMI family with UMI family size=7, all the 7 reads share the same UMI sequence (displayed as a 2D barcode). The genetic identity at the locus of interest is 'A' for 6 reads and 'G' for 1 read. Because more than 70% of the reads in the UMI family support 'A', the genetic identity for this UMI family is called as 'A'. The 1 read corresponds to 'G' is a result of PCR or NGS error. UMI families without more than 70% reads supporting one consensus genetic identity are discarded.

Next, the unique UMI number N (the total count of different UMI sequences at one locus) is counted for each different genetic identity at the targeted locus; N indicates the number of original strands. Allele ratio of a target locus is calculated as $$R_{allele} = N_1/N_2,$$

where $N_1$ is unique UMI number for the first genetic identity, and $N_2$ is unique UMI number for the second genetic identity.

IX. Definitions

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30-100 "cycles" of denaturation and replication.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively).

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

"Incorporating," as used herein, means becoming part of a nucleic acid polymer.

The term "in the absence of exogenous manipulation" as used herein refers to there being modification of a nucleic acid molecule without changing the solution in which the nucleic acid molecule is being modified. In specific embodiments, it occurs in the absence of the hand of man or in the absence of a machine that changes solution conditions, which may also be referred to as buffer conditions. However, changes in temperature may occur during the modification.

A "nucleoside" is a base-sugar combination, i.e., a nucleotide lacking a phosphate. It is recognized in the art that there is a certain inter-changeability in usage of the terms nucleoside and nucleotide. For example, the nucleotide deoxyuridine triphosphate, dUTP, is a deoxyribonucleoside triphosphate. After incorporation into DNA, it serves as a DNA monomer, formally being deoxyuridylate, i.e., dUMP or deoxyuridine monophosphate. One may say that one incorporates dUTP into DNA even though there is no dUTP moiety in the resultant DNA. Similarly, one may say that one incorporates deoxyuridine into DNA even though that is only a part of the substrate molecule.

"Nucleotide," as used herein, is a term of art that refers to a base-sugar-phosphate combination. Nucleotides are the monomeric units of nucleic acid polymers, i.e., of DNA and RNA. The term includes ribonucleotide triphosphates, such as rATP, rCTP, rGTP, or rUTP, and deoxyribonucleotide triphosphates, such as dATP, dCTP, dUTP, dGTP, or dTTP.

The term "nucleic acid" or "polynucleotide" will generally refer to at least one molecule or strand of DNA, RNA, DNA-RNA chimera or a derivative or analog thereof, comprising at least one nucleobase, such as, for example, a naturally occurring purine or pyrimidine base found in DNA (e.g., adenine "A," guanine "G," thymine "T" and cytosine "C") or RNA (e.g. A, G, uracil "U" and C). The term "nucleic acid" encompasses the terms "oligonucleotide" and "polynucleotide." "Oligonucleotide," as used herein, refers collectively and interchangeably to two terms of art, "oligonucleotide" and "polynucleotide." Note that although oligonucleotide and polynucleotide are distinct terms of art, there is no exact dividing line between them and they are used interchangeably herein. The term "adaptor" may also be used interchangeably with the terms "oligonucleotide" and "polynucleotide." In addition, the term "adaptor" can indicate a linear adaptor (either single stranded or double stranded) or a stem-loop adaptor. These definitions generally refer to at least one single-stranded molecule, but in specific embodiments will also encompass at least one additional strand that is partially, substantially, or fully complementary to at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss," a double-stranded nucleic acid by the prefix "ds," and a triple stranded nucleic acid by the prefix "ts."

A "nucleic acid molecule" or "nucleic acid target molecule" refers to any single-stranded or double-stranded nucleic acid molecule including standard canonical bases, hypermodified bases, non-natural bases, or any combination of the bases thereof. For example and without limitation, the nucleic acid molecule contains the four canonical DNA bases—adenine, cytosine, guanine, and thymine, and/or the four canonical RNA bases—adenine, cytosine, guanine, and uracil. Uracil can be substituted for thymine when the nucleoside contains a 2'-deoxyribose group. The nucleic acid molecule can be transformed from RNA into DNA and from DNA into RNA. For example, and without limitation, mRNA can be created into complementary DNA (cDNA) using reverse transcriptase and DNA can be created into RNA using RNA polymerase. A nucleic acid molecule can be of biological or synthetic origin. Examples of nucleic acid molecules include genomic DNA, cDNA, RNA, a DNA/RNA hybrid, amplified DNA, a pre-existing nucleic acid library, etc. A nucleic acid may be obtained from a human sample, such as blood, serum, plasma, cerebrospinal fluid, cheek scrapings, biopsy, semen, urine, feces, saliva, sweat, etc. A nucleic acid molecule may be subjected to various treatments, such as repair treatments and fragmenting treatments. Fragmenting treatments include mechanical, sonic, and hydrodynamic shearing. Repair treatments include nick repair via extension and/or ligation, polishing to create blunt ends, removal of damaged bases, such as deaminated, derivatized, abasic, or crosslinked nucleotides, etc. A nucleic acid molecule of interest may also be subjected to chemical modification (e.g., bisulfite conversion, methylation/demethylation), extension, amplification (e.g., PCR, isothermal, etc.), etc.

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" may refer to nucleic acid(s) that are substantially complementary, as may be assessed by the same nucleotide comparison set forth above. The term "substantially complementary" may refer to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double-stranded nucleic acid molecule during hybridization. In certain embodiments, the term "substantially complementary" refers to at least one nucleic acid that may hybridize to at least one nucleic acid strand or duplex in stringent conditions. In certain embodiments, a "partially complementary" nucleic acid comprises at least one sequence that may hybridize in low stringency conditions to at least one single or double-stranded nucleic acid, or contains at least one sequence in which less than about 70% of the nucleobase sequence is capable of base-pairing with at least one single or double-stranded nucleic acid molecule during hybridization.

The term "non-complementary" refers to nucleic acid sequence that lacks the ability to form at least one Watson-Crick base pair through specific hydrogen bonds.

The term "degenerate" as used herein refers to a nucleotide or series of nucleotides wherein the identity can be selected from a variety of choices of nucleotides, as opposed to a defined sequence. In specific embodiments, there can be a choice from two or more different nucleotides. In further specific embodiments, the selection of a nucleotide at one particular position comprises selection from only purines, only pyrimidines, or from non-pairing purines and pyrimidines.

"Sample" means a material obtained or isolated from a fresh or preserved biological sample or synthetically-created source that contains nucleic acids of interest. Samples can include at least one cell, fetal cell, cell culture, tissue specimen, blood, serum, plasma, saliva, urine, tear, vaginal secretion, sweat, lymph fluid, cerebrospinal fluid, mucosa secretion, peritoneal fluid, ascites fluid, fecal matter, body exudates, umbilical cord blood, chorionic villi, amniotic fluid, embryonic tissue, multicellular embryo, lysate, extract, solution, or reaction mixture suspected of containing immune nucleic acids of interest. Samples can also include non-human sources, such as non-human primates, rodents and other mammals, other animals, plants, fungi, bacteria, and viruses.

As used herein in relation to a nucleotide sequence, "substantially known" refers to having sufficient sequence information in order to permit preparation of a nucleic acid molecule, including its amplification. This will typically be about 100%, although in some embodiments some portion of an adaptor sequence is random or degenerate. Thus, in specific embodiments, substantially known refers to about 50% to about 100%, about 60% to about 100%, about 70% to about 100%, about 80% to about 100%, about 90% to about 100%, about 95% to about 100%, about 97% to about 100%, about 98% to about 100%, or about 99% to about 100%.

X. Further Processing of Target Nucleic Acids

A. Amplification of DNA

A number of template-dependent processes are available to amplify the nucleic acids present in a given template sample. One of the best known amplification methods is the polymerase chain reaction (referred to as PCR™) which is described in detail in U.S. Pat. Nos. 4,683,195, 4,683,202, and 4,800,159 and in Innis et al., 1990, each of which is incorporated herein by reference in their entirety. Briefly, two synthetic oligonucleotide primers, which are complementary to two regions of the template DNA (one for each strand) to be amplified, are added to the template DNA (that need not be pure), in the presence of excess deoxynucleotides (dNTP's) and a thermostable polymerase, such as, for example, Taq (*Thermus aquaticus*) DNA polymerase. In a series (typically 30-35) of temperature cycles, the target DNA is repeatedly denatured (around 90° C.), annealed to the primers (typically at 50-60° C.) and a daughter strand extended from the primers (72° C.). As the daughter strands are created they act as templates in subsequent cycles. Thus, the template region between the two primers is amplified exponentially, rather than linearly.

B. Sequencing of DNA

Methods are also provided for the sequencing of the library of adaptor-linked fragments. Any technique for sequencing nucleic acids known to those skilled in the art can be used in the methods of the present disclosure. DNA sequencing techniques include classic dideoxy sequencing reactions (Sanger method) using labeled terminators or primers and gel separation in slab or capillary, sequencing-by-synthesis using reversibly terminated labeled nucleotides, pyrosequencing, 454 sequencing, allele specific hybridization to a library of labeled oligonucleotide probes, sequencing-by-synthesis using allele specific hybridization to a library of labeled clones that is followed by ligation, real time monitoring of the incorporation of labeled nucleotides during a polymerization step, and SOLID™ sequencing.

The nucleic acid library may be generated with an approach compatible with Illumina sequencing such as a Nextera™ DNA sample prep kit, and additional approaches for generating Illumina next-generation sequencing library preparation are described, e.g., in Oyola et al. (2012). In other embodiments, a nucleic acid library is generated with a method compatible with a SOLID™ or Ion Torrent sequencing method (e.g., a SOLID™ Fragment Library Construction Kit, a SOLID™ Mate-Paired Library Construction Kit, SOLID™ ChIP-Seq Kit, a SOLID™ Total RNA-Seq Kit, a SOLID™ SAGE™ Kit, a AMBION® RNA-Seq Library Construction Kit, etc.). Additional methods for next-generation sequencing methods, including various methods for library construction that may be used with embodiments of the present invention are described, e.g., in Pareek (2011) and Thudi (2012).

In particular aspects, the sequencing technologies used in the methods of the present disclosure include the HISEQ™ system (e.g., HISEQ™ 2000 and HISEQ™ 1000), the NEXTSEQ™ 500, and the MISEQ® system from Illumina, Inc. The HISEQ™ system is based on massively parallel sequencing of millions of fragments using attachment of randomly fragmented genomic DNA to a planar, optically transparent surface and solid phase amplification to create a high density sequencing flow cell with millions of clusters, each containing about 1,000 copies of template per sq. cm. These templates are sequenced using four-color DNA sequencing-by-synthesis technology. The MISEQ® system uses TRUSEQ™, Illumina's reversible terminator-based sequencing-by-synthesis.

Another example of a DNA sequencing technique that can be used in the methods of the present disclosure is 454 sequencing (Roche) (Margulies et al., 2005). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated.

Another example of a DNA sequencing technique that can be used in the methods of the present disclosure is SOLID™ technology (Life Technologies, Inc.). In SOLID™ sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

Another example of a DNA sequencing technique that can be used in the methods of the present disclosure is the IonTorrent system (Life Technologies, Inc.). Ion Torrent uses a high-density array of micro-machined wells to perform this biochemical process in a massively parallel way. Each well holds a different DNA template. Beneath the wells is an ion-sensitive layer and beneath that a proprietary Ion sensor. If a nucleotide, for example a C, is added to a DNA template and is then incorporated into a strand of DNA, a hydrogen ion will be released. The charge from that ion will change the pH of the solution, which can be detected by the proprietary ion sensor. The sequencer will call the base, going directly from chemical information to digital information. The Ion Personal Genome Machine (PGM™) sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection—no scanning, no cameras, no light—each nucleotide incorporation is recorded in seconds.

Another example of a sequencing technology that can be used in the methods of the present disclosure includes the single molecule, real-time (SMRT™) technology of Pacific Biosciences. In SMRT™, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in and out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

A further sequencing platform includes the CGA Platform (Complete Genomics). The CGA technology is based on preparation of circular DNA libraries and rolling circle amplification (RCA) to generate DNA nanoballs that are arrayed on a solid support (Drmanac et al. 2009). Complete genomics' CGA Platform uses a novel strategy called combinatorial probe anchor ligation (cPAL) for sequencing. The process begins by hybridization between an anchor molecule and one of the unique adapters. Four degenerate 9-mer oligonucleotides are labeled with specific fluorophores that correspond to a specific nucleotide (A, C, G, or T) in the first position of the probe. Sequence determination occurs in a reaction where the correct matching probe is hybridized to a template and ligated to the anchor using T4 DNA ligase. After imaging of the ligated products, the ligated anchor-probe molecules are denatured. The process of hybridization, ligation, imaging, and denaturing is repeated five times using new sets of fluorescently labeled 9-mer probes that contain known bases at the n+1, n+2, n+3, and n+4 positions.

XI. Kits

The technology herein includes kits for analyzing copy number variation or allele frequencies in a DNA sample. A "kit" refers to a combination of physical elements. For example, a kit may include, for example, one or more components such as nucleic acid primers, enzymes, reaction buffers, an instruction sheet, and other elements useful to practice the technology described herein. These physical elements can be arranged in any way suitable for carrying out the invention.

The components of the kits may be packaged either in aqueous media or in lyophilized form. The container means of the kits will generally include at least one vial, test tube, flask, bottle, syringe or other container means, into which a component may be placed, and preferably, suitably aliquoted (e.g., aliquoted into the wells of a microtiter plate). Where there is more than one component in the kit, the kit also will generally contain a second, third or other additional container into which the additional components may be separately placed. However, various combinations of components may be comprised in a single vial. The kits of the present invention also will typically include a means for containing the nucleic acids, and any other reagent containers in close confinement for commercial sale. Such containers may include injection or blow molded plastic containers into which the desired vials are retained. A kit will also include instructions for employing the kit components as well the use of any other reagent not included in the kit. Instructions may include variations that can be implemented.

XII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Calibration Results

An exemplary calibration experiment of the ERBB2 QASeq panel was performed on a normal cell line gDNA sample NA18562, which should not contain ERBB2 amplifications, to analyze the quantitation variability and potential LoD. The workflow was as described in the "QASeq Workflow" section. Taq polymerase was used in all the PCR steps. Denaturation was performed at 95° C., and annealing/extension was performed at 60° C. (except for the universal PCR step, in which annealing/extension was performed at 68° C.). Because all original molecules with UMIs attached need to be present in the NGS output, 15 reads were reserved for each molecule/UMI. For an input of 2500 haploid genomic copies and a 20-amplicon panel, the total reads needed is about $$2\times2500\times20\times15=1{,}500{,}000.$$

Note that each of the strands in one DNA duplex carries a different UMI in this workflow, so 2500 haploid genomic copies=5000 molecule number=8.3 ng gDNA. This experiment was performed on an Illumina MISEQ® instrument.

Exact string match was used to align NGS reads to the amplicon sequences; the alignment rate was between 50% and 70% for different libraries. Next, the UMI family sizes and unique UMI numbers were analyzed. The distribution of UMI family size peaked at ≈20 for most loci (FIG. 5). UMI families containing obvious PCR errors (i.e., G bases found in the poly(H) UMI sequence) and UMIs with family size <4 were removed (FIG. 5). If the UMI attachment rate were perfect, the unique UMI number should be equal to the original molecule number in the sample. For an input of 2500 haploid genomic copies (5000 molecules), between 632 and 3065 unique UMI number were obtained depending on the loci (FIG. 6).

In order to estimate the LoD of this assay, libraries were prepared for four different DNA inputs: 75, 250, 750, and 2500 haploid genomic copies; each condition was replicated five times. The CNV ratio of the sample was calculated as described in the "Data Analysis Workflow" section. The standard deviation of CNV ratio $$(\sigma_{CNV\ ratio})$$

across five replicates was used to evaluate quantitation variability; the LoD of the assay can be estimated as $$3\sigma_{CNV ratio}.$$

Simulations were also performed to calculate the theoretical $\sigma_{CNV\ ratio}$; note that the $\sigma_{CNV\ ratio}$ and LoD should decrease if the input molecule number increases. The $\sigma_{CNV\ ratio}$ was higher than the theoretical value (FIG. 7), which was as expected because the UMI attachment bias and amplification bias cannot be eliminated. The current best $$\sigma_{CNV\ ratio}$$

is 1% at 2500 haploid genomic copies input; to be conservative, a linear approximation based on all 4 data points was used, and a $$\sigma_{CNV\ ratio} = 2\%$$

was obtained; therefore, the estimated LoD was about 6% of extra copies. Based on an extrapolation to 50,000 haploid genomic copies input, the potential $$\sigma_{CNV\ ratio}$$

was 0.3%, and the LoD was about 1%. Another way to evaluate LoD is by testing a series of calibration samples containing different frequencies of extra copies; the lowest detectable frequency of extra copies is the LoD.

Example 2—CNV Detection Results in FFPE Samples

Two FFPE slides were analyzed using the example ERBB2 panel described in the "Multiplexed PCR Panel Design" section and Example 1. The FFPE slides (purchased from Asterand) were from the same lung cancer tumor, which is not expected to contain ERBB2 CNV. First, DNA was extracted using a QIAamp DNA FFPE Tissue Kit (Qiagen), and >6 μg of DNA per sample was obtained. The libraries were prepared using the same methods as described in Example 1. 8.3 ng extracted DNA was used for each library, which is equivalent to 2500 haploid genomic copies and 5000-molecule input. The number of NGS reads reserved for each library (1,500,000 reads) was the same as 2500 haploid genomic copies input cell line gDNA libraries.

Data analysis was performed using the same methods as described in Example 1. A similar pattern of UMI family size distribution to the cell line gDNA libraries was obtained (FIG. 8A). The unique UMI numbers were smaller than cell line gDNA libraries with 2500 haploid genomic copies input. The UMI attachment yield of FFPE samples was about ¼ of that of cell line gDNA on average, which indicates that 300% more FFPE DNA needs to be loaded to achieve the same LoD as the cell line gDNA sample (FIG. 8B).

The calculated CNV ratios of the FFPE samples are shown in FIG. 8C. The inferred LoD=15% of this assay was based on calibration results on 750 haploid genomic copies input cell line gDNA, which have similar unique UMI numbers to the FFPE libraries. Based on current results, CNV of ERBB2 was not detected in these FFPE slides. Because LoD decreases as the input molecule number increases, an LoD of 6% can be achieved, based on the calibration results on 2500 haploid genomic copies input cell line gDNA.

Example 3—CNV Quantitation Results in Spike-in Clinical FFPE Samples

A 100-plex QASeq panel was used to quantitate the ploidy of ERBB2 in breast cancer FFPE samples. 50-plex were in the ERBB2 gene region (see Table 3 for primer sequences; primer names have "ERBB2" in them), and 50-plex were in the short arm of Chromosome 17 as the Reference (see Table 3 for primer sequences; primer names have "Ref" in them).

Two previously characterized FFPE DNA samples (1 "normal" sample and 1 "ERBB2 amplified abnormal" sample) were mixed to generate 2.5%, 5%, and 10% ERBB2 FEC samples. The "normal" sample DNA was extracted from a FFPE lung cancer sample (purchased from Asterand), which should not have ERBB2 amplification (FEC=0%); the "ERBB2 amplified abnormal" sample DNA was extracted from a FFPE breast cancer sample (purchased from OriGene), which has a ERBB2 FEC of 78%. The sample input was 8.3 ng DNA per library (quantitated by qPCR). The "normal" sample was tested with 5 replicated NGS libraries prepared separately, each with 8.3 ng DNA input. The experimental normalized FEC values are shown in FIG. 13. Normalized FEC was calculated as:

$$\text{Normalized } FEC_{sample} = (1 + FEC_{sample})/(1 + FEC_{normal\ sample}) - 1$$

The $FEC_{normal\ sample}$ was the average of 5 replicates. The LoD of the CNV panel was estimated as:

$$FEC_{LoD} = 3 \times \sigma_{normal\ sample}/(1 + FEC_{normal\ sample}) = 0.85\%$$

Here, the $\sigma_{normal\ sample}$ was the standard deviation of 5 replicates. CNV was successfully detected in 2.5%, 5%, and 10% ERBB2 FEC samples, because their calculated FEC are outside the 3 standard deviation range (see FIG. 13). The experimental normalized FEC of ERBB2 correlates well with the expected value.

Example 4—Comprehensive Panel for Both Mutation and CNV Quantitation

The method presented (QASeq) can not only be used for CNV quantitation, but also for NGS error correction and mutation quantitation. In each QASeq amplicon, the region between the 3' of fP and the 3' of rPin is the Mutation Detection Region (MDR); any small variations (including base substitutions, deletions, and insertions smaller than 500 bp) in the MDR can be detected with an LoD of 0.1%-0.3%.

This is much better than standard non-UMI NGS methods for mutation detection, which has an LoD≈1%.

A 179-plex comprehensive panel was developed and tested for both mutation and CNV quantitation in breast cancer samples. Every plex contains 3 primers: fP (a.k.a. SfP), rPin (a.k.a SrPB), and rPout (a.k.a. SrPA) as stated in previous sections. 95 primer sets were used solely for CNV quantitation, including 45 in gene ERBB2, and 50 in the short arm of Chromosome 17 as the reference. 5 primer sets in the ERBB2 gene were used for both CNV and mutation quantitation. Another 79 primer sets were used for mutation quantitation only. UfP and UrP were used for universal amplification (see Table 3 for sequences).

CNV quantitation was done the same way as described in previous sections; data processing workflow for mutation quantitation is summarized in FIG. 14. After optional adapter trimming, NGS reads were aligned to the amplicon sequences. At each locus, reads were divided into UMI families; the UMI families with errors in the UMI sequence were removed, and the UMI families with small UMI family sizes (≤3) were also removed. Next, the consensus MDR sequence of each UMI family was found, which is usually the MDR sequence appearing the highest number of times in the UMI family. The last step was comparing the consensus sequence to the wildtype MDR sequence, and performing de novo mutation calling. The VAF of one mutation can be calculated as: VAF=Number of UMI families with the mutation/Total number of UMI families.

This 179-plex panel was tested on the Multiplex I cfDNA Reference Standard Set from Horizon Discovery. Three replicated NGS libraries of the Wild Type cfDNA Reference Standard and three replicates of the 0.3% cfDNA Reference Standard (created by mixing 0.1% cfDNA Reference Standard and 1% cfDNA Reference Standard) were tested. The sample input was 8.3 ng DNA per library (quantitated by qPCR).

The overall on-target rate was greater than 50% (i.e. >50% of the NGS reads can be aligned to the amplicons) for all the libraries; the conversion rate (i.e., the percentage of input molecules sequenced) has an average of 62%, and 97% of the plexes have >10% conversion rate (see FIG. 15). Error rates after UMI correction vary in different nucleotide positions; in the three replicated libraries of Horizon Discovery Multiplex I Wild Type cfDNA Reference Standard, highest error rates were 0.23%, 0.20%, and 0.23%, and average error rates were 0.006%, 0.005%, and 0.005% (see FIG. 16). The mutation quantitation capability was validated using the 0.3% cfDNA Reference Standard. The experimental VAF of 6 mutations were generally consistent with the expected VAF; the difference was mostly due to stochasticity in sampling a small number (≤9) of mutation molecules (see FIG. 17).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Lun et al., "Noninvasive prenatal diagnosis of monogenic diseases by digital size selection and relative mutation dosage on DNA in maternal plasma," *Proc. Natl. Acad. Sci. U.S.A.,* 105:19920-19925, 2008.

The invention claimed is:

1. A method for performing copy number variant (CNV) detection and/or allele ratio quantitation of at least ten target genomic loci each having three target genomic DNA regions for high-throughput sequencing, the method comprising:

(a) obtaining a genomic DNA sample;

(b) amplifying at least a portion of the genomic DNA sample by performing two cycles of multiplex PCR using:

(i) a population of first oligonucleotides each comprising, from 5' to 3', a first region, a second region having a length between 1 and 50 nucleotides, a third region comprising at least four degenerate nucleotides, and a fourth region comprising a sequence that is complementary to a first target genomic DNA region for one of the target genomic loci; and (ii) a population of second oligonucleotides each comprising, from 5' to 3', a fifth region, a sixth region having a length between 1 and 50 nucleotides, and a seventh region comprising a sequence that is complementary to a second target genomic DNA region for one of the target genomic loci;

(c) amplifying a product of step (b) by performing at least three cycles of PCR with an annealing temperature that is 0-10° C. higher than an annealing temperature used in step (b) and using:

(i) a third oligonucleotide comprising a sequence that is able to hybridize to the reverse complement of at least a portion of the first region; and (ii) a fourth oligonucleotide comprising a sequence that is able to hybridize to the reverse complement of at least a portion of the fifth region;

(d) amplifying a product of step (c) by performing at least one cycle of PCR using a population of fifth oligonucleotides each comprising, from 5' to 3', an eighth region, a ninth region having a length between 1 and 50 nucleotides, and a tenth region comprising a sequence that is complementary to a third target genomic DNA region for one of the target genomic loci, wherein the third target genomic DNA region is at least one nucleotide closer to the first target genomic DNA region than the second target genomic DNA region for each of the target genomic loci, thereby producing amplicons;

(e) sequencing the amplicons by performing quantitative next-generation sequencing (qNGS) to obtain sequencing reads; and (f) counting the sequencing reads to perform CNV detection and/or allele ratio quantitation for the at least 10 target genomic regions.

2. The method of claim 1, wherein the third region is a unique molecular identifier (UMI).

3. The method of claim 1, wherein, for each of the target genomic loci, the third target genomic DNA region is between 1 nucleotide and 10 nucleotides closer to the first target genomic DNA region than the second target genomic DNA region.

4. The method of claim 1, wherein the first region and the eighth region (1) are universal primer binding sites, (2) comprise a full or partial NGS adapter sequence, or (3) both (1) and (2).

5. The method of claim 1, wherein the melting temperatures of the first region and the fifth region are between 0° C. and 10° C. higher than the melting temperatures of the fourth region and the seventh region.

6. The method of claim 1, wherein the method further comprises, between steps (d) and (e):

amplifying the product of step (d) by PCR using primers that hybridize to the first region and the eighth region, wherein the primers comprise an index sequence for next-generation sequencing.

7. The method of claim 1, wherein, for each of the target genomic loci, the first target genomic DNA region and the second target genomic DNA region are (1) on opposite strands of the genomic DNA, (2) separated by between 40 nucleotides and 500 nucleotides, or (3) both (1) and (2).

8. The method of claim 1, wherein step (b) comprises an extension time of about 30 minutes.

9. The method of claim 1, wherein step (c) comprises an extension time of about 30 seconds.

10. The method of claim 1, wherein step (d) comprises an extension time of about 30 minutes.

11. The method of claim 2, wherein step (f) comprises:

(i) aligning NGS reads to the targeted genomic loci and grouping the NGS reads into subgroups based on the loci to which they align;

(ii) dividing the NGS reads at each locus based on their UMI sequences such that all NGS reads carrying the same UMI sequence are grouped as one UMI family;

(iii) removing UMI families resulting from PCR errors or NGS errors;

(iv) calling the genetic identity for each remaining UMI family;

(v) counting the number of unique UMI sequences at each locus; and (vi) calculating the allele ratio.

12. The method of claim 2, wherein the allele ratio is defined as $R_{allele}=N_1/N_2$, wherein $N_1$ is unique UMI number for the first genetic identity, and wherein $N_2$ is unique UMI number for the second genetic identity.

* * * * *